US009409938B2

(12) United States Patent
Schrock et al.

(10) Patent No.: US 9,409,938 B2
(45) Date of Patent: Aug. 9, 2016

(54) TUNGSTEN OXO ALKYLIDENE COMPLEXES FOR ZSELECTIVE OLEFIN METATHESIS

(71) Applicants: Massachusetts Institute of Technology, Cambridge, MA (US); Trustees of Boston College, Chestnut Hill, MA (US)

(72) Inventors: Richard Royce Schrock, Winchester, MA (US); Dmitry Vyacheslavovich Peryshkov, Cambridge, MA (US); Amir H. Hoveyda, Lincoln, MA (US)

(73) Assignees: Massachusetts Institute of Technology, Cambridge, MA (US); Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 14/797,848

(22) Filed: Jul. 13, 2015

(65) Prior Publication Data

US 2016/0009746 A1    Jan. 14, 2016

Related U.S. Application Data

(63) Continuation of application No. 13/671,109, filed on Nov. 7, 2012, now Pat. No. 9,085,595.

(60) Provisional application No. 61/556,643, filed on Nov. 7, 2011.

(51) Int. Cl.
| | |
|---|---|
| C07F 11/00 | (2006.01) |
| C07C 6/04 | (2006.01) |
| C07C 11/02 | (2006.01) |
| B01J 31/22 | (2006.01) |

(52) U.S. Cl.
CPC ............. *C07F 11/00* (2013.01); *B01J 31/2208* (2013.01); *B01J 31/2286* (2013.01); *B01J 31/2295* (2013.01); *C07C 6/04* (2013.01); *C07C 11/02* (2013.01); *B01J 2231/543* (2013.01); *B01J 2531/66* (2013.01); *C07C 2531/34* (2013.01)

(58) Field of Classification Search
CPC ............. C07F 11/00; C07F 11/02; C07F 6/04
See application file for complete search history.

(56) References Cited

U.S. PATENT DOCUMENTS

| 4,727,215 A | 2/1988 | Schrock |
|---|---|---|
| 5,639,900 A | 6/1997 | Bell et al. |
| 6,121,473 A | 9/2000 | Schrock et al. |
| 7,932,397 B2 | 4/2011 | Hock et al. |
| 8,222,469 B2 | 7/2012 | Schrock et al. |
| 8,350,073 B2 | 1/2013 | Hock et al. |
| 8,362,311 B2 | 1/2013 | Schrock et al. |
| 8,546,500 B2 | 10/2013 | Hoveyda et al. |
| 8,598,400 B2 | 12/2013 | Hoveyda et al. |
| 8,829,219 B2 | 9/2014 | Hock et al. |
| 9,073,801 B2 | 7/2015 | Hoveyda et al. |
| 9,079,173 B2 | 7/2015 | Schrock et al. |
| 9,085,595 B2 | 7/2015 | Schrock et al. |
| 2011/0015430 A1 | 1/2011 | Schrock et al. |
| 2011/0065915 A1 | 3/2011 | Malcolmson et al. |
| 2011/0077421 A1 | 3/2011 | Schrock et al. |
| 2011/0237815 A1 | 9/2011 | Hock et al. |
| 2011/0245477 A1 | 10/2011 | Hoveyda et al. |
| 2012/0323000 A1 | 12/2012 | Hoveyda et al. |
| 2013/0116434 A1 | 5/2013 | Schrock et al. |
| 2013/0274482 A1 | 10/2013 | Schrock et al. |
| 2013/0281706 A1 | 10/2013 | Hock et al. |
| 2014/0309388 A1 | 10/2014 | Schrock et al. |
| 2014/0316088 A1 | 10/2014 | Schrock et al. |
| 2014/0330018 A1 | 11/2014 | Czirok et al. |
| 2014/0378637 A1 | 12/2014 | Schrock et al. |
| 2015/0065723 A1 | 3/2015 | Hock et al. |
| 2015/0240008 A1 | 8/2015 | Schrock et al. |
| 2015/0246348 A1 | 9/2015 | Hoveyda et al. |

FOREIGN PATENT DOCUMENTS

CN          102015106 A       4/2011

OTHER PUBLICATIONS

Schrock, Journal of Molecular Catalysis A: Chemical 213 (2004) pp. 21-30.*
Ahn, S. and Mayr, A., Tungsten Tris(pyrazolyl)borate Cage Expansion by Formal Insertion of an Alkylidyne Group into a Tungsten—Nitrogen Bond, Journal of the American Chemical Society, 118:7408-4709 (1996).
Barrado, G. et al., Adducts of the Lewis Acid [B9C6F5)3] with Transition Metal Oxo Compounds, J. Chem. Soc., Dalton Trans., 1061-1066 (1999).
Basset, J. M. et al., A Study of cis-trans Isomerization During Matathesis of cis-2-Pentene with the Catalytic System: W(CO)5O(C6H5)3+C2H5AlCl2+O2, Journal of Catalysts, 34:152-155 (1974).
Blosch, L. L. et al., Synthesis of an Air-Stable, Moisture-Stable, and Thermally Stable Tungsten (VI) Oxo Alkylidene Complex. Precursor to an Air- and Moisture-Stable ROMP Catalyst, Journal of the American Chemical Society, 113:7066-7068 (1991).
Bryan, J. C. and Mayer, J. M., Oxidative Addition of Carbon—Oxygen and Carbon—Nitrogen Double Bonds to WCl2(PMePh2)4. Synthesis of Tungsten Metallaoxirane and Tungsten Oxo- and Imido-Alkylidene Complexes, Journal of the American Chemical Society, 112:2298-2308 (1990).
Burwell, R. L. and Brenner, A., The Nature of the Mo(CO)6/Alumina Catalyst for the Metathesis of Olefins, Mol. Catal., 1:77-84 (1976).
Calderon, N. et al., Olefin metathesis. I. Acyclic Vinylenic Hydrocarbons, J. Am. Chem. Soc., 90(15):4133-4140 (1968).
Churchill, M. R. et al., X-Ray Crystallographic Studies on Octahedral Oxo Alkylidene Complexes of Tungsten VI: (W=O)(=CHCMe3)(PMe3)2 Cl2 and W(=O)(=CHCMe3)(PEt3)2Cl2, Journal of Organometallic Chemistry, 204:C17-C20 (1981).
Click, D. R. et al., Highly Electrophilic Lanthanide Complexes Containing Fluorinated Amido Ligands: Multiple Ln***F interactions, Agostic Interactions and N6-Arene Coordination, Chem. Commun., 633-634 (1999).

(Continued)

*Primary Examiner* — Robert Harlan
(74) *Attorney, Agent, or Firm* — Stoel Rives LLP

(57) ABSTRACT

The current application describes tungsten oxo alkylidene complexes for olefin metathesis.

20 Claims, 11 Drawing Sheets

(56) References Cited

OTHER PUBLICATIONS

Conley, M. P. et al., A Well-Defined Silica-Supported Tungsten Oxo Alkylidene Is a Highly Active Alkene Metathesis Catalyst, Journal of the American Chemical Society, 135:19068-19070 (2013).

Cornelissen, C. et al., Aluminum Pentafluorophenyl-Amide Complexes, J. Chem., 85:135-140 (2007).

Crane, T. W. et al., Conversion of Tungsten(IV) Oxo-Alkyne Complexes to Oxo-Vinylidene Complexes, Organometallics, 18:1897-1903 (1999).

Cummins, C. C. et al., Synthesis of Terminal Vanadium (V) Imido, Oxo, Sulfido, Selenido, and Tellurido Complexes by Imido Group or Chalcogenide Atom Transfer to Trigonal-Monopyramidal V[N3N] (N3N=[(Me3SiNCH2CH2)3N]3-), Inorg. Chem., 33:1448-1457 (1994).

De La Mata, F. J. and Grubbs, R.H., Synthesis and Reactions of Tungsten Oxo Vinylalkylidene Complexes: Reactions fo WCl2(O)(PX3)(X=OMe, R) Precursors with 3, 3-Diphenylcyclopropene, Organometallics, 15:577-584 (1996).

De La Mata, J. F., Synthesis and characterization of tungsten oxo alkylidene complexes via the reaction of WCl2(O)[PX3]3 (PX3=P(OMe)3, PMe2Ph, PMePh2) with 4,8-dioxaspiro[2,5]oct-1-ene (ketalcyclopropene), Journal of Organometallic Chemistry, 525:183-189 (1996).

Dickie, D. A. et al., Synthesis of the Bulky m-terphenyl phenol Ar*OH (Ar*=C6H3-2,6-Mes2, Mes=2,4,6-trimethylphenyl) and the Preparation and Structural Characterization of Several of its Metal Complexes, Can. J. Chem, 86:20-31 (2008).

Dreisch, K. et al., Synthesis and Structure of Dimethoxyethane-Dichlorodioxo-Tungsten(VI)—A Highly Soluble Derivative of Tungsten Dioxodichloride, Polyhedron, 10(20/21):2417-2421 (1991).

Feinstein-Jaffe, I. et al., A Molecule Containing the OWOWO unit. Synthesis, Structure, and Spectroscopy of W2O3(CH2CMe3))6, J. Am. Chem. Soc., 106:6305-6310 (1984).

Feinstein-Jaffe, I. et al., Aqueous Tungsten(VI) Alkyl Chemistry, J. Am. Chem. Soc., 105:7176-7177 (1983).

Feinstein-Jaffe, I. et al., Preparation of Anionic Tungsten(VI) Alkyl Complexes Containing Oxo or Sulfido Ligands and the X-ray Structure of [N(C2H5)4]{WO2[OC(CH3)2C(CH3)2O][CH2C(CH3)3]}, Organometallics, 4: 1189-1193 (1985).

Feldman, J. et al., Preparation and Reactivity of Tungsten (VI) Metallacyclobutane Complexes. Square Pyramids versus Trigonal Bipyramids, Organometallics, 9:2535-2548 (1990).

Feldman, J. et al., Recent advances in the chemistry of "d0" alkylidene and metallacyclobutane complexes, Prog. Inorg. Chem, 39:1-74 (1991).

Feldman, J. et al., Trigonal-Bipyramidal and Square-Pyramidal Tungstacyclobutane Intermediates Are Both Present in Systems in Which Olefins Are Metathesized by Complexes of the Type, Organometallics, 8:2266-2268 (1989).

Flook, M. M. et al., Z-Selective Olefin Metathesis Processes Catalyzed by a Molybdenum Hexaisopropylterphenoxide Monopyrrolide Complex, J. Am. Chem. Soc., 131(23): 7962-7963 (2009).

Flook, M. M. Thesis: Z-Selective Olefin Metathesis Processes and Cis/Syndioselective ROMP with High Oxidation State Molybdenum Alkylidenes. Massachusetts Institute of Technology (2012).

Flook, M. M., et al. Z-Selective and Syndioselective Ring-Opening Metathesis Polymerization (ROMP) Initiated by Monoaryloxidepyrrolide (MAP) Catalysts, Macromolecule, 43:7515-7522 (2010).

Flook, M. M., et al., Synthesis of cis, syndiotactic ROMP Polymers Containing Alternating Enantiomers. J. Am. Chem. Soc. 133, 1784 (2011).

Galsworthy, J. R. et al., Reactions of Organometallic Oxometals Complexes with B9C6F5)3: Synthesis, Structure, Bonding and Reactivity of [Mo(n5-C5H4Me)2-{OB(C6F5)3}], J. Chem. Soc., Dalton Trans., 15-19 (1998).

Gibson, V. C. et al., New, Improved Synthesis of the Group 6 Oxyhalides, W(O)Cl4, W(O)2Cl2 and Mo(O)2Cl2, Polyhedron, 7(7):579-480 (1988).

Giesbrecht, G. R. et al., Neutral and Anionic Transition Metal Complexes Supported by Decafluorodiphenylamido Ligands: X-ray Crystal Structures of {Na(THF)2}{Ti[N(C6F5)2]4}, {K(n6-C6H5Me)2}{ZrCl2[N(C6F5)2]3}, K{VCl[N(C6F5)2]3}, Fe[N(C6F5)2]2(THF)2 and Co[N(C6F5)2]2(py)2, Polyhedron, 22: 153-163 (2003).

Hayano, S. and Tsunogae, Y., A New Method for Catalytic Syntheses of Block Copolymers via ROMP: Development of Stereoblock Copoly(endo-dicyclopentadiene), Chem. Lett., 37(5): 518-519 (2008).

Hayano, S. and Tsunogae, Y., Syndioselective Ring-Opening Metathesis Polymerization of endo-Dicyclopentadiene with Tungsten Complexes Having Imido Ligands: Development of Crystalline Syndiotactic Hydrogenated Poly(endo-dicyclopentadiene), Macromolecules, 39: 30-38 (2006).

Hayano, S. and Tsunogae, Y., Syndioselective Ring-Opening Metathesis Polymerization of endo-Dicyclopentadiene with Tungsten Complexes Having Imido Ligands: Development of Crystalline Syndiotactic Hydrogenated Poly(endo-dicyclopentadiene), Macromolecules, A-I (2005).

Hayano, S. and Tsunogae, Y., Syndiospecific Ring-opening Metathesis Polymerization of endo-Dicyclopentadiene by Tungsten(VI) Phenylimido Catalyst, Chem. Lett., 34(11): 1520-1521 (2005).

Hayano, S. et al., Hydrogenated Ring-Opened Poly(endo-dicyclopentadiene)s Made via Stereoselective ROMP Catalyzed by Tungsten Complexes: Crystalline Tactic Polymers and Amorphous Atactic Polymer, Macromolecules, 39: 4663-4670 (2006).

Hayano, S. et al., Stereospecific Ring-Opening Metathesis Polymerization of Cycloolefins Using Novel Molybdenum and Tungsten Complexes Having Biphenolate Ligands. Development of Crystalline Hydrogenated Poly(endo-dicyclopentadiene) and Poly(norbornene), Macromolecules, 36: 7422-7431 (2003).

Hayano, S. et al., Stereospecific Ring-Opening Metathesis Polymerization of endo-Dicyclopentadiene by Schrock-Hoveyda Catalyst and Novel Mo- and W-based Complexes. Development of Crystalline Hydrogenated Poly(endo-dicyclopentadiene), Chem. Lett., 32(8): 670-671 (2003).

Heppekausen, J., et al., Practical New Silyloxy-Based Alkyne Metathesis Catalysts with Optimized Activity and Selectivity Profiles. J. Am. Chem. Soc. 132, 11045-11057 (2010).

Heppekausen, J., et al., Rendering Schrock-type Molybdenum Alkylidene Complexes Air Stable: User-Friendly Precatalysts for Alkene Metathesis. Angew. Chem. Int. Ed. 50, 7829 (2011).

Herrmann et al., Synthesen und Strukturen neuer Komplexe des 2,2'-Bipyridins mit Niob, Molybdan, Woldfram und Rhenium in hohen Oxidationsstufen, Chem. Ber., 123: 271-276 (1990).

Ibrahem, I. et al., Highly Z- and enantioselective ring-opening/cross-metathesis reactions catalyzed by stereogenic-at-Mo adamantylimido complexes, J Am Chem Soc., 131(11):3844-5 (2009).

International Search Report for PCT/US12/63898, 3 pages (Jan. 28, 2013).

Jiang, A. J. et al., Fundamental studies of tungsten alkylidene imido monoalkoxidepyrrolide complexes. J Am Chem Soc. 131(22):7770-80 (2009).

Jiang, A. J. et al., Highly Z-selective metathesis homocoupling of terminal olefins, J Am Chem Soc. 131(46):16630-1 (2009).

Khvorost, A. et al., Lithium Bis(pentafluorophenyl)amide—Syntheses and Structural Characterization of its Complexes with Diethyl Ether and THF, Z. Anorg. Allg. Chem., 630: 885-889 (2004).

Koppang, R., Use of a Lithium Amide Suspension in Tetrahydrofuran for Preparation of Some Polyfluorophenyl- and Polyfluorodiphenylamines, Acta Chem. Scand, 25: 3067-3071 (1971).

Kress, J. and Osborn, J. A., Tungsten Carbene Complexes in Olefin Metathesis: A Cationic and Chiral Active Species, J. Am. Chem. Soc., 105: 6346-6347 (1983).

Kress, J. et al., Molecular Complexes for Efficient Metathesis of Olefins. The Oxo-Ligand as a Catalyst-Cocatalyst Bridge and the Nature of the Active Species, J. Chem. Soc. Chem. Comm., 1039-1040 (1981).

(56) References Cited

OTHER PUBLICATIONS

Kress, J. et al., Tungsten(IV) Carbenes for the Metathesis of Olefins, Direct Observation and Identification of the Chain Carrying Carbene Complexes in a Highly Active Catalyst System, J. Chem. Soc. Chem. Comm., 514-516 (1982).
Kress, J. et al., Tungsten(VI) and Molybdenum(VI) Oxo-alkyl Species. Their Role in the Metathesis of Olefins, J. Chem. Soc. Chem. Comm., 431-432 (1980).
Kuhn, F. E. et al., Synthesis and Catalytic Application of Octahedral Lewis Base Adducts of Dichloro and Dialkyl Dioxotungsten(VI), Inorg. Chem., 41(17): 4468-4477 (2002).
Lapointe, A. M. et al., Imido/oxo Exchange Between Osmium and Tantalum as a Route to Os(NAr)2R2 and OsO(NAr)R2 Complexes (R=CH2CMe3, CH2CMe2Ph, CH2SiMe3) and Attempts to Induce a-Hydrogen Abstraction to Give Alkylidene Complexes, Organometallics, 14: 2699-2703 (1995).
Legdzins, P. et al., New Types of Organometallic Oxo Complexes Containing Tungsten, Organometallics, 4: 1470-1471 (1985).
Lehtonen, A. and Sillanpaa, R., Reactions of Tris(ethanediolato)tungsten and Tungsten Oxytetrachloride with Aminotris(phenol)s: Alkoxide, Chloro, and Alkyl Derivatives of Oxotungsten(VI) Complexes with Tetradentate [O3N]-Type Ligands, Organometallics, 24: 2795-2800 (2005).
Lichtscheidl, A. G., et al., Molybdenum Monoaryloxide Pyrrolide Alkylidene Complexes That Contain Mono-*ortho*-substituted Phenyl Imido Ligands. Organometallics. 31, 2388 (2012).
Malcolmson, S. J. et al., Highly efficient molybdenum-based catalysts for enantioselective alkene metathesis. Nature. 456(7224):933-7 (2008).
Marinescu, S. C. et al., Ethenolysis reactions catalyzed by imido alkylidene monopyrrolide monoaryloxide (MAP) complexes of molybdenum. J Am Chem Soc. Aug. 12, 2009;131(31):10840-1 (2009).
Marinescu, S. C. et al., Syntheses of Variations of Stereogenic-at-Metal Imido Alkylidene Complexes of Molybdenum, Organometallics, 31: 6336-6343 (2012).
Marinescu, S. C., et al., Isolation of Pure Disubstituted E Olefins through Mo-Catalyzed Z-Selective Ethenolysis of Stereoisomeric Mixtures. J. Am. Chem. Soc. 133, 11512 (2011).
Marinescu, S. C., et al., Room-Temperature Z-Selective Homocoupling of α-Olefins by Tungsten Catalysts. Organometallics. 30, 1780-1782 (2011).
Marinescu, S. C., et al., Syntheses and Structures of Molybdenum Imido Alkylidene Pyrrolide and Indolide Complexes. Organometallics. 27, 6570 (2008).
Meek, S. J., et al., Catalytic Z-selective olefin cross-metathesis for natural product synthesis. Nature 471, 461-466 (2011).
Mocella, M. T. et al., Mechanism of the Olefin Metathesis Reaction. 4. Catalyst Precursors in Tungsten(VI) Based Systems, J. Am. Chem. Soc., 98: 4689-4690 (1976).
Muetterties, E. L. and Band, E., Olefin Metathesis Reaction: Characterization of an Active Catalyst Precursor, CH3WOCl3 O(C2H5)2, from the WOCl4-(CH3)2Mg Reaction, J. Am. Chem. Soc., 102: 6572-6574 (1980).
O'Donoghue, M. B. et al., Preparation of Well-Defined, Metathetically Active Oxo Alkylidene Complexes of Tungsten, Organometallics, 15:1334-1336 (1996).
Patterson, J. M. and Soedigdo, S., The Thermal Isomerization of Some Trisubstitute Pyrroles, J. Org. Chem, 33(5): 2057-2061 (2012).
Peryshkov, D. V. et al., B(C6F5)3 Activation of Oxo Tungsten Complexes that are Relevant to Olefin Metathesis, Organometallics, 32:5256-5259 (2013).
Peryshkov, D. V. et al., Synthesis of Tungsten Oxo Alkylidene Complexes, Organometallics, 7278-7286 (2012).
Peryshkov, D. V., et al., Z-Selective Olefin Metathesis Reaction Promoted by Tungsten Oxo Alkylidene Complexes. J. Am. Chem. Soc. 133, 20754 (2011).
Poater, A. et al., Understanding d(0)-olefin metathesis catalysts: which metal, which ligands? J Am Chem Soc. 129(26):8207-16 (2007).
Rappe, A. K. and Goddard, W. A., Olefin Metathesis. A Mechanistic Study of High-Valent Group 6 Catalysts, J. Am. Chem. Soc., 104:448-456 (1982).
Rocklage, S. M. et al., Facile Conversion of Tungsten(VI) Neopentylidyne Complexes into Oxo and Imido Neopentylidene Complexes and the Crystal Structure of W (CCMe3)(PHPh)(PEt3)2Cl21, Organometallics, 1:1332-1338 (1982).
Rocklage, S. M. et al., How Niobium and Tantalum Complexes of the Type M(CHCMe3)(PR3)2Cl3 Can be Modified to Give Olefin Metathesis Catalysts, J. Am. Chem. Soc., 103:1440-1447 (1981).
Rosenfeld, D. C. et al., Synthesis and Reactivity of (silox)2R2WO (R=Cl, Me, Et, nPr and nBu; silox=OSitBu3) and (silox)2MO2 (M=Mo and W), Polyhedron, 25: 251-258 (2006).
Sanchez-Nieves, J. et al., n2-Iminoacyl and n2-Acyl Monocyclopetadienyl Tantalum Complexes Bearing Oxo and Oxo-Borane Ligands, Eur. J. lnorg. Chem., 127-132, 2006.
Schrauzer, G. N. et al., Studies of Molybdenum Compounds, 4. Synthesis and Structure of Dibenzyl(2,2'-bipyridyl)dioxomolybdenum(VI), Organometallics, 2: 1163-1166 (1983).
Schrauzer, G. N. et al., Studies of Molybdenum Compounds, 6. Diaryl(2,2'-bipyridyl)dioxomolybdenum(VI) and Related Compounds, Organometallics, 7: 279-282, 1988.
Schrauzer, G. N. et al., Studies of Molybdenum Compounds. 1. Synthesis and Structure of Dioxo (dimethyl)(2,2'-bipyridyl)molybdenum(VI), Prototype of a New Class of Organomolybdenum(VI) Compounds, Organometallics, 1: 44-47 (1982).
Schrauzer, G. N. et al., Studies of Molybdenum Compounds. 5. Diethyl(2,2'-bipyridyl)dioxomolybdenum(VI) and Other Higher Dialkyl Derivatives of Dioxomolybdenum(VI), Organometallics, 5: 2452-2456 (1986).
Schrauzer, G. N. et al., Studies of Organomolybdenum Compounds. 2. Synthesis, Structure, and Properties of Dioxodineopentyl(2,2'-bipryidyl)molybdenum(VI) and of Related Compounds, Organometallics, 2(4): 481-485 (1983).
Schrock, R. et al., Preparation and Characterization of Active Niobium, Tantalum and Tungsten Metathesis Catalysts, Molec. Catal., 8: 73-83 (1980).
Schrock, R. R. et al., Fundamental Studies of Molybdenum and Tungsten Methylidene and Metallacyclobutane Complexes, Organometallics, 29: 5241-5251 (2010).
Schrock, R. R. et al., Recent advances in olefin metathesis by molybdenum and tungsten imido alkylidene complexes, Journal of Molecular Catalysis A: Chemical 213:21-30 (2004).
Schrock, R. R., Recent advances in high oxidation state Mo and W imido alkylidene chemistry. Chem Rev. 109(8):3211-3226 (2009).
Schrock, R. R., The Alkoxide Ligand in Olefin and Acetylene Metathesis Reactions, Polyhedron, 14(22): 3177-3195 (1995).
Schrock, R., High oxidation state multiple metal-carbon bonds. Chem. Rev. 102, 145-179 (2002).
Shutov, P. L. et al., Intramolecular nucleophilic Substitution in C6F5 moiety. The Fluoride-dialkylamino Exchange in Decafluorodiphenlamino Moiety, P. L. et al., Fluor. Chem., 130: 1017-1021 (2009).
Siaj, M. et al., Preparation and olefin-metathesis activity of cyclopentylidene-oxo initiator sites on a molybdenum carbide surface, Journal of Organometallic Chemistry, 691:5497-5504 (2006).
Solans-Monfort, X. et al., Oxo vs Imido Alkylidene d0-Metal Species: How and Why Do They Differ in Structure, Activity, and Efficiency in Alkene Metathesis?, Organometallics, 31: 6812-6822 (2012).
Solans-Monfort, X. et al., Shutting Down Secondary Reaction Pathways: The Essential Role of the Pyrrolyl Ligand in Improving Silica Supported d0-ML4 Alkene Metathesis Catalysts from DFT Calculations, J. Am. Chem. Soc., 132: 7750-7757 (2010).
Stanciu, C. et al., Synthesis and Characterization of the Very Bulky Phenols Ar*OH and Ar'OH (Ar8=C6H3-2,6-Trip2, Trip=C6H2-2,4,6-iPr3; Ar'=C6H3-2,6-Dipp2, Dipp=C6H3-2,6-iPr2) and Their Lithium and Sodium Derivatived (LiOAr')2 and (NaOAr*)2., Eur. J. Inorg. Chem, 3495-3500 (2003).

(56) References Cited

OTHER PUBLICATIONS

Stavropoulos, P. et al., Oxo Methyls of Molybdenum(V), Tungsten(V) and Rhenium(V): X-Ray Crystal Structure of (Me4WO)2Mg(thf)4, Polyhedron, 6(5): 1081-1087 (1987).

Suzuki, Y. et al., Phase Separation of Block Copolymer Synthesized via Catalytic ROMP Reaction, Chem. Lett., 40: 114-115 (2011).

Wampler, K. M. et al., Synthesis of Molybdenum Imido Alkylidene Complexes that Contain Siloxides, Organometallics, 26: 6674-6680 (2007).

Wampler, K. M., Synthesis Investigations of Molybdenum Pyrrolide and Related Complexes, Massachusetts Institute of Technology: 1-260 (2010).

Wang, C. et al., Density Functional Molecular Orbit Theory Study on the Mechanism of Me2W(CH2)2+O2 → Me2WOCH2+HCHO, Journal of Liaoning Normal University, 26(2):163-167 (2003).

Weber, K. et al., Recent Advances in the Synthesis of N-Heteroatom Substituted Imido Complexes Containing a Nitrido Bridge [M=N-E] (M=Group 4, 5, and 6 Metal, E=B, Si, Ge, P, S), Z. Anorg. Allg. Chem., 629: 744-754 (2003).

Wengrovius, J. H., et al., Synthesis and Characterization of Tungsten Oxo Neopentylidene Complexes, Organometallics. 1, 148 (1982).

Wengrovius, J. H., et al., Tungsten-Oxo Alkylidene Complexes as Olefin Metathesis Catalysts and the Crystal Structure of W(O)(CHCM3)(PEt3)(Cl2). J. Am. Chem. Soc. 102, 4515 (1980).

Wolf, J. R. et al., Exchange of Oxo Ligands in OsO4 with Imido Ligands in Mo(NAr)2(O-t-Bu)2, a Facile Route to Os(NAr)2O2 and Os(NAr)3O and Osmium(VI) Complexes of the Type Os(NAr)2L2 (NAr=N-2,6-C6H3-i-Pr2; L=a phosphine), Inorg. Chem., 32: 4155-4156 (1993).

Wolff, F. et al., Reactivity of B9C6F5)3 with Oxovanadium(v) Complexes VOL3 (L=OCH2CF3,NEt2): Formation of the Organometallic Vanadium(v) Complex [VO(u-OCH2CF3)(OCH2CF3)(C6F5)]2 and the Lewis Acid Adduct [(Et2N)3VO B(C6F5)3], Eur. J. Inorg. Chem., 628-632 (2003).

Written Opinion for PCT/US12/63898, 4 pages (Jan. 28, 2013).

Yao, S. et al., Isomerization of an N-Heterocyclic Germylene to an Azagermabenzen-1-ylidene and Its Coupling to a Unique Bis(germylene), Organometallics, 29: 5353-5357 (2010).

Yu, M., et al., Synthesis of macrocyclic natural products by catalyst-controlled stereoselective ring-closing metathesis. Nature, 479, 88-93 (2011).

Yuan, J. et al., Pentafluorophenylimido Alkylidene Complexes of Molybdenum and Tungsten, Organometallics, 31: 4650-4653 (2012).

Zhang, C. et al., Diphenyl(2,2'-bipyridyl)dioxomolybdenum(VI) and -tungsten(VI): A Comparative Study, Organometallics, 9: 1307-1311 (1990).

Zhang, C. et al., Synthesis, Structure, and Reactions of 2,2'-Bipyridyl Complexes of Tetramethyloxotungsten(VI) and Dimethyldioxotungsten(VI) and of Related Compounds, Organometallics, 9: 1016-1020 (1990).

\* cited by examiner

TUNGSTEN OXO ALKYLIDENE COMPLEXES FOR ZSELECTIVE OLEFIN METATHESIS

CROSS-REFERENCE TO RELATED APPLICATIONS

This application is a Continuation of U.S. patent application Ser. No. 13/671,109, filed Nov. 7, 2012, now U.S. Pat. No. 9,085,595, which claims priority to U.S. Provisional Application Ser. No. 61/556,643, filed Nov. 7, 2011, the entirety of each of which is incorporated herein by reference.

STATEMENT REGARDING FEDERALLY SPONSORED RESEARCH OR DEVELOPMENT

THIS INVENTION WAS MADE WITH GOVERNMENT SUPPORT UNDER GRANT NO. DE-FG02-86ER13564 AWARDED BY THE U.S. DEPARTMENT OF ENERGY AND UNDER GRANT NO. CHE-1111133 AWARDED BY THE NATIONAL SCIENCE FOUNDATION. THE GOVERNMENT HAS CERTAIN RIGHTS IN THIS INVENTION.

FIELD OF THE INVENTION

The present invention generally relates to olefin metathesis catalyst precursors.

BACKGROUND

Catalytic olefin metathesis has transformed chemical synthesis and offers exceptionally efficient pathways for synthesis of alkenes. A great number of commercially important molecules contain olefins. Such specialty chemicals include biologically active molecules, oleochemicals, renewables, fine chemicals, and polymeric materials, to name a few. Moreover, many reactions in organic chemistry require alkenes as starting materials. Accordingly, there remains an unmet need for improved methods and catalysts for metathesis reaction.

DETAILED DESCRIPTION OF CERTAIN EMBODIMENTS

Figure 1:
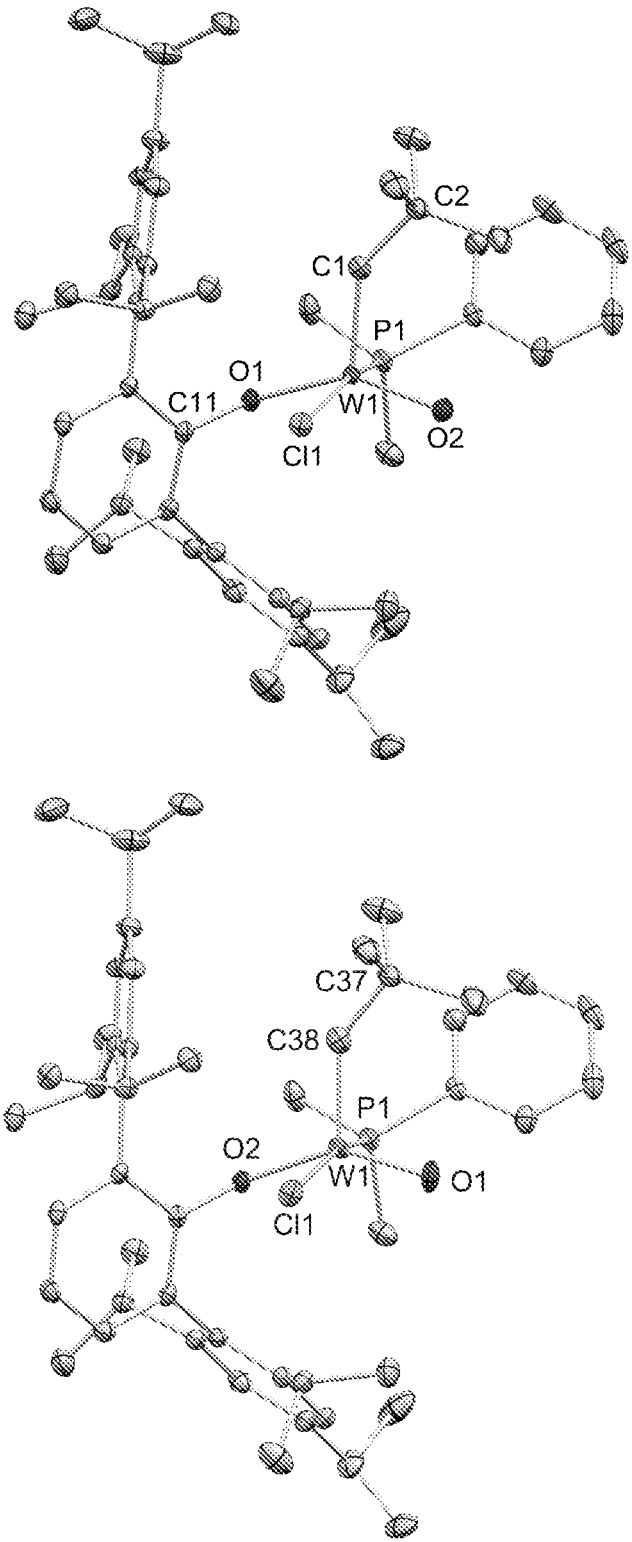
FIG. 1. Thermal ellipsoid drawing of I-1.

1. General Description of Certain Embodiments of the Invention

Early in the development of olefin metathesis catalysts that contain tungsten, it was shown that metathetically more active and reproducible systems were produced when tungsten oxo complexes were deliberately employed or were present as impurities in WCl$_6$ (K. J. Ivin and J. C. Mol, Olefin Metathesis and Metathesis Polymerization; Academic Press: San Diego, 1997; K. J. Ivin, Olefin Metathesis; Academic Press, 1983; Calderon, N.; Ofstead, E. A.; Ward, J. P.; Judy, W. A.; Scott, K. W. J. Am. Chem. Soc. 1968, 90, 4133; Basset, J. M.; Coudurier, G.; Praliaud, H. J. Catal. 1974, 34, 152; Mocella, M. T.; Rovner, R.; Muetterties, E. L. J. Am. Chem. Soc. 1976, 98, 4689; Burwell, R. L., Jr.; Brenner, A. J. Mol. Catal. 1976, 1, 77; Kress, J. R. M.; Russell, M. J. M.; Wesolek, M. G.; Osborn, J. A. J. Chem. Soc. Chem. Comm. 1980, 431; Muetterties, E. L.; Band, E. 1980, 102, 6572; Kress, J. R. M.; Wesolek, M. G.; Le Ny; J.-P.; Osborn, J. A. J. Chem. Soc. Chem. Comm. 1981, 1039; Kress, J. R. M.; Wesolek, M. G.; Osborn, J. A. J. Chem. Soc. Chem. Comm. 1982, 514; Kress, J. R. M.; Osborn, J. A. J. Am. Chem. Soc. 1983, 105, 6346). The possibility that oxo alkylidene complexes, e.g., W(O)(CHR)X$_2$ (where X is a chloride, alkoxide, etc.), are the true catalysts in at least some of the "classical" olefin metathesis systems became more likely when 1 (L=PMe$_3$ and other phosphines) was prepared and isolated in good yield (Schrock, R. R.; Rocklage, S. M.; Wengrovius, J. H.; Rupprecht, G.; Fellmann, J. *J. Molec. Catal.* 1980, 8, 73; Wengrovius, J. H.; Schrock, R. R.; Churchill, M. R.; Missert, J. R.; Youngs, W. J. *J. Am. Chem. Soc.* 1980, 102, 4515; Wengrovius, J. H.; Schrock, R. R. *Organometallics* 1982, 1, 148). Compound 1 was the first high oxidation state tungsten alkylidene complex that would both (i) metathesize terminal and internal olefins (in the presence of a trace of AlCl$_3$) and (ii) produce a new alkylidene that could be observed as a consequence of olefin metathesis. The three most likely possibilities for the role of AlCl$_3$ are removal of halide to give monocationic or dicationic species, removal of a phosphine to give the 16 electron monophosphine adduct (Wengrovius, J. H.; Schrock, R. R.; Churchill, M. R.; Missert, J. R.; Youngs, W. J. *J. Am. Chem. Soc.* 1980, 102, 4515), or activation through addition of AlCl$_3$ to the oxo ligand (Schrock, R. R.; Rocklage, S. M.; Wengrovius, J. H.; Rupprecht, G.; Fellmann, J. *J. Molec. Catal.* 1980, 8, 73; Wengrovius, J. H.; Schrock, R. R.; Churchill, M. R.; Missert, J. R.; Youngs, W. J. *J. Am. Chem. Soc.* 1980, 102, 4515; Wengrovius, J. H.; Schrock, R. R. *Organometallics* 1982, 1, 148).

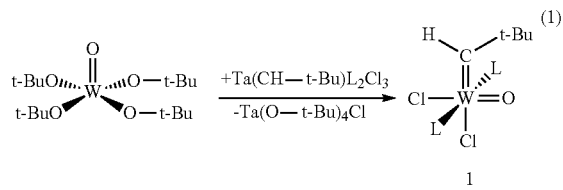

By the time 1 was discovered, tantalum alkylidene complexes had been turned into functional olefin metathesis catalysts through use of alkoxides as ligands (Rocklage, S. M.; Fellmann, J. D.; Rupprecht, G. A.; Messerle, L. W.; Schrock, R. R. *J. Am. Chem. Soc.* 1981, 103, 1440; Schrock, R. R. *Polyhedron* 1995, 14, 3177). Therefore, some attempts were made to prepare a W(O)(CH-t-Bu)(OR)$_2$ species from 1, but no such species were isolated and characterized. In view of the synthetic problems encountered upon attempted alkylation of oxo complexes, including removal of the oxo ligand entirely (Kress, J. R. M.; Wesolek, M. G.; Osborn, J. A. *J. Chem. Soc. Chem. Comm.* 1982, 514; Kress, J. R. M.; Osborn, J. A. *J. Am. Chem. Soc.* 1983, 105, 6346), and to protect alkylidenes against bimolecular decomposition, attention turned to the synthesis of imido alkylidene complexes of W and Mo, especially those containing a phenylimido ligand such as N(2,6-i-Pr$_2$C6H$_3$) (Schrock, R. R. *Chem. Rev.* 2002, 102, 145-180; Schrock, R. R. in Braterman, P. R., Ed. *Reactions of Coordinated Ligands*, Plenum: New York, 1986, p. 221). In the face of the success of imido alkylidene complexes in olefin metathesis, interest in oxo alkylidene complexes in the last 25 years has been sparce (Bryan, J. C.; Mayer, J. C. *J. Am. Chem. Soc.* 1990, 112, 2298; Blosch, L. L.; Abboud, K.; Boncella, J. M. *J. Am. Chem. Soc.* 1991, 113, 7066; Ahn, S.; Mayr, A. *J. Am. Chem. Soc.* 1996, 118, 7408; De la Mata, F. J.; Grubbs, R. H. *Organometallics* 1996, 15, 577; O'Donoghue, M. B.; Schrock, R. R.; LaPointe, A. M.; Davis. W. M. *Organometallics* 1996, 15, 1334; Crane, T. W.; White, P. S.; Templeton, J. L. *Organometallics* 1999, 18, 1897).

The most recent development in Mo and W imido alkylidene chemistry has been monoaryloxide monopyrrolide (MAP) complexes (Schrock, R. R. *Chem. Rev.* 2009, 109, 3211). One of the most interesting discoveries is the ability of some MAP catalysts to promote Z selective metathesis reactions as a consequence of the presence of a relatively "large" aryloxide and "small" imido group (Ibrahem, I; Yu, M.; Schrock, R. R.; Hoveyda, A. H. *J. Am. Chem. Soc.,* 2009, 131, 3844; Flook, M. M.; Jiang, A. J.; Schrock, R. R.; Müller, P.; Hoveyda, A. H. J. Am. Chem. Soc. 2009, 131, 7962; Flook, M. M.; Gerber, L. C. H.; Debelouchina, G. T.; Schrock, R. R. *Macromolecules* 2010, 43, 7515; Flook, M. M.; Ng, V. W. L.; Schrock, R. R. *J. Am. Chem. Soc.* 2011, 133, 1784; Jiang, A. J.; Zhao, Y.; Schrock, R. R.; Hoveyda, A. H. *J. Am. Chem. Soc.* 2009, 131, 16630; Marinescu, S. C; Schrock, R. R.; Müller, P.; Takase, M. K.; Hoveyda, A. H. *Organometallics,* 2011, 30, 1780; Marinescu, S. C.; Levine, D. S.; Zhao, Y.; Schrock, R. R.; Hoveyda, A. H. *J. Am. Chem. Soc.* 2011, 133, 11512; Malcolmson, S. J.; Meek, S. J.; Sattely, E. S.; Schrock, R. R.; Hoveyda, A. H. *Nature* 2008, 456, 933; Meek, S. J.; O'Brien, R. V.; Llaveria, J.; Schrock, R. R.; Hoveyda, A. H. *Nature* 2011, 471, 461; Yu, M.; Wang, C.; Kyle, A. F.; Jakubec, P.; Dixon, D. J.; Schrock, R. R.; Hoveyda, A. H. *Nature* 2011, 479, 88). The preferred metal for Z selective couplings of terminal olefins at this time appears to be tungsten and the most successful aryloxide ligand has been O-2,6-(2,4,6-triisopropylphenyl)$_2$C6H$_3$ or OHIPT. (The more active molybdenum complexes (Schrock, R. R., King, A. J.; Marinescu, S. C.; Simpson, J. H.; Müller, P. *Organometallics* 2010, 29, 5241) appear to isomerize the Z product to E.) It has been proposed that the unusual steric demands of the OHIPT ligand force all metallacyclobutane substituents to one side of the metallacycle ring, and therefore allow only Z products to form. Since an oxo ligand is smaller than any NR ligand (R not H), the question arose as to whether MAP versions of tungsten oxo alkylidene complexes would be useful Z selective catalysts.

In some embodiments, the present invention provides a compound of formula I:

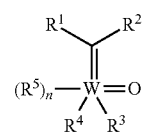

wherein:
each of R$^1$ and R$^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;
each R$^3$ and R$^4$ is halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

n is 0, 1, or 2;

each $R^5$ is independently a monodentate ligand, or two $R^5$ are taken together with their intervening atoms to form an optionally substituted bidentate group; and two or more of $R^1$, $R^2$, $R^3$, $R^4$ and $R^5$ may be taken together with their intervening atoms to form an optionally substituted polydentate ligand.

Further aspects of compounds of formula I are described in detail, infra.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75*th* Ed. Additionally, general principles of organic chemistry are described in "Organic Chemistry", Thomas Sorrell, University Science Books, Sausalito: 1999, and "March's Advanced Organic Chemistry", 5*th* Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$C(O)R°; —OC(O)(CH$_2$)$_{0-4}$SR—, SC(S)SR°; —(CH$_2$)$_{0-4}$SC(O)R; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR)R°; —C(O)C(O)R°; —C(O)CH$_2$C(O)R; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R; —N(R°)S(O)$_2$NR°$_2$; —N(R°)S(O)$_2$R; —N(OR)RO; —C(NH)NR°$_2$; —P(O)$_2$R°; —P(O)R°$_2$; —OP(O)R°$_2$; —OP(O)(OR°)$_2$; —SiR°$_3$; —OSiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —$O(haloR^{\bullet})$, —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR_2$, —$NO_2$, —$SiR°_3$, —$OSiR°_3$, —$C(O)SR^{\bullet}$, —$(C_{1-4}$ straight or branched alkylene)$C(O)OR^{\bullet}$, or —$SSR^{\bullet}$ wherein each $R°$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, -(halo$R^{\bullet}$), —OH, —$OR^{\bullet}$, —$O(haloR^{\bullet})$, —CN, —C(O)OH, —$C(O)OR°$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a ligand may be either monodentate or polydentate. A ligand may have hapticity of more than 1. In some cases, the ligand has a hapticity of 1 to 10. For ligand with hapticity greater than 1, as sometimes done in the art, a single bond may be drawn between the ligand and the metal. In some cases, a ligand is alkylidene. In some cases, a ligand is nitrogen-containing ligand In some cases, a ligand is oxygen-containing ligand. In some cases, a ligand is phosphorus-containing ligand.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

As used herein, the term "phosphorus-containing ligand" may be used to refer to ligands comprising at least one phosphorus atom. In some cases, the phosphorus atom binds to the metal. In other cases, the phosphorus-containing ligand may bind to the metal center via a different atom (i.e., an atom other than the phosphorous). The phosphorus-containing ligand may have phosphorus atom of various oxidation states. In some cases the phosphorus-containing ligand is phosphine. In some cases the phosphorus-containing ligand is phosphite. In some cases the phosphorus-containing ligand is phosphate. The phosphorus-containing ligand may be either monodentate or polydentate. In some cases, two or more phosphorus atoms bind to the metal. In some cases, one or more phosphorus atoms together with one or more non-phosphorus atoms bind to the metal.

In may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

As defined herein, a "metal complex" is any complex used to form a provided precursor complex or any complex generated from a provided precursor complex (e.g., for use as a catalyst in a reaction such as a metathesis reaction).

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

3. Description of Certain Embodiments of the Invention

In some embodiments, the present invention provides complexes which serve as precursors to metathesis catalysts, including stereogenic-at-metal catalysts. In certain embodiments, provided precursor complexes are used in metathesis reactions, such as olefin metathesis reactions.

As used herein, the term "metathesis reaction" is given its ordinary meaning in the art and refers to a chemical reaction in which two reacting species exchange partners in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, and the like. The metathesis reaction may occur between two substrates which are not joined by a bond (e.g., intermolecular metathesis reaction) or between two portions of a single substrate (e.g., intramolecular metathesis reaction). In some embodiments, complexes of the present invention are useful in the formation of a metathesis product with high enantioselectivity and/or high ratio of Z:E isomers, and/or high ratio of E:Z isomers.

In some embodiments, a compound is isolated as a Lewis base adduct. The terms "Lewis base" and "Lewis base adduct" are known in the art and refer to a chemical moiety capable of donating a pair of electrons to another chemical moiety. In some embodiments, the coordination of Lewis base molecules to a compound may result in a complex having a plane of symmetry with respect to the metal center. However, a stereogenic metal center may be formed by facile removal of the Lewis base molecules and/or replacement of one or more Lewis base molecules with one or more molecules that cause the complex to lose the plane of symmetry with respect to the metal center. For example, the provided compound may be formed and stored as a Lewis base adduct, and may be "activated" in a subsequent reaction step to generate a catalyst with a stereogenic metal center.

Some embodiments of the invention provide a composition comprising a provided precursor complex which, upon treatment to generate a metal complex, affords a catalyst suitable for use in reactions described herein. In some embodiments, treatment of the provided precursor complex generates a metal complex comprising a stereogenic metal atom and two or more ligands that bind the metal atom. In some embodiments, each ligand associated with the metal complex comprises an organic group. The ligands may be monodentate ligands, i.e., the ligands bind the stereogenic metal atom via one site of the ligand (e.g., a carbon atom or a heteroatom of the ligand). In some embodiments, a monodentate ligand may bind the metal center via a single bond or a multiple bond. In some embodiments, the metal complex comprises at least one ligand lacking a plane of symmetry. That is, at least one ligand bound to the stereogenic metal atom is a chiral ligand. In some embodiments, the metal complex comprises a nitrogen-containing ligand, including chiral and/or achiral nitrogen-containing ligands. For example, the ligand may be a chiral or achiral nitrogen heterocycle, such as a pyrrolide. In some embodiments, the metal complex comprises an oxygen-containing ligand, including chiral and/or achiral oxygen-containing ligands. For example, the ligand may be a chiral or achiral biphenyl group substituted with at least one oxygen-containing moiety, e.g., a phenol. In some cases, the metal atom may be bound to at least one carbon atom. In some embodiments, the metal complex comprises an phosphorus-containing ligand, including chiral and/or achiral oxygen-containing ligands.

Some aspects of the invention can be realized with provided precursor complexes comprising two or more ligands, wherein each ligand is a monodentate ligand, i.e., each ligand binds or coordinates the metal center via one coordination site of the metal only, or via one site of the ligand only. In some embodiments, a provided precursor complex comprises primarily monodentate ligands. In some embodiments, a provided precursor complex comprises at least one bidentate ligand, i.e., the ligand binds or coordinates the metal center via two coordination sites. In some embodiments, a provided precursor complex comprises a monodentate ligand and a bidentate ligand.

In some embodiments, methods of the present invention comprise use of a provided compound wherein, upon generation of a metal complex in situ, the metal complex is present in a diastereomeric ratio greater than 1:1. In some embodiments, the metal complex is present in a diastereomeric ratio greater than about 5:1, greater than about 7:1, greater than about 10:1, greater than about 20:1, or, in some cases, greater. In certain embodiments, the metal complex generated in situ is an active metal catalyst complex. Exemplary such active metal catalyst complexes include metal complexes described herein for use in, inter alia, olefin metathesis reactions.

In some embodiments, the present invention provides a compound of formula I:

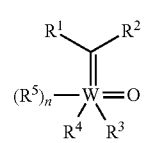

wherein:
each of $R^1$ and $R^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;
each of $R^3$ and $R^4$ is independently halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

n is 0, 1, or 2;

each $R^5$ is independently a monodentate ligand, or two $R^5$ are taken together with their intervening atoms to form an optionally substituted bidentate group; and two or more of $R^1$, $R^2$, $R^3$, $R^4$ and $R^5$ may be taken together with their intervening atoms to form an optionally substituted polydentate ligand.

As defined generally above, each of $R^1$ and $R^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R, wherein R is hydrogen, or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, both of $R^1$ and $R^2$ are hydrogen. In some embodiments, one of $R^1$ and $R^2$ is hydrogen and the other is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, the $R^1$ group or the $R^2$ group of formula I is optionally substituted $C_{1-20}$ aliphatic. In some embodiments, $R^1$ or $R^2$ is optionally substituted $C_{1-20}$ alkyl. In certain embodiments, $R^1$ or $R^2$ is $C_{1-6}$ alkyl substituted with phenyl and one or two additional substituents. In certain embodiments, $R^1$ or $R^2$ is a lower alkyl group optionally substituted with one or two methyl groups and phenyl. In certain embodiments, $R^1$ or $R^2$ is —C(Me)$_2$Ph. In certain embodiments, $R^1$ or $R^2$ is —C(Me)$_3$. In some embodiments, $R^1$ or $R^2$ is selected from any of those $R^1$ or $R^2$ groups depicted or described herein.

In certain embodiments, $R^2$ is hydrogen and $R^1$ is R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R, wherein each R is independently as defined above and described herein. In certain embodiments, $R^2$ is hydrogen and $R^1$ is R, wherein R is as defined above and described herein. In certain embodiments, $R^2$ is hydrogen and $R^1$ is optionally substituted $C_{1-20}$ aliphatic. In some embodiments, $R^2$ is hydrogen and $R^1$ is optionally substituted $C_{1-20}$ alkyl. In certain embodiments, $R^2$ is hydrogen and $R^1$ is $C_{1-6}$ alkyl substituted with phenyl and one or two additional substituents. In certain embodiments, $R^2$ is hydrogen and $R^1$ is a lower alkyl group optionally substituted with one or two methyl groups and phenyl. In certain embodiments, $R^2$ is hydrogen and $R^1$ is —C(Me)$_2$Ph. In certain embodiments, $R^2$ is hydrogen and $R^1$ is —C(Me)$_3$. In some embodiments, $R^2$ is hydrogen and $R^1$ is selected from any of those $R^1$ or $R^2$ groups depicted or described herein.

In some embodiments, the present invention provides a compound of formula I-a, below:

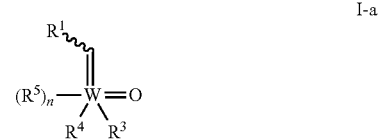

I-a wherein each of n, $R^1$, $R^3$, $R^4$, and $R^5$ is as defined above and described in embodiments herein, both singly and in combination.

In some embodiments, both $R^1$ and $R^2$ are hydrogen.

As defined generally above, each $R^3$ and $R^4$ is halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur, wherein each R is independently as defined above or described herein.

In some embodiments, at least one of $R^3$ and $R^4$ is halogen. In other embodiments, each $R^3$ and $R^4$ is independently R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur, wherein each R is independently as defined above or described herein.

In certain embodiments, at least one of $R^3$ and $R^4$ is —N(R)$_2$. In some embodiments, both of $R^3$ and $R^4$ are —N(R)$_2$, wherein one R is hydrogen and the other is optionally substituted $C_{1-20}$ aliphatic.

In other embodiments, $R^3$ and $R^4$ are —N(R)$_2$, wherein the two R groups are taken together with the nitrogen to form an optionally substituted 3-8 membered saturated, partially unsaturated, or aryl ring having 0-3 additional heteroatoms not including the N atom from N(R)$_2$ independently selected from nitrogen, oxygen, or sulfur, wherein $R^3$ and $R^4$ are coordinated to W via a nitrogen. In some embodiments, the two R groups are taken together with the nitrogen to form an optionally substituted 5-membered heteroaryl ring having 0-3 additional nitrogen atoms not including the N atom from N(R)$_2$. Such rings include optionally substituted pyrrol-1-yl, pyrazol-1-yl, imidazol-1-yl, and triazol-1-yl. In some embodiments, such rings are unsubstituted pyrrol-1-yl, pyrazol-1-yl, imidazol-1-yl, and triazol-1-yl.

In some embodiments, at least one of $R^3$ and $R^4$ is an optionally substituted 5-6 membered monocyclic heteroaryl ring having at least one nitrogen and 0-3 additional heteroatoms independently selected from nitrogen, oxygen, or sulfur. In some embodiments, at least one of $R^3$ and $R^4$ is an optionally substituted group selected from pyrrolyl, pyrazolyl, imidazolyl, triazolyl, oxazolyl, isoxazoly, oxadiazoyl, thiazolyl, and thiazolyl. In some embodiments, at least one of $R^3$ and $R^4$ is an unsubstituted group selected from pyrrolyl, pyrazolyl, imidazolyl, triazolyl, oxazolyl, isoxazoly, oxadiazoyl, thiazolyl, and thiazolyl. In some embodiments, at least one of $R^3$ and $R^4$ is a substituted group selected from pyrrolyl, pyrazolyl, imidazolyl, triazolyl, oxazolyl, isoxazoly, oxadiazoyl, thiazolyl, and thiazolyl. In some embodiments, at least one of $R^3$ and $R^4$ is an unsubstituted pyrrolyl. In some embodiments, each of $R^3$ and $R^4$ is an unsubstituted pyrrolyl. In some embodiments, at least one of $R^3$ and $R^4$ is a substituted pyrrolyl. In some embodiments, each of $R^3$ and $R^4$ is a substituted pyrrolyl.

In other embodiments, at least one of $R^3$ and $R^4$ is an optionally substituted 8-10 membered bicyclic heteroaryl ring having at least one nitrogen and 0-4 additional heteroatoms independently selected from nitrogen, oxygen, or sulfur. In some embodiments, at least one of $R^3$ and $R^4$ is an optionally substituted group selected from indolyl, benzimidazolyl, and indazolyl. In some embodiments, at least one of $R^3$ and $R^4$ is an unsubstituted group selected from indolyl, benzimidazolyl, and indazolyl. In some embodiments, at least one of $R^3$ and $R^4$ is a substituted group selected from indolyl, benzimidazolyl, and indazolyl.

In certain embodiments, at least one of $R^3$ and $R^4$ is an optionally substituted group selected from

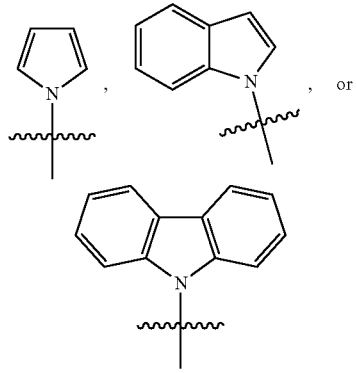

wherein each $\xi$ represents the point of attachment to the metal. In some embodiments, at least one of $R^3$ and $R^4$ is an unsubstituted group selected from

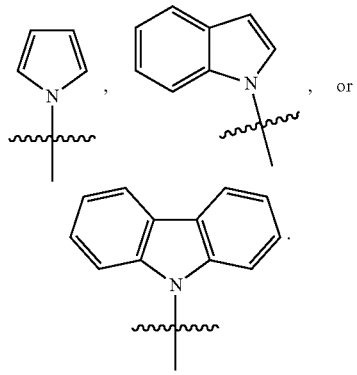

In some embodiments, at least one of $R^3$ and $R^4$ is a substituted group selected from

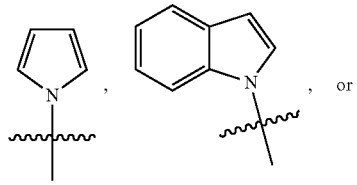

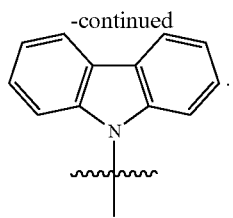

In some embodiments, at least one of $R^3$ and $R^4$ is —OR wherein R is as defined above or described herein. In some embodiments, at least one of $R^3$ and $R^4$ is —OR wherein R is hydrogen. In some embodiments, at least one of $R^3$ and $R^4$ is —OR wherein R is an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, at least one of $R^3$ and $R^4$ is —OR wherein R is an optionally substituted $C_{1-20}$ aliphatic. In some embodiments, at least one of $R^3$ and $R^4$ is —OR wherein R is an optionally substituted $C_{1-20}$ heteroaliphatic having 1-3 heteroatoms independently selected from nitrogen, oxygen, or sulfur. In some embodiments, at least one of $R^3$ and $R^4$ is —OR wherein R is an optionally substituted phenyl. In some embodiments, at least one of $R^3$ and $R^4$ is —OR wherein R is an optionally substituted 3-7 membered saturated or partially unsaturated carbocyclic ring. In some embodiments, at least one of $R^3$ and $R^4$ is —OR wherein R is an optionally substituted 8-10 membered bicyclic saturated, partially unsaturated or aryl ring. In some embodiments, at least one of $R^3$ and $R^4$ is —OR wherein R is an optionally substituted 5-6 membered monocyclic heteroaryl ring having 1-4 heteroatoms independently selected from nitrogen, oxygen, or sulfur. In some embodiments, at least one of $R^3$ and $R^4$ is —OR wherein R is an optionally substituted 4-7 membered saturated or partially unsaturated heterocyclic ring having 1-3 heteroatoms independently selected from nitrogen, oxygen, or sulfur. In some embodiments, at least one of $R^3$ and $R^4$ is —OR wherein R is an optionally substituted 7-10 membered bicyclic saturated or partially unsaturated heterocyclic ring having 1-5 heteroatoms independently selected from nitrogen, oxygen, or sulfur. In some embodiments, at least one of $R^3$ and $R^4$ is —OR wherein R is an optionally substituted 8-14 membered bicyclic or tricyclic heteroaryl ring having 1-5 heteroatoms independently selected from nitrogen, oxygen, or sulfur.

In certain embodiments, at least one of $R^3$ and $R^4$ is —OR wherein R is an optionally substituted phenyl. In some embodiments, at least one of $R^3$ and $R^4$ is phenoxide. In certain embodiments, at least one of $R^3$ and $R^4$ is —OR wherein R is a substituted phenyl. In certain embodiments, at least one of $R^3$ and $R^4$ is —OR wherein R is a phenyl substituted with one or more optionally substituted alkyl groups. In certain embodiments, at least one of $R^3$ and $R^4$ is —OR wherein R is 2,6 di-substituted phenyl with two optionally substituted alkyl substituents. In certain embodiments, at least one of $R^3$ and $R^4$ is —OR wherein R is 2, 4, 6 tri-substituted phenyl with three optionally substituted alkyl substituents. In certain embodiments, at least one of $R^3$ and $R^4$ is —OR wherein R is a phenyl substituted with one or more optionally substituted aryl groups. In certain embodiments, at least one of $R^3$ and $R^4$ is —OR wherein R is 2,6 di-substituted phenyl with two optionally substituted aryl substituents. In certain embodiments, at least one of $R^3$ and $R^4$ is —OR wherein R is 2, 4, 6 tri-substituted phenyl with three optionally substituted aryl substituents. In certain embodiments, at least one of $R^3$ and $R^4$ is —OR wherein R is a phenyl substituted with one or more optionally substituted phenyl groups. In certain embodiments, at least one of $R^3$ and $R^4$ is —OR wherein R is 2,6 di-substituted phenyl with two optionally substituted phenyl substituents. In certain embodiments, at least one of $R^3$ and $R^4$ is —OR wherein R is 2, 4, 6 tri-substituted phenyl with three optionally substituted phenyl substituents. In certain embodiments at least one of $R^3$ and $R^4$ is O-2,6-dimesitylphenoxide (OHMT). In certain embodiments at least one of $R^3$ and $R^4$ is O-2,6-(2,4,6-triisopropylphenyl)$_2$C6H$_3$ (OHIPT). In certain embodiments at least one of $R^3$ and $R^4$ is 2,6-pentafluorophenylphenoxide (DFTO or decafluoroterphenoxide).

In certain embodiments at least one of $R^3$ and $R^4$ is $O(R)_2$ wherein each R is independently as defined above or described herein.

In certain embodiments at least one of $R^3$ and $R^4$ is $O(R)_2$ wherein each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments at least one of $R^3$ and $R^4$ is $O(R)_2$ wherein two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur.

In certain embodiments, at least one of $R^3$ and $R^4$ is independently $N(R)_3$ wherein each R is independently as defined above or described herein. In certain embodiments, at least one of $R^3$ and $R^4$ is independently $N(R)_3$ wherein each R is independently hydrogen or an optionally substituted group selected from $C_{1-20}$ aliphatic, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic or tricyclic heteroaryl ring having 1-5 heteroatoms independently selected from nitrogen, oxygen, or sulfur. In some embodiments, one R group is hydrogen and the other two is independently an optionally substituted group selected from phenyl, napthyl, cyclohexyl, pyridyl, pyrimidinyl, cyclopentyl, methyl, ethyl, propyl, or butyl.

In certain embodiments, at least one of $R^3$ and $R^4$ is independently $N(R)_3$, wherein the two or three R groups are taken together with the nitrogen atom to form an optionally substituted 3-12 membered saturated, partially unsaturated, or aryl ring having 0-5 additional heteroatoms not including the N atom from $N(R)_3$ independently selected from nitrogen, oxygen, or sulfur. In some embodiments, two or three R groups are taken together with the nitrogen to form an optionally substituted 5-membered heteroaryl ring having 1-3 nitrogen atoms. Such rings include optionally substituted pyrrole, pyrazole, imidazole, and triazole.

In some embodiments, at least one of $R^3$ and $R^4$ is independently a phosphorus-containing ligand. In some embodiments, at least one of $R^3$ and $R^4$ is independently phosphorous-containing ligand capable of coordinating with W via the phosphorus atom. In some embodiments, at least one of $R^3$ and $R^4$ is independently —$P(R')_2$, $P(R')_3$, —$P(O)(R')_2$, $P(O)(R')_3$ wherein:

each R' is independently halogen, —R, —OR, —$N(R)_2$, or two or three R' are taken together with the phosphorus to form an optionally substituted 3-20 membered ring with 0-10 additional heteroatoms not including the phosphorus atom from —$P(R')_2$, $P(R')_3$, —$P(O)(R')_2$, or $P(O)(R')_3$, independently selected from nitrogen, oxygen, sulfur, or phosphorus; and each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

In some embodiments, at least one of $R^3$ and $R^4$ is independently $P(R')_3$, wherein each R' is independently as defined above and described herein. In some embodiments, at least one of $R^3$ and $R^4$ is independently $P(R')_3$, wherein each R' is R and wherein R is as defined above and described herein. In some embodiments, at least one of $R^3$ and $R^4$ is independently $P(R')_3$, wherein each R' is an optionally substituted group selected from hydrogen, $C_{1-20}$ aliphatic, phenyl, or ferrocene.

In some embodiments, at least one of $R^3$ or $R^4$ is partially dissociated.

In some embodiments, $R^3$ is halogen, or —OR wherein R is as defined above and described herein. In some embodiments, $R^3$ is halogen. In some embodiments, $R^3$ is —OR wherein R is as defined above and described herein. In some embodiments, $R^3$ is —OR wherein R is hydrogen. In some embodiments, $R^3$ is —OR wherein R is an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, $R^3$ is —OR wherein R is an optionally substituted $C_{1-20}$ aliphatic. In some embodiments, $R^3$ is —OR wherein R is an optionally substituted $C_{1-20}$ heteroaliphatic having 1-3 heteroatoms independently selected from nitrogen, oxygen, or sulfur. In some embodiments, $R^3$ is —OR wherein R is an optionally substituted phenyl. In some embodiments, $R^3$ is —OR wherein R is an optionally substituted 3-7 membered saturated or partially unsaturated carbocyclic ring. In some embodiments, $R^3$ is —OR wherein R is an optionally substituted 8-10 membered bicyclic saturated, partially unsaturated or aryl ring. In some embodiments, $R^3$ is —OR wherein R is an optionally substituted 5-6 membered monocyclic heteroaryl ring having 1-4 heteroatoms independently selected from nitrogen, oxygen, or sulfur. In some embodiments, $R^3$ is —OR wherein R is an optionally substituted 4-7 membered saturated or partially unsaturated heterocyclic ring having 1-3 heteroatoms independently selected from nitrogen, oxygen, or sulfur. In some embodiments, $R^3$ is —OR wherein R is an optionally substituted 7-10 membered bicyclic saturated or partially unsaturated heterocyclic ring having 1-5 heteroatoms independently selected from nitrogen, oxygen, or sulfur. In some embodiments, $R^3$ is —OR wherein R is an optionally substituted 8-14 membered bicyclic or tricyclic heteroaryl ring having 1-5 heteroatoms independently selected from nitrogen, oxygen, or sulfur.

In some embodiments, $R^3$ is —OR wherein R is an optionally substituted phenyl. In some embodiments, $R^3$ is phenoxide. In certain embodiments, $R^3$ is —OR wherein R is a substituted phenyl. In certain embodiments, $R^3$ is —OR wherein R is a phenyl substituted with one or more optionally substituted alkyl groups. In certain embodiments, $R^3$ is —OR wherein R is 2,6 di-substituted phenyl with two optionally substituted alkyl substituents. In certain embodiments, $R^3$ is —OR wherein R is 2, 4, 6 tri-substituted phenyl with three optionally substituted alkyl substituents. In certain embodiments, $R^3$ is —OR wherein R is a phenyl substituted with one or more optionally substituted aryl groups. In certain embodiments, $R^3$ is —OR wherein R is 2,6 di-substituted phenyl with two optionally substituted aryl substituents. In certain embodiments, $R^3$ is —OR wherein R is 2, 4, 6 tri-substituted phenyl with three optionally substituted aryl substituents. In certain embodiments, $R^3$ is —OR wherein R is a phenyl substituted with one or more optionally substituted phenyl groups. In certain embodiments, $R^3$ is —OR wherein R is 2,6 di-substituted phenyl with two optionally substituted phenyl substituents. In certain embodiments, $R^3$ is —OR wherein R is 2, 4, 6 tri-substituted phenyl with three optionally substituted phenyl substituents. In certain embodiments $R^3$ is O-2,6-dimesitylphenoxide (OHMT). In certain embodiments $R^3$ is O-2,6-(2,4,6-triisopropylphenyl)$_2$C6H$_3$ (OHIPT). In some embodiments, $R^3$ is not —O-2,6-Ph$_2$C6H$_3$. In some embodiments, $R^3$ is 2,6-pentafluorophenylphenoxide (DFTO or decafluoroterphenoxide).

In some embodiments, $R^3$ is an optionally substituted group selected from:

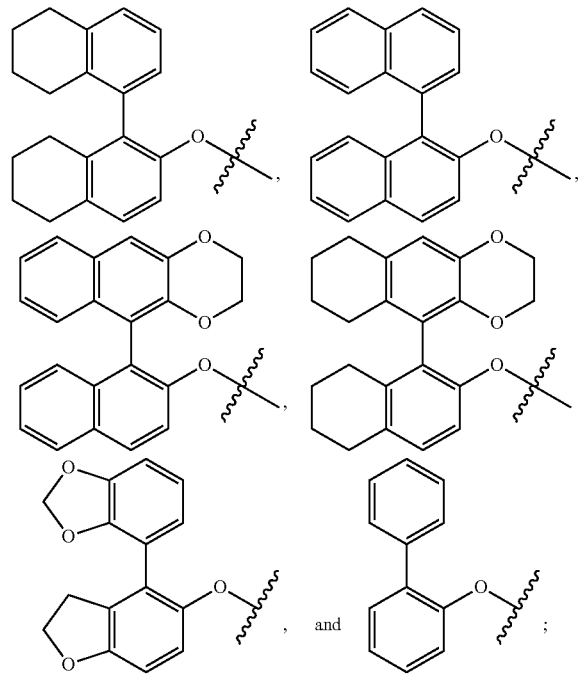

wherein each ⌇ represents the point of attachment to W. In other embodiments, $R^3$ is an optionally substituted

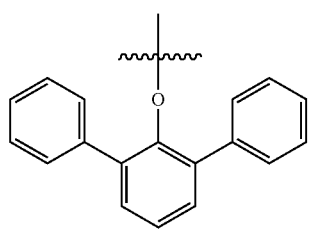 [SMILES: *Oc1c(-c2ccccc2)cccc1-c1ccccc1]

moiety. In some embodiments, $R^3$ is optionally substituted with one or more electron-withdrawing groups. In some embodiments, $R^3$ is optionally substituted with one or more halogen. In some embodiments, $R^3$ is optionally substituted with one or more —F. In some embodiments, $R^3$ is optionally substituted with one or more —Cl. In some embodiments, $R^3$ is optionally substituted with one or more —Br. In some embodiments, $R^3$ is optionally substituted with one or more —I.

Exemplary $R^3$ groups are depicted below, wherein each ⌇ represents the point of attachment to the metal:

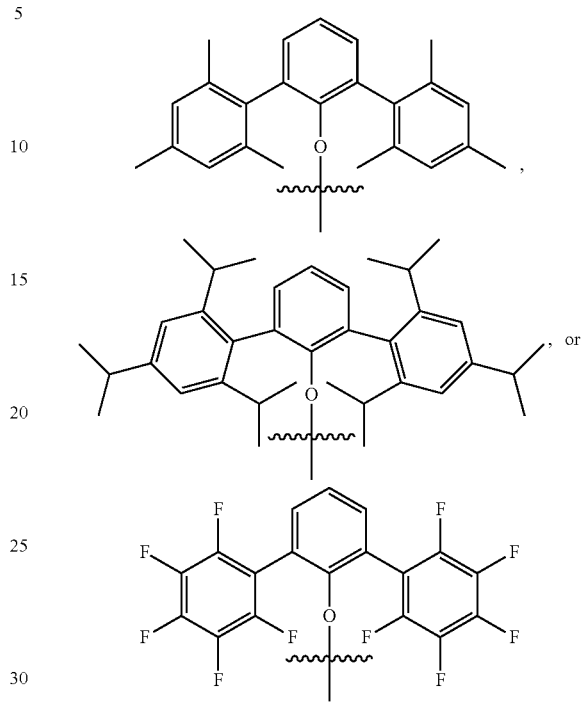

In some embodiments, $R^4$ is halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur, wherein each R is independently as defined above and described herein.

In some embodiments, $R^4$ is —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur, wherein each R is independently as defined above and described herein.

In certain embodiments, $R^4$ is halogen. In some embodiments, $R^4$ is —$N(R)_2$. In some embodiments, $R^4$ is an optionally substituted 5-6 membered monocyclic heteroaryl ring having at least one nitrogen and 0-3 additional heteroatoms independently selected from nitrogen, oxygen, or sulfur. In some embodiments, $R^4$ is an optionally substituted 4-7 membered saturated or partially unsaturated heterocyclic ring having at least one nitrogen and 0-2 additional heteroatoms independently selected from nitrogen, oxygen, or sulfur. In some embodiments, $R^4$ is an optionally substituted 7-10 membered bicyclic saturated or partially unsaturated heterocyclic ring having at least one nitrogen and 0-4 additional heteroatoms independently selected from nitrogen, oxygen, or sulfur. In some embodiments, $R^4$ is an optionally substituted 8-10 membered bicyclic heteroaryl ring having at least one nitrogen and 0-4 additional heteroatoms independently selected from nitrogen, oxygen, or sulfur.

In certain embodiments, at least one of $R^3$ and $R^4$ is halogen. In some embodiments, none of $R^3$ and $R^4$ is halogen.

In certain embodiments, $R^4$ is —$N(R)_2$. In some embodiments, $R^4$ is —$N(R)_2$ wherein each R is hydrogen. In some embodiments, $R^4$ is —$N(R)_2$ wherein only one R is hydrogen. In some embodiments, $R^4$ is —$N(R)_2$ wherein neither R is hydrogen.

In other embodiments, $R^4$ is —$N(R)_2$, wherein the two R groups are taken together with the nitrogen to form an optionally substituted 3-8 membered saturated, partially unsaturated, or aryl ring having 0-3 additional heteroatoms not including the N atom from $N(R)_2$ independently selected from nitrogen, oxygen, or sulfur, wherein $R^4$ is coordinated to W via a nitrogen. In some embodiments, the two R groups are taken together with the nitrogen to form an optionally substituted 5-membered heteroaryl ring having 0-3 additional nitrogen atoms not including the N atom from $N(R)_2$. Such rings include optionally substituted pyrrol-1-yl, pyrazol-1-yl, imidazol-1-yl, and triazol-1-yl. In some embodiments, such rings are unsubstituted pyrrol-1-yl, pyrazol-1-yl, imidazol-1-yl, and triazol-1-yl.

In some embodiments, $R^4$ is an optionally substituted 5-6 membered monocyclic heteroaryl ring having at least one nitrogen and 0-3 additional heteroatoms independently selected from nitrogen, oxygen, or sulfur. In some embodiments, $R^4$ is an optionally substituted group selected from pyrrolyl, pyrazolyl, imidazolyl, triazolyl, oxazolyl, isoxazoly, oxadiazoyl, thiazolyl, and thiazolyl. In some embodiments, $R^4$ is an unsubstituted group selected from pyrrolyl, pyrazolyl, imidazolyl, triazolyl, oxazolyl, isoxazoly, oxadiazoyl, thiazolyl, and thiazolyl. In some embodiments, $R^4$ is a substituted group selected from pyrrolyl, pyrazolyl, imidazolyl, triazolyl, oxazolyl, isoxazoly, oxadiazoyl, thiazolyl, and thiazolyl. In some embodiments, $R^4$ is unsubstituted pyrrolyl. In some embodiments, $R^4$ is substituted pyrrolyl.

In other embodiments, $R^4$ is an optionally substituted 8-10 membered bicyclic heteroaryl ring having at least one nitrogen and 0-4 additional heteroatoms independently selected from nitrogen, oxygen, or sulfur. In some embodiments, $R^4$ is an optionally substituted group selected from indolyl, benzimidazolyl, and indazolyl. In some embodiments, $R^4$ is an unsubstituted group selected from indolyl, benzimidazolyl, and indazolyl. In some embodiments, $R^4$ is a substituted group selected from indolyl, benzimidazolyl, and indazolyl.

In certain embodiments, the hapticity of $R^4$ is 1. In certain embodiments, the hapticity of $R^4$ is more than 1. In certain embodiments, the hapticity of $R^4$ is 2-8. In certain embodiments, the hapticity of $R^4$ is 2. In certain embodiments, the hapticity of $R^4$ is 3. In certain embodiments, the hapticity of $R^4$ is 4. In certain embodiments, the hapticity of $R^4$ is 5. In certain embodiments, the hapticity of $R^4$ is 6. In certain embodiments, the hapticity of $R^4$ is 7. In certain embodiments, the hapticity of $R^4$ is 8.

In certain embodiments, $R^4$ is an optionally substituted group selected from

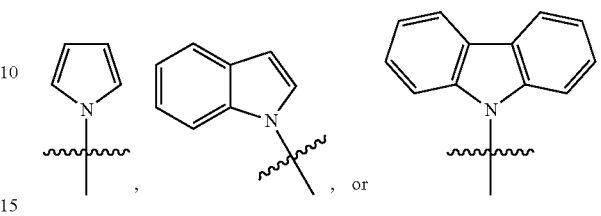

wherein each ⌇ represents the point of attachment to the metal.

In some embodiments, $R^4$ is —OR wherein R is as defined above and described herein. In some embodiments, $R^4$ is —OR wherein R is hydrogen. In some embodiments, $R^4$ is —OR wherein R is an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, $R^4$ is —OR wherein R is an optionally substituted $C_{1-20}$ aliphatic. In some embodiments, $R^4$ is —OR wherein R is an optionally substituted $C_{1-20}$ heteroaliphatic having 1-3 heteroatoms independently selected from nitrogen, oxygen, or sulfur. In some embodiments, $R^4$ is —OR wherein R is an optionally substituted phenyl. In some embodiments, $R^4$ is —OR wherein R is an optionally substituted 3-7 membered saturated or partially unsaturated carbocyclic ring. In some embodiments, $R^4$ is —OR wherein R is an optionally substituted 8-10 membered bicyclic saturated, partially unsaturated or aryl ring. In some embodiments, $R^4$ is —OR wherein R is an optionally substituted 5-6 membered monocyclic heteroaryl ring having 1-4 heteroatoms independently selected from nitrogen, oxygen, or sulfur. In some embodiments, $R^4$ is —OR wherein R is an optionally substituted 4-7 membered saturated or partially unsaturated heterocyclic ring having 1-3 heteroatoms independently selected from nitrogen, oxygen, or sulfur. In some embodiments, $R^4$ is —OR wherein R is an optionally substituted 7-10 membered bicyclic saturated or partially unsaturated heterocyclic ring having 1-5 heteroatoms independently selected from nitrogen, oxygen, or sulfur. In some embodiments, $R^4$ is —OR wherein R is an optionally substituted 8-14 membered bicyclic or tricyclic heteroaryl ring having 1-5 heteroatoms independently selected from nitrogen, oxygen, or sulfur.

In some embodiments, $R^4$ is —OR wherein R is an optionally substituted phenyl. In some embodiments, $R^4$ is phenoxide. In certain embodiments, $R^4$ is —OR wherein R is a substituted phenyl. In certain embodiments, $R^4$ is —OR wherein R is a phenyl substituted with one or more optionally substituted alkyl groups. In certain embodiments, $R^4$ is —OR wherein R is 2,6 di-substituted phenyl with two optionally substituted alkyl substituents. In certain embodiments, $R^4$ is —OR wherein R is 2, 4, 6 tri-substituted phenyl with three optionally substituted alkyl substituents. In certain embodiments, $R^4$ is —OR wherein R is a phenyl substituted with one or more optionally substituted aryl groups. In certain embodiments, $R^4$ is —OR wherein R is 2,6 di-substituted phenyl with two optionally substituted aryl substituents. In certain embodiments, $R^4$ is —OR wherein R is 2, 4, 6 tri-substituted phenyl with three optionally substituted aryl substituents. In certain embodiments, $R^4$ is —OR wherein R is a phenyl substituted with one or more optionally substituted phenyl groups. In certain embodiments, $R^4$ is —OR wherein R is 2,6 di-substituted phenyl with two optionally substituted phenyl substituents. In certain embodiments, $R^4$ is —OR wherein R is 2, 4, 6 tri-substituted phenyl with three optionally substituted phenyl substituents. In certain embodiments $R^4$ is O-2, 6-dimesitylphenoxide (OHMT). In certain embodiments $R^4$ is O-2,6-(2,4,6-triisopropylphenyl)$_2$C6H$_3$ (OHIPT). In some embodiments, $R^4$ is not —O-2,6-Ph$_2$C6H$_3$. In some embodiments, $R^4$ is 2,6-pentafluorophenylphenoxide (DFTO or decafluoroterphenoxide).

In some embodiments, $R^4$ is an optionally substituted group selected from:

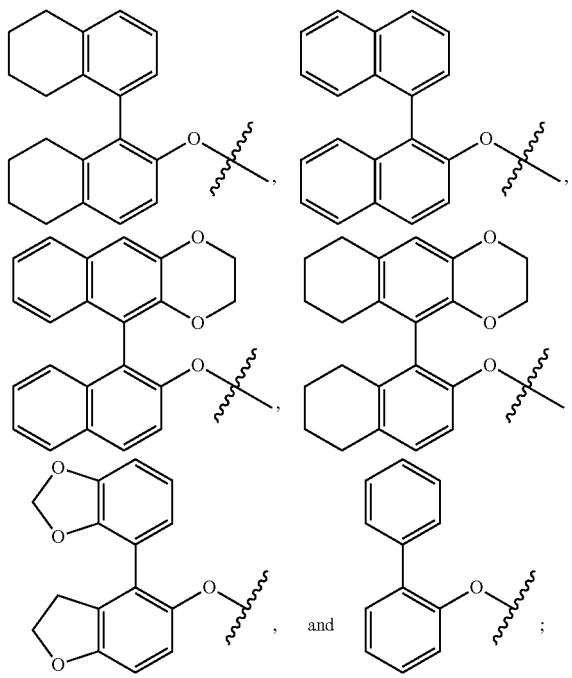

wherein each $\varsigma$ represents the point of attachment to W. In other embodiments, —OR$^4$ is an optionally substituted

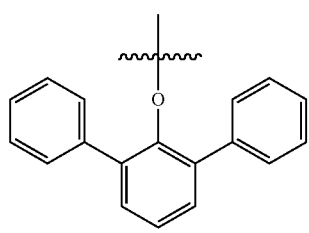 [SMILES: *Oc1c(-c2ccccc2)cccc1-c1ccccc1]

moiety. In some embodiments, $R^3$ is optionally substituted with one or more electron-withdrawing groups. In some embodiments, $R^3$ is optionally substituted with one or more halogen. In some embodiments, $R^3$ is optionally substituted with one or more —F. In some embodiments, $R^3$ is optionally substituted with one or more —Cl. In some embodiments, $R^3$ is optionally substituted with one or more —Br. In some embodiments, $R^3$ is optionally substituted with one or more —I.

Exemplary $R^3$ groups are depicted below, wherein each $\varsigma$ represents the point of attachment to the metal:

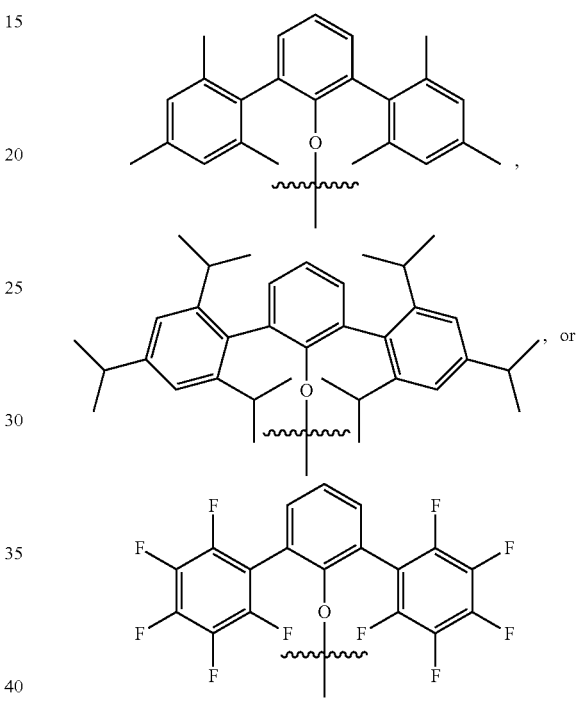

Exemplary $R^4$ groups are depicted below, wherein each $\varsigma$ represents the point of attachment to the metal:

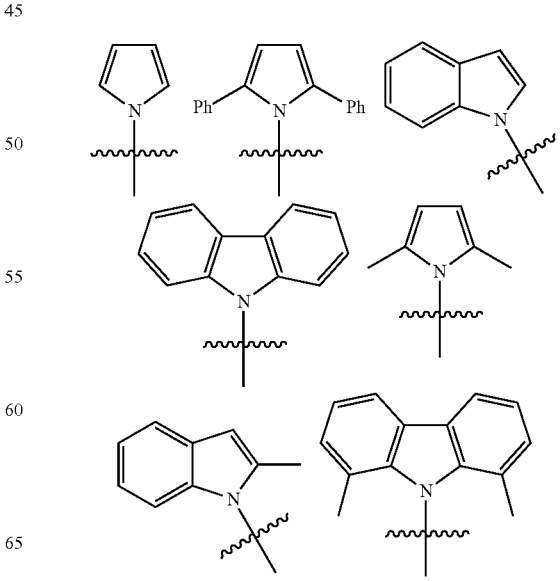

-continued

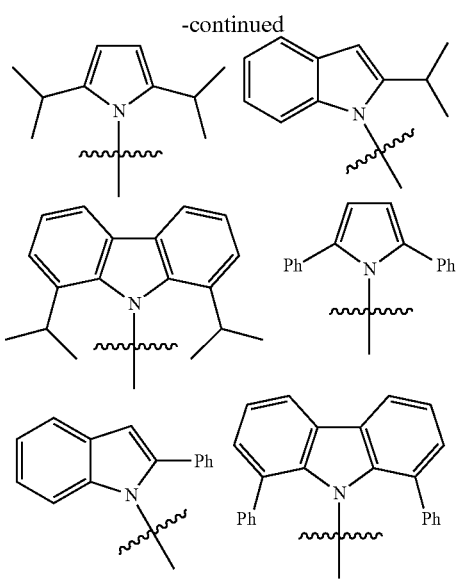

As defined generally above, n is 0, 1, or 2.

In some embodiments, n is 0. In some embodiments, n is 1. In some embodiments, n is 2.

In certain embodiments, n is 0 and the present invention provides a compound of formula II:

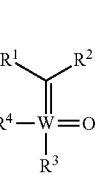
II wherein each of $R^1$, $R^2$, $R^3$, and $R^4$ is as defined above and described in embodiments herein, both singly and in combination.

In some embodiments, the present invention provides a compound of formula II-a, below:

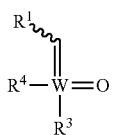
II-a wherein each of $R^1$, $R^3$, and $R^4$ is as defined above and described in embodiments herein, both singly and in combination.

In certain embodiments, n is 1 and the present invention provides a compound of formula III:

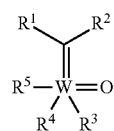
III wherein each of $R^1$, $R^2$, $R^3$, $R^4$, and $R^5$ is as defined above and described in embodiments herein, both singly and in combination.

In some embodiments, the present invention provides a compound of formula III-a:

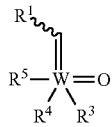
III-a wherein each of $R^1$, $R^3$, $R^4$, and $R^5$ is as defined above and described in embodiments herein, both singly and in combination.

In certain embodiments, n is 2 and the present invention provides a compound of formula IV:

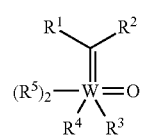
IV wherein each of $R^1$, $R^2$, $R^3$, $R^4$, and $R^5$ is as defined above and described in embodiments both singly and in combination.

In certain embodiments, the present invention provides a compound of formula IV-a:

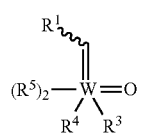
IV-a wherein each of $R^1$, $R^3$, $R^4$, and $R^5$ is as defined above and described in embodiments herein, both singly and in combination.

As defined generally above, each $R^5$ is independently a monodentate ligand, or two $R^5$ are taken together with their intervening atoms to form an optionally substituted bidentate group. In some embodiments, each $R^5$ is independently halogen, nitrogen-containing ligand, oxygen-containing ligand, or phosphorus-containing ligand. In some embodiments, two $R^5$ are taken together with their intervening atoms to form an optionally substituted bidentate group. One of ordinary skill in the art will appreciate that $R^5$ can be any suitable ligand capable of coordinating with W. In some embodiments, such ligands are depicted herein.

In certain embodiments, the hapticity of $R^5$ is 1. In certain embodiments, the hapticity of $R^5$ is more than 1. In certain embodiments, the hapticity of $R^5$ is 2-8. In certain embodiments, the hapticity of $R^5$ is 2. In certain embodiments, the hapticity of $R^5$ is 3. In certain embodiments, the hapticity of $R^5$ is 4. In certain embodiments, the hapticity of $R^5$ is 5. In certain embodiments, the hapticity of $R^5$ is 6. In certain embodiments, the hapticity of $R^5$ is 7. In certain embodiments, the hapticity of $R^5$ is 8.

In some embodiments, each $R^5$ is independently nitrogen-containing ligand capable of coordinating with W via the nitrogen atom. Accordingly, in some embodiments, each $R^5$ is independently —N(R)$_2$, —NRC(O)R, —NRC(O)OR, —NRC(O)N(R)$_2$, —NRSO$_2$R, —NRSO$_2$N(R)$_2$, —NROR, N(R)$_3$, a 5-6 membered monocyclic heteroaryl ring having at least one nitrogen atom and 0-3 additional heteroatoms independently selected from nitrogen, oxygen, or sulfur, a 4-7 membered saturated or partially unsaturated heterocyclic ring having at least one nitrogen atom and 0-2 additional heteroatoms independently selected from nitrogen, oxygen, or sulfur, a 7-10 membered bicyclic saturated or partially unsaturated heterocyclic ring having at least one nitrogen atom and 0-4 additional heteroatoms independently selected from nitrogen, oxygen, or sulfur, or an 8-14 membered bicyclic or tricyclic heteroaryl ring having at least one nitrogen atom and 0-4 additional heteroatoms independently selected from nitrogen, oxygen, or sulfur, or two $R^5$ are taken together with their intervening atoms to form an optionally substituted bidentate group, wherein each R is independently as defined above or described herein.

In some embodiments, at least one of $R^5$ is independently selected from an optionally substituted 6-membered heteroaryl ring having 1-3 nitrogens. Such $R^5$ includes optionally substituted pyridine, pyrimidine, or triazine groups.

In certain embodiments, each $R^5$ is independently optionally substituted pyridine. In some embodiments, each $R^5$ is independently optionally substituted pyridine.

In other embodiments, each $R^5$ is independently selected from an optionally substituted 5-membered heteroaryl ring having one nitrogen and 0-2 additional heteroatoms independently selected from nitrogen, oxygen, or sulfur. Such $R^5$ groups include optionally substituted pyrrole, pyrazole, imidazole, triazole, oxazole, isoxazole, oxadiazole, thiazole, and thiadiazole rings.

In some embodiments, at least one of $R^5$ is independently —N(R)$_2$, —NHC(O)R, —NHC(O)OR, —NHC(O)N(R)$_2$, N(R)$_3$, or —NHSO$_2$R wherein each R is independently as defined above or described herein. In some embodiments, at least one of $R^5$ is —N(R)$_2$ wherein each R is independently as defined above or described herein.

In certain embodiments, each $R^5$ is independently —N(R)$_2$ wherein each R is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In certain embodiments, each $R^5$ is independently —N(R)$_2$, wherein the two R groups are taken together with the nitrogen atom to form an optionally substituted 3-8 membered saturated, partially unsaturated, or aryl ring having 0-3 additional heteroatoms not including the N atom from N(R)$_2$ independently selected from nitrogen, oxygen, or sulfur. In some embodiments, the two R groups are taken together with the nitrogen to form an optionally substituted 5-membered heteroaryl ring having 1-3 nitrogen atoms. Such rings include optionally substituted pyrrol-1-yl, pyrazol-1-yl, imidazol-1-yl, and triazol-1-yl.

In certain embodiments, each $R^5$ is independently N(R)$_3$ wherein each R is independently as defined above or described herein. In certain embodiments, each $R^5$ is independently N(R)$_3$ wherein each R is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In certain embodiments, each $R^5$ is independently N(R)$_3$, wherein the two or three R groups are taken together with the nitrogen atom to form an optionally substituted 3-12 membered saturated, partially unsaturated, or aryl ring having 0-5 additional heteroatoms not including the N atom from N(R)$_3$ independently selected from nitrogen, oxygen, or sulfur. In some embodiments, two or three R groups are taken together with the nitrogen to form an optionally substituted 5-membered heteroaryl ring having 1-3 nitrogen atoms. Such rings include optionally substituted pyrrole, pyrazole, imidazole, and triazole.

In certain embodiments, each $R^5$ is independently —NHC(O)R wherein R is as defined above or described herein. In some embodiments, each $R^5$ is independently —NHC(O)R, wherein R is an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, R is an optionally substituted group selected from phenyl, napthyl, cyclohexyl, pyridyl, pyrimidinyl, cyclopentyl, methyl, ethyl, propyl, or butyl.

In some embodiments, two $R^5$ are taken together with their intervening atoms to form an optionally substituted bidentate moiety. In certain embodiments, two $R^5$ are taken together to form optionally substituted bipyridyl. In certain embodiments, two $R^5$ are taken together to form:

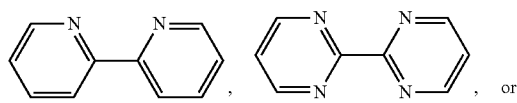

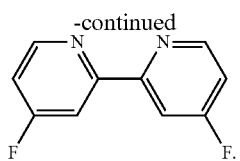

In some embodiments, two $R^5$ are taken together with their intervening atoms to form a bidentate optionally substituted bicyclic or tricyclic heteroaryl ring having 1-3 heteroatoms independently selected from nitrogen, oxygen, or sulfur. In certain embodiments, two $R^5$ are taken together to form optionally substituted phenanthroline. In certain embodiments, two $R^5$ are taken together to form

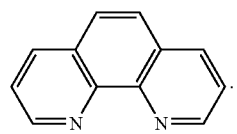 [SMILES: c1cnc2c(c1)ccc1cccnc12]

In some embodiments, each $R^5$ is independently oxygen-containing ligand. In some embodiments, each $R^5$ is independently oxygen-containing ligand capable of coordinating with W via the oxygen atom. In some embodiments, each $R^5$ is independently —OR, $O(R)_2$, a 5-6 membered monocyclic heteroaryl ring having at least one oxygen atom and 0-3 additional heteroatoms independently selected from nitrogen, oxygen, or sulfur, a 4-7 membered saturated or partially unsaturated heterocyclic ring having at least one oxygen atom and 0-2 additional heteroatoms independently selected from nitrogen, oxygen, or sulfur, a 7-10 membered bicyclic saturated or partially unsaturated heterocyclic ring having at least one oxygen atom and 0-4 additional heteroatoms independently selected from nitrogen, oxygen, or sulfur, or an 8-14 membered bicyclic or tricyclic heteroaryl ring having at least one oxygen atom and 0-4 additional heteroatoms independently selected from nitrogen, oxygen, or sulfur, or two $R^5$ are taken together with their intervening atoms to form an optionally substituted bidentate group, wherein each R is independently as defined above or described herein.

In certain embodiments, each $R^5$ is independently —OR, wherein each R is independently as defined above or described herein. In certain embodiments, each $R^5$ is independently —OR, wherein each R is independently hydrogen or an optionally substituted group selected from $C_{1-20}$ aliphatic, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In certain embodiments, each $R^5$ is independently $O(R)_2$, wherein each R is independently as defined above or described herein. In certain embodiments, each $R^5$ is independently $O(R)_2$, wherein each R is independently hydrogen or an optionally substituted group selected from $C_{1-20}$ aliphatic, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In certain embodiments, each $R^5$ is independently $O(R)_2$, wherein the two R groups are taken together with the oxygen atom to form an optionally substituted 3-8 membered saturated, partially unsaturated, or aryl ring having 0-3 additional heteroatoms not including the oxygen atom from $O(R)_2$ independently selected from nitrogen, oxygen, or sulfur.

In some embodiments, each $R^5$ is independently a phosphorus-containing ligand. In some embodiments, each $R^5$ is independently a phosphorous-containing ligand capable of coordinating with W via the phosphorus atom. In some embodiments, each $R^5$ is independently —$P(R')_2$, $P(R')_3$, —$P(O)(R')_2$, $P(O)(R')_3$ wherein:

each R' is independently halogen, —R, —OR, —$N(R)_2$, or two or three R' are taken together with the phosphorus to form an optionally substituted 3-20 membered ring with 0-10 additional heteroatoms not including the phosphorus atom from —$P(R')_2$, $P(R')_3$, —$P(O)(R')_2$, or $P(O)(R')_3$, independently selected from nitrogen, oxygen, sulfur, or phosphorus; and each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur.

In some embodiments, each $R^5$ is independently $P(R')_3$, wherein each R' is independently as defined above and described herein. In some embodiments, each $R^5$ is independently $P(R')_3$, wherein each R' is R and wherein R is as defined above and described herein. In some embodiments, each $R^5$ is independently $P(R')_3$, wherein each R' is an optionally substituted group selected from hydrogen, $C_{1-20}$ aliphatic, phenyl, or ferrocene.

In some embodiments, one or two $R^5$ are partially dissociated.

Exemplary monodentate and bidentate $R^5$ groups are depicted below:

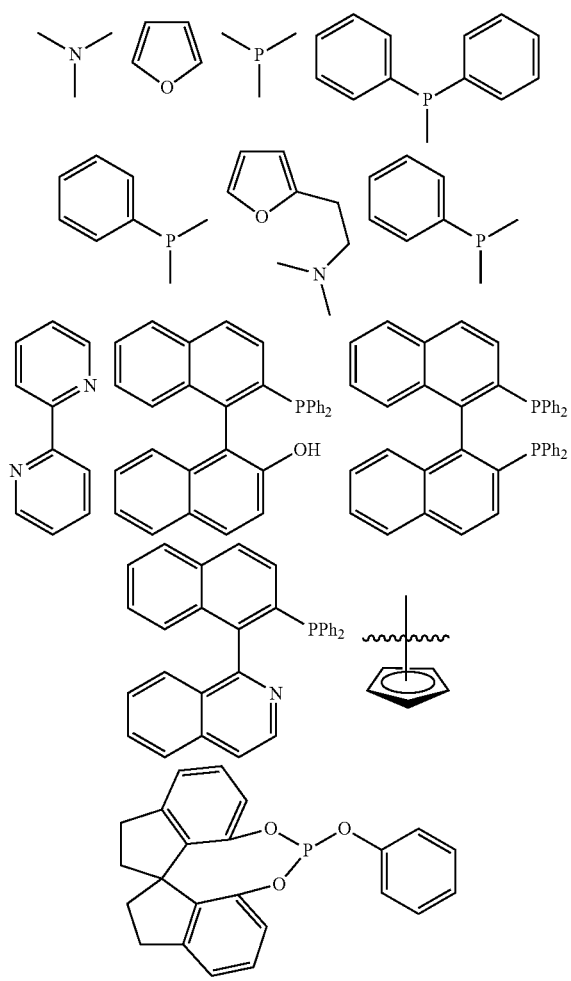

In some embodiments, two or more of $R^1$, $R^2$, $R^3$, $R^4$ and $R^5$ may be taken together with their intervening atoms to form an optionally substituted polydentate ligand. In some embodiments, two or more of $R^1$, $R^3$, $R^4$ and $R^5$ may be taken together with their intervening atoms to form an optionally substituted polydentate ligand. In some embodiments, two or more of $R^1$, $R^2$, $R^3$ and $R^4$ may be taken together with their intervening atoms to form an optionally substituted polydentate ligand. In some embodiments, two or more of $R^3$, $R^4$ and $R^5$ may be taken together with their intervening atoms to form an optionally substituted polydentate ligand. In some embodiments, $R^3$ and $R^4$ are taken together with their intervening atoms to form an optionally substituted polydentate ligand.

As defined general above, each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur.

In some embodiments, R is hydrogen. In some embodiments, R is not hydrogen.

In some embodiments, R is optionally substituted $C_{1-20}$ aliphatic. In some embodiments, R is $C_{1-20}$ heteroaliphatic having 1-3 heteroatoms independently selected from nitrogen, oxygen, or sulfur. In some embodiments, R is an optionally substituted a 3-7 membered saturated or partially unsaturated carbocyclic ring. In some embodiments, R is an optionally substituted 8-10 membered bicyclic saturated or partially unsaturated ring. In some embodiments, R is an optionally substituted 4-7 membered saturated or partially unsaturated heterocyclic ring having 1-3 heteroatoms independently selected from nitrogen, oxygen, or sulfur. In some embodiments, R is an optionally substituted 7-10 membered bicyclic saturated or partially unsaturated heterocyclic ring having 1-5 heteroatoms independently selected from nitrogen, oxygen, or sulfur.

In some embodiments, R is independently an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, R is optionally substituted phenyl. In some embodiments, R is phenyl substituted with one or more optionally substituted alkyl groups. In some embodiments, R is 2,6 di-substituted phenyl with two optionally substituted alkyl substituents. In some embodiments, R is 2, 4, 6 tri-substituted phenyl with three optionally substituted alkyl substituents. In some embodiments, R is a phenyl substituted with one or more optionally substituted aryl groups. In some embodiments, R is a phenyl substituted with one or more optionally substituted phenyl groups. In some embodiments, R is 2,6 di-substituted phenyl with two optionally substituted aryl substituents. In some embodiments, R is 2, 4, 6 tri-substituted phenyl with three optionally substituted aryl substituents. In some embodiments, R is a phenyl substituted with one or more optionally substituted phenyl groups. In some embodiments, R is 2,6 di-substituted phenyl with two optionally substituted phenyl substituents. In some embodiments, R is 2, 4, 6 tri-substituted phenyl with three optionally substituted phenyl substituents.

In some embodiments, R is optionally substituted

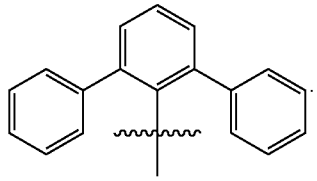 [SMILES: *c1c(-c2ccccc2)cccc1-c1ccccc1]

In some embodiments, R is optionally substituted with one or more electron-withdrawing groups. In some embodiments, R is optionally substituted with one or more halogen. In some embodiments, R is optionally substituted with one or more —F. In some embodiments, R is optionally substituted with one or more —Cl. In some embodiments, R is optionally substituted with one or more —Br. In some embodiments, R is optionally substituted with one or more —I. In some embodiments, R is 2,6-dimesitylphenyl (HMT). In some embodiments, R is 2,6-(2,4,6-triisopropylphenyl)$_2$C6H$_3$ (HIPT). In some embodiments, R is 2,6-pentafluorophenylphenoxide (DFT).

In some embodiments, R is an optionally substituted 8-10 membered aryl ring. In some embodiments, R is a 5-6 membered monocyclic heteroaryl ring having 1-4 heteroatoms independently selected from nitrogen, oxygen, or sulfur. In some embodiments, R is an optionally substituted 8-10 membered bicyclic heteroaryl ring having 1-5 heteroatoms independently selected from nitrogen, oxygen, or sulfur.

In some embodiments, R is an optionally substituted group selected from:

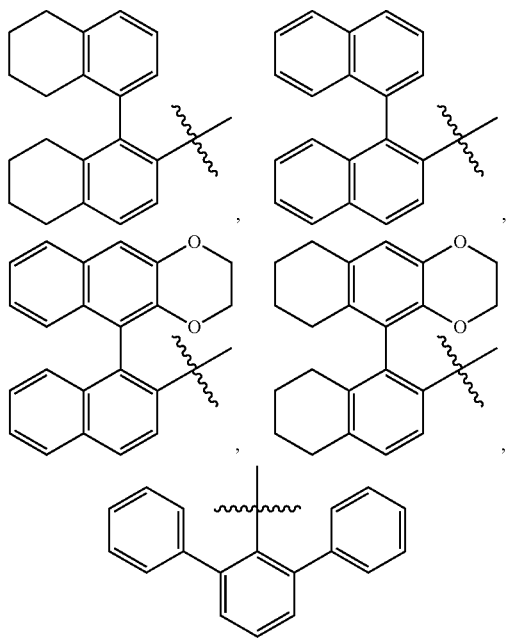

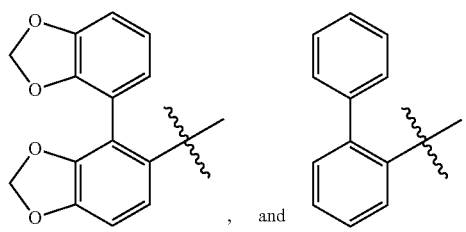

Exemplary optional substituents, as described above and herein, include but are not limited to alkyl, halogen, —OSiR$_3$ groups.

In some embodiments, two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur. In some embodiments, two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur. In some embodiments, two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur. In some embodiments, two R groups are taken together with the nitrogen to form an optionally substituted 5-membered heteroaryl ring having 0-3 additional nitrogen atoms not including the N atom from —N(R)$_2$. Such rings include optionally substituted pyrrol-1-yl, pyrazol-1-yl, imidazol-1-yl, and triazol-1-yl. In some embodiments, such rings are unsubstituted pyrrol-1-yl, pyrazol-1-yl, imidazol-1-yl, and triazol-1-yl.

More embodiments of R include but are not limited to those described in the embodiments of $R^1$, $R^2$, $R^3$, $R^4$, $R^5$, $R^6$, $R^7$, $R^8$, $R^9$, $R^{10}$, $R^{11}$, and $R^{12}$.

Exemplary compounds of formula I are set forth in Table 1, below.

TABLE 1

Exemplary Compounds.

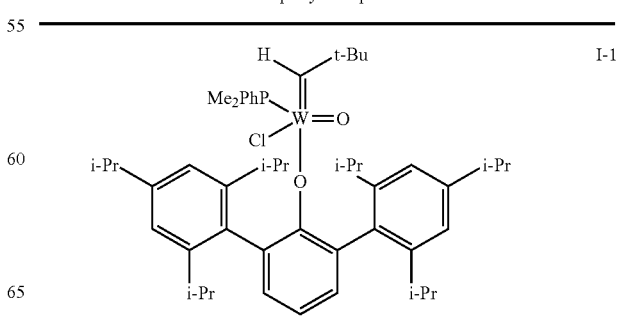

I-1

TABLE 1-continued
Exemplary Compounds.
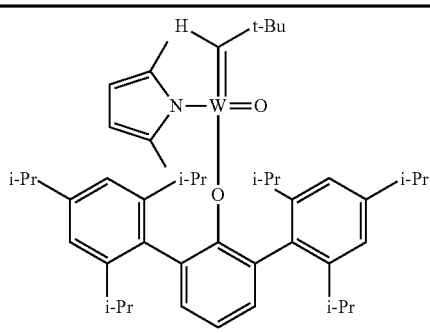
I-2
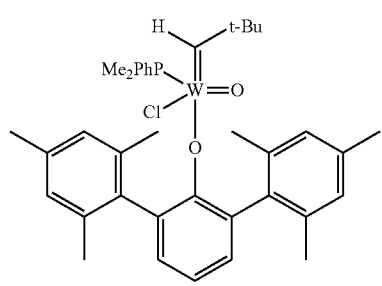
I-3
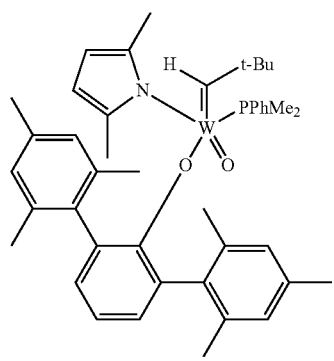
I-4
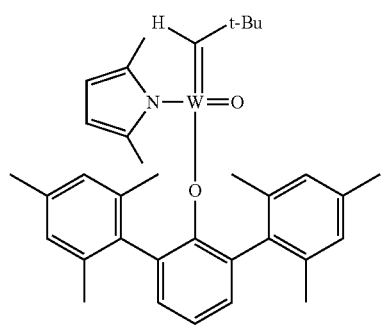
I-5
TABLE 1-continued
Exemplary Compounds.
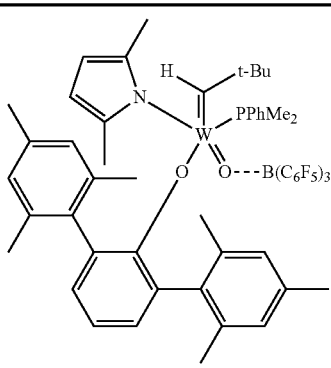
I-6
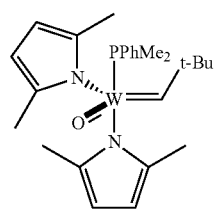
I-7
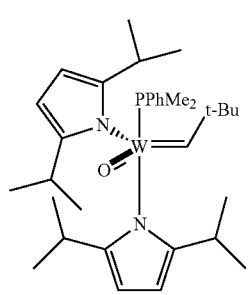
I-8
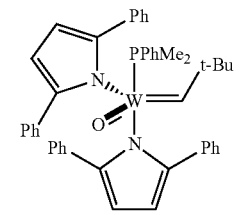
I-9
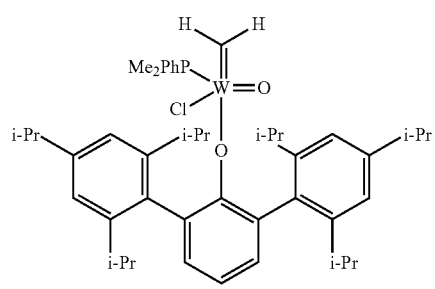
I-10

TABLE 1-continued

Exemplary Compounds.

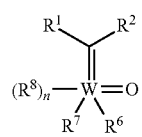

| Compound | ID |
|---|---|
| W(O)(CH—t-Bu)(Ph$_2$Pyr)(OHMT) | I-12 |
| W(O)(CH—t-Bu)(Ph$_2$Pyr)(OHIPT) | I-13 |
| W(O)(CH—t-Bu)[N(C$_6$F$_5$)$_2$](OHMT)(PPhMe$_2$) | I-14 |
| W(O)(CH—t-Bu)(PMe$_3$)$_2$Cl$_2$ | I-15 |
| W(O)(CH—t-Bu)(O-2,6-Ph$_2$C$_6$H$_3$)$_2$(PMe$_3$) | I-16 |
| W(O)(CH—t-Bu)(Cl)(OHIPT) | I-17 |
| W(O)(CH—t-Bu)(PMe$_2$Ph)$_2$Cl$_2$ | I-18 |
| W(O)(CHCMe$_2$Ph)Cl$_2$(PMe$_2$Ph)$_2$ | I-19 |
| W[OB(C$_6$F$_5$)$_3$](CH—t-Bu)(Me$_2$Pyr)(OHMT) | I-20 |
| W(O)(CH—t-Bu)[N—(C$_6$F$_5$)$_2$](OHMT) | I-21 |
| W(O)(CH—t-Bu)(OHMT)$_2$ | I-22 |
| W(O)(CH—t-Bu)(OHIPT)$_2$ | I-23 |
| W(O)(CH—t-Bu)(Me$_2$Pyr)(DFTO)(PPhMe$_2$) | I-24 |
| W(O)(CH—t-Bu)(Me$_2$Pyr)(DFTO) | I-25 |
| W(O)(CHCMe$_2$Ph)(Me$_2$Pyr)(DFTO)(PPhMe$_2$) | I-26 |
| W(O)(CHCMe$_2$Ph)(Me$_2$Pyr)(DFTO) | I-27 |
| W(O)(CH—t-Bu)[N—(C$_6$F$_5$)$_2$](DFTO) | I-28 |
| W(O)(CH—t-Bu)(DFTO)$_2$ | I-29 |

In some embodiments, the present invention provides a compound of formula V:

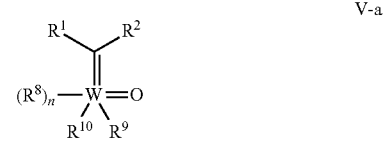

wherein:
each of $R^6$ and $R^7$ is independently halogen, —OR or a phosphorus-containing ligand;
each $R^8$ is independently a monodentate ligand, or two $R^8$ are taken together with their intervening atoms to form an optionally substituted bidentate group; and
each of $R^1$, $R^2$, and n is independently as defined above and described herein.

In some embodiments, n=2.

In some embodiments, $R^8$ is independently a monodentate ligand, or two $R^8$ are taken together with their intervening atoms to form an optionally substituted bidentate group. In some embodiments, $R^8$ is $R^5$, wherein $R^5$ is as defined above and described herein.

In some embodiments, each of $R^6$, $R^7$ and $R^8$ is independently selected from halogen and P(R')$_3$, wherein each R' is independently as defined above or described herein. In some embodiments, each of $R^6$ and $R^7$ is independently halogen and each of $R^8$ is independently P(R')$_3$. In some embodiments, n=2, each of $R^6$ and $R^7$ is independently halogen, and each of $R^8$ is independently P(R')$_3$. In some embodiments, each of $R^6$ and $R^7$ is independently halogen, n is 2, and $R^8$ is PR$_3$, wherein each of R is independently as defined above and described herein.

In some embodiments, a compound of formula V is WO(CHR$^1$R$^2$)(P(R)$_3$)$_2$Cl$_2$, or WO(CHR$^1$R$^2$)(P(R)$_3$)$_2$Br$_2$, wherein each of $R^1$ and $R^2$ is independently as defined above or described herein, and each R is independently an optionally substituted group selected from C$_{1-20}$ aliphatic or phenyl. In some embodiments, a compound of formula V is WO(CH-t-Bu)(PMe$_2$Ph)$_2$Cl$_2$. In some embodiments, a compound of formula V is WO(CH-t-Bu)(PMe$_3$)$_2$Cl$_2$. In some embodiments, a compound of formula V is W(O)(CH-t-Bu)(OHMT)(PMe$_2$Ph)Cl. In some embodiments, a compound of formula V is W(O)(CH-t-Bu)(OHIPT)(PMe$_2$Ph)Cl. In some embodiments, a compound of formula V is W(O)(CH-t-Bu)(DFTO)(PMe$_2$Ph)Cl.

In some embodiments, a compound of formula V has the structure of formula V-a:

$$\underset{R^{10}\ R^9}{(R^8)_n-\underset{\|}{W}=O}\overset{R^1\ R^2}{\diagdown\diagup}$$

V-a wherein:
each of $R^9$ and $R^{10}$ is independently halogen; and
each of $R^1$, $R^2$, $R^8$ and n is independently as defined above and described herein.

In some embodiments, $R^9$ is —F. In some embodiments, $R^9$ is —Cl. In some embodiments, $R^9$ is —Br. In some embodiments, $R^9$ is —I. In some embodiments, $R^{10}$ is —F. In some embodiments, $R^{10}$ is —Cl. In some embodiments, $R^{10}$ is —Br. In some embodiments, $R^{10}$ is —I.

In some embodiments, both $R^9$ and $R^{10}$ are —Cl. In some embodiments, n=2 and both $R^8$ are monodentate phosphine ligands. In some embodiments, n=2 and both $R^8$ are monodentate phosphine ligands having the structure of PR$_3$, wherein each of R is independently as defined above and described herein. In some embodiments, two $R^8$ are taken together to form a bidentate phosphine ligand.

In some embodiments, a compound of structure V or V-a has the structure of W(O)(CHR$^1$)Cl$_2$(R$^8$)$_2$, wherein $R^8$ is a monodentate phosphine ligand having the structure of PR$_3$, wherein each R is independently as defined above and described herein. In some embodiments, PR$_3$ is PMe$_2$Ph. In some embodiments, a compound of structure V or V-a is W(O)(CHt-Bu)Cl$_2$(PMe$_2$Ph)$_2$. In some embodiments, a compound of structure V or V-a is W(O)(CHCMe$_2$Ph)Cl$_2$(PMe$_2$Ph)$_2$.

In some embodiments, the present invention provides a compound of formula V having the structure of formula V-b:

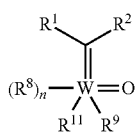

V-b wherein:
$R^{11}$ is —OR; and
each of $R^1$, $R^2$, $R^8$, $R^9$, $R^{10}$, R and n is independently as defined above and described herein.

Exemplary —OR for $R^{11}$ is extensively described in the specification, for example but not limited to the embodiments described for $R^3$ and $R^4$. In some embodiments, $R^1$ is —OR, wherein R is not hydrogen. In some embodiments, $R^1$ is —OR, wherein R is an optionally substituted group selected from $C_{1-20}$ aliphatic or phenyl. In certain embodiments, $R^{11}$ is —OR wherein R is optionally substituted phenyl. In certain embodiments, $R^{11}$ is —OR wherein R is substituted phenyl. In certain embodiments, $R^{11}$ is —OR wherein R is phenyl substituted with one or more optionally substituted alkyl groups. In certain embodiments, $R^{11}$ is —OR wherein R is 2,6 di-substituted phenyl with two optionally substituted alkyl substituents. In certain embodiments, $R^{11}$ is —OR wherein R is 2, 4, 6 tri-substituted phenyl with three optionally substituted alkyl substituents. In certain embodiments, $R^{11}$ is —OR wherein R is a phenyl substituted with one or more optionally substituted aryl groups. In certain embodiments, $R^{11}$ is —OR wherein R is 2,6 di-substituted phenyl with two optionally substituted aryl substituents. In certain embodiments, $R^{11}$ is —OR wherein R is 2, 4, 6 tri-substituted phenyl with three optionally substituted aryl substituents. In certain embodiments, $R^{11}$ is —OR wherein R is a phenyl substituted with one or more optionally substituted phenyl groups. In certain embodiments, $R^{11}$ is —OR wherein R is 2,6 di-substituted phenyl with two optionally substituted phenyl substituents. In certain embodiments, $R^{11}$ is —OR wherein R is 2, 4, 6 tri-substituted phenyl with three optionally substituted phenyl substituents. In certain embodiments $R^{11}$ is O-2,6-dimesitylphenoxide (OHMT). In certain embodiments, $R^{11}$ is O-2,6-(2,4,6-triisopropylphenyl)$_2$C6H$_3$ (OHIPT). In certain embodiments, $R^{11}$ is 2,6-pentafluorophenylphenoxide (DFTO or decafluoroterphenoxide). In some embodiments, —OR is —OHMT. In some embodiments, —OR is OHIPT. In some embodiments, —OR is DFTO. In some embodiments, at least one of $R^3$ and $R^4$ is not —O-2,6-Ph$_2$C6H$_3$.

In some embodiments, a compound of formula V-b is W(O)(CH-t-Bu)(OHMT)(PMe$_2$Ph)Cl. In some embodiments, a compound of formula V-b is W(O)(CH-t-Bu)(OHIPT)(PMe$_2$Ph)Cl. In some embodiments, a compound of formula V-b is W(O)(CH-t-Bu)(DFTO)(PMe$_2$Ph)Cl.

In some embodiments, the present invention provides a compound of formula VI:

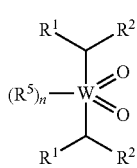

VI wherein each of $R^1$, $R^2$, n and $R^5$ is independently as defined above and described herein. In some embodiments, the two $R^1$ in formula VI are the same. In some embodiments, the two $R^2$ in formula VI are the same. In some embodiments, the two $R^1$ in formula VI are the same and the two $R^2$ in formula VI are the same.

In some embodiments, a compound of formula VI has the structure of formula VI-a:

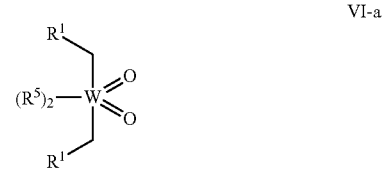

VI-a wherein each of $R^1$, n and $R^5$ is independently as defined above and described herein. In some embodiments, the two $R^1$ in formula VI-a are the same.

In some embodiments, each $R^1$ in formula VI or VI-a is R. In some embodiments, each $R^1$ in formula VI or VI-a is optionally substituted $C_{1-20}$ aliphatic. In some embodiments, each $R^1$ in formula VI or VI-a is optionally substituted tert-butyl.

In some embodiments, each $R^5$ in formula VI or VI-a is independently a monodentate ligand. In some embodiments, each $R^5$ in formula VI or VI-a is independently a monodentate nitrogen-containing ligand. In some embodiments, each $R^5$ in formula VI or VI-a is independently a monodentate phosphorus-containing ligand.

In some embodiments, two $R^5$ in formula VI-a are taken together with their intervening atoms to form an optionally substituted bidentate moiety. In certain embodiments, two $R^5$ are taken together to form optionally substituted bidentate bipyridyl.

In some embodiments, a compound of formula VI is WO(CH$_2$t-Bu)(bipy) (bipy=2,2'pyridine). In some embodiments, a compound of formula VI is WO(CH$_2$CMe$_2$Ph)(bipy) (bipy=2, 2'pyridine).

In some embodiments, the present invention provides a compound of formula VII:

VII wherein each $R^9$ is independently as defined above and described herein. In some embodiments, a compound of formula VII is W(O)$_2$(Cl)$_2$(bipy). In some embodiments, a compound of formula VII is W(O)$_2$(Br)$_2$(bipy).

In some embodiments, the present invention provides a compound of formula VIII:

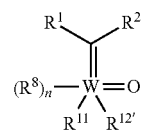

VIII wherein:
$R^{12'}$ is —OR or —OSiR$_3$; and
each of $R^1$, $R^2$, $R^8$, $R^{11}$, R and n is independently as defined above and described herein. In some embodiments, a compound of formula VIII is other than WO(CH-t-Bu)(O-2,6-Ph$_2$C6H$_3$)$_2$(R$^8$)$_n$. In some embodiments, at least one of $R^{11}$ and $R^{12'}$ is not —O-2,6-$Ph_2C6H_3$. In some embodiments, n=0. In some embodiments, n=1.

In some embodiments, the present invention provides a compound of formula VIII-a,

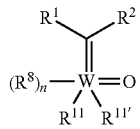

VIII-a wherein $R^{11'}$ is —OR;
each of $R^1$, $R^2$, $R^8$, $R^{11}$, R and n is independently as defined above and described herein. In some embodiments, both $R^{11}$ and $R^{11'}$ are the same. In some embodiments, $R^{11}$ and $R^{11'}$ are different. Exemplary —OR embodiments for $R^{11}$ and $R^{11'}$ are extensively described above and herein, including but not limited to those described for $R^3$ and $R^4$. In some embodiments, at least one of $R^{11}$ and $R^{11'}$ is not —O-2,6-$Ph_2C6H_3$. In some embodiments, a compound of formula VIII-a is other than WO(CH-t-Bu)(O-2,6-$Ph_2C6H_3$)$_2$($R^8$)$_n$. In some embodiments, n=0. In some embodiments, n=1.

In some embodiments, a compound of formula VIII-a is W(O)(CH-t-Bu)(OHMT)$_2$. In some embodiments, a compound of formula VIII-a is W(O)(CH$_2$)(OHMT)$_2$. In some embodiments, a compound of formula VIII-a is W(O)(CH$_2$)(DFTO)$_2$.

In some embodiments, the present invention provides a compound of formula VIII-b,

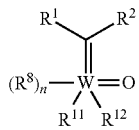

VIII-b wherein $R^{12}$ is —OSiR$_3$, and each of $R^1$, $R^2$, $R^8$, $R^{11}$, R and n is independently as defined above and described herein. In some embodiments, n=0.

In some embodiments, $R^{12}$ is —OSiR$_3$ wherein at least one R is not hydrogen. In some embodiments, $R^{12}$ is —OSiR$_3$ wherein at least two R are not hydrogen. In some embodiments, $R^{12}$ is —OSiR$_3$ wherein none of R is hydrogen. In some embodiments, $R^{12}$ is —OSiR$_3$ wherein each R is independently an optionally substituted group selected from $C_{1-20}$ aliphatic and phenyl. In some embodiments, $R^{12}$ is —OSiR$_3$ wherein at least one R is optionally substituted $C_{1-20}$ aliphatic. In some embodiments, $R^{12}$ is —OSiR$_3$ wherein at least one R is optionally substituted phenyl. In some embodiments, $R^{12}$ is —OSi(t-Bu)$_3$. In some embodiments, a compound of formula VIII-b is WO(CH-t-Bu)[OSi(t-Bu)$_3$](OHMT). In some embodiments, a compound of formula VIII-b is WO(CH-t-Bu)[OSi(t-Bu)$_3$](OHIPT). In some embodiments, a compound of formula VIII-b is WO(CH-t-Bu)[OSi(t-Bu)$_3$](DFTO).

In some embodiments, a compound of formula VIII is W(O)(CH-t-Bu)(OHMT)$_2$. In some embodiments, a compound of formula VIII is W(O)(CH$_2$)(OHMT)$_2$. In some embodiments, a compound of formula VIII is WO(CH-t-Bu)[OSi(t-Bu)$_3$](OHMT). In some embodiments, a compound of formula VIII-b is WO(CH-t-Bu)[OSi(t-Bu)$_3$](OHIPT). In some embodiments, a compound of formula VIII-b is WO(CH-t-Bu)[OSi(t-Bu)$_3$](DFTO).

In some embodiments, the present invention provides a compound of formula IX:

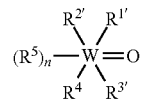

IX wherein:
$R^{1'}$ and $R^{2'}$ are taken together with W to form an optionally substituted 3-8 membered saturated or partially unsaturated ring having, in addition to the intervening metal atom, 0-4 heteroatoms independently selected from nitrogen, oxygen, or sulfur;
$R^{3'}$ is $R^3$ or —OSiR$_3$; and
each of $R^3$, $R^4$, $R^5$ and n is independently as defined above and described herein.

In some embodiments, $R^{1'}$ and $R^{2'}$ are taken together with W to form an optionally substituted 4 membered metallacyclobutane. In some embodiments, $R^{1'}$ and $R^{2'}$ are taken together with W to form a substituted 4 membered metallacyclobutane. In some embodiments, $R^{1'}$ and $R^{2'}$ are taken together with W to form an unsubstituted 4 membered metallacyclobutane.

In some embodiments, $R^{3'}$ is $R^3$, wherein $R^3$ is as defined above and described herein. In some embodiments, $R^{3'}$ is —OSiR$_3$, wherein each R is independently as defined above and described herein. In some embodiments, $R^{3'}$ is —OSiR$_3$ wherein at least one R is not hydrogen. In some embodiments, $R^{3'}$ is —OSiR$_3$ wherein at least two R are not hydrogen. In some embodiments, $R^{3'}$ is —OSiR$_3$ wherein none of R is hydrogen. In some embodiments, $R^{3'}$ is —OSiR$_3$ wherein at least one R is optionally substituted $C_{1-20}$ aliphatic. In some embodiments, $R^{3'}$ is —OSiR$_3$ wherein at least one R is optionally substituted phenyl. In some embodiments, $R^{3'}$ is —OSi(t-Bu)$_3$.

In some embodiments, $R^{3'}$ is —OR, wherein R is optionally substituted phenyl; or $R^{3'}$ is —OSiR$_3$. In some embodiments, $R^{3'}$ is —OR, wherein R is optionally substituted phenyl; or $R^{3'}$ is —OSiR$_3$, wherein each R is independently optionally substituted $C_{1-20}$ aliphatic or phenyl.

In some embodiments, $R^{3'}$ is not —O-2,6-$Ph_2C6H_3$.

In some embodiments, each of $R^{3'}$ and $R^4$ is independently —OR, wherein R is independently optionally substituted phenyl. In some embodiments, $R^{3'}$ is —OSiR$_3$, wherein each R is independently optionally substituted $C_{1-20}$ aliphatic or phenyl; and $R^4$ is —OR, wherein R is optionally substituted phenyl. In some embodiments, $R^{3'}$ is —OR, wherein R is optionally substituted phenyl; or $R^{3'}$ is —OSiR$_3$, wherein each R is independently optionally substituted $C_{1-20}$ aliphatic or phenyl.

In some embodiments, a compound of formula IX is W(O)(CH$_2$CH$_2$CH$_2$)(OHMT)(Silox) (Silox=-OSi(t-Bu)$_3$). In some embodiments, a compound of formula IX is W(O)(C$_3$H$_6$)(OHMT)$_2$. In some embodiments, a compound of formula IX is W(O)(C$_3$H$_6$)(OHIPT)$_2$. In some embodiments, a compound of formula IX is W(O)(C$_3$H$_6$)(DFTO)$_2$.

In some embodiments, the present invention provides novel ligands their corresponding protonated compounds or salts thereof. In some embodiments, the present invention provides methods for preparing novel ligands and their corresponding protonated compounds or salts thereof. In some embodiments, a novel ligand is 2,6-pentafluorophenylphenoxide (DFTO or decafluoroterphenoxide). In some embodiments, a protonated compound of DFTO is DFTOH. In some embodiments, a salt of DFTO is LiODFT. In some embodiments, the present invention provides a method for preparing DFTOH or its salts thereof.

A provided novel ligand can be utilized to prepare novel compound or metal complexes. In some embodiments, the present invention provides a compound or metal complex comprising a novel ligand. In some embodiments, the present invention provides a compound or metal complex comprising one or more DFTO ligands. In some embodiments, the present invention provides a compound or metal complex comprising one or more DFTOH ligands. In some embodiments, the present invention provides a compound having the structure of formula I, II, III, IV, V, VI, VII, VIII, or IX, and comprising one or more DFTO ligands. In some embodiments, the present invention provides a compound having the structure of formula I, II, III, IV, V, VI, VII, VIII, or IX, and comprising one or more DFTOH ligands.

In some embodiments, a provided compound in this invention forms a complex with a Lewis acid. In some embodiments, a Lewis acid comprises a boron atom. In some embodiments, a Lewis acid is of the structure of B(R')$_3$. In some embodiments, a Lewis acid is of the structure of B(R)$_3$. In some embodiments, a Lewis acid is of the structure of B(R)$_3$, wherein R is not hydrogen. In some embodiments, a Lewis acid is of the structure of B(R)$_3$, wherein R is an optionally substituted $C_{1-20}$ aliphatic or phenyl. In some embodiments, a Lewis acid is of the structure of B(R)$_3$, wherein R is an optionally substituted phenyl. In some embodiments, a Lewis acid is $B(C_6F_5)_3$.

In some embodiments, the present invention provides a compound having the structure of any of the formulae described herein, wherein the compound is a 14e tungsten oxo alkylidene complex. In some embodiments, the present invention provides a compound having the structure of any of the formulae described herein, wherein the compound is a 14e tungsten oxo alkylidene complex and the complex is a syn isomer. In some embodiments, the present invention provides a compound having the structure of any of the formulae described herein, wherein the compound is a 16e tungsten oxo alkylidene complex.

In some embodiments, the present invention provides a compound having the structure of any of the formulae described herein, wherein at least one ligand is an optionally substituted phenoxide. In some embodiments, the present invention provides a compound having the structure of any of the formulae described herein, wherein at least one ligand is an optionally substituted 2,6-terphenoxide. In some embodiments, an optionally substituted 2,6-terphenoxide is OHMT. In some embodiments, an optionally substituted 2,6-terphenoxide is OHIPT. In some embodiments, an optionally substituted 2,6-terphenoxide is DFTO. In some embodiments, such a compound has good stability. In some embodiments, the existence of optionally substituted 2,6-terphenoxide ligand contribute to decrease composition. In some embodiments, the existence of optionally substituted 2,6-terphenoxide ligand contribute to decrease bimolecular composition.

Methods of Making Compounds

The present invention recognizes the importance of improved methods to prepare tungsten oxo alkylidene complexes. It has been known in the art that it is a challenge to make relatively stable and reactive versions of tungsten oxo alkylidene complexes in good yield.

In certain embodiments, the present invention further provides methods of making provided compounds. In some embodiments, a provided compound is synthesized from a synthetically accessible or commercially available metal complex and one or more suitable ligands.

In some embodiments, the present invention provides a method of preparing a compound of formula I, comprising reacting a metal compound of formula V:

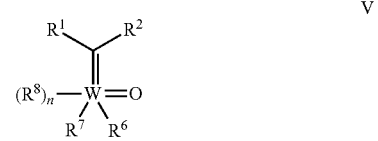

wherein:
each of $R^1$ and $R^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;
each $R^6$ and $R^7$ is halogen, —OR or a phosphorus-containing ligand;
each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:
  two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:
  two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;
n is 0, 1, or 2;
each $R^8$ is independently a monodentate ligand, or two $R^8$ are taken together with their intervening atoms to form an optionally substituted bidentate group; and
two or more of $R^1$, $R^2$, $R^6$ $R^7$ and $R^8$ may be taken together with their intervening atoms to form an optionally substituted polydentate ligand;
with one or more suitable ligands to form a compound of formula I:

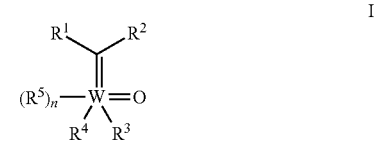

wherein each of n, $R^1$, $R^2$, $R^3$ $R^4$ and $R^5$ is independently as defined above or described herein.

In some embodiments, each of $R^6$, $R^7$ and $R^8$ is independently selected from halogen and $P(R')_3$, wherein each $R'$ is independently as defined above or described herein. In some embodiments, each of $R^6$ and $R^7$ is independently halogen and each of $R^8$ is independently $P(R')_3$. In some embodiments, n=2, each of $R^6$ and $R^7$ is independently halogen, and each of $R^8$ is independently $P(R')_3$. In some embodiments, n=2, each of $R^6$ and $R^7$ is independently halogen, and each of $R^8$ is independently $P(R)_3$.

In some embodiments, a compound of formula V is $WO(CHR^1R^2)(P(R)_3)_2Cl_2$, or $WO(CHR^1R^2)(P(R)_3)_2Br_2$, wherein each of $R^1$ and $R^2$ is independently as defined above or described herein, and each R is independently an optionally substituted group selected from $C_{1-20}$ aliphatic or phenyl. In some embodiments, a compound of formula V is $WO(CH-t-Bu)(PMe_2Ph)_2Cl_2$. In some embodiments, a compound of formula V is $WO(CH-t-Bu)(PMe_3)_2Cl_2$.

In some embodiments, the present invention provides simplified method for preparing tungsten oxo alkylidene complexes having the structure of formulae V, V-a, and V-b. In some embodiments, a compound of formula V has the structure of formula V-a:

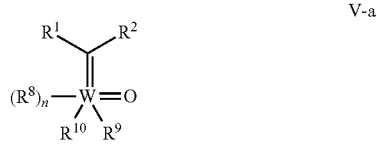

wherein:
each of $R^9$ and $R^{10}$ is independently halogen; and
each of $R^1$, $R^2$, $R^8$ and n is independently as defined above and described herein.

In some embodiments, the present invention provides a method of making a tungsten oxo alkylidene complex, wherein the alkylidene is prepared on tungsten. Such methods differ from those in which the alkylidene group is "transferred" from another metal, for example, in the transformation below (L=$PMe_2Ph$):

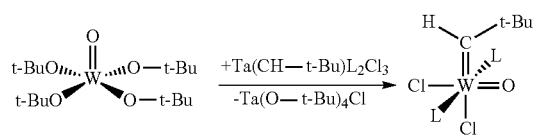

Exemplary methods in which the alkylidene group is prepared on tungsten are described herein.

In some embodiments, the present invention provides a method of making a compound of formula V-a:

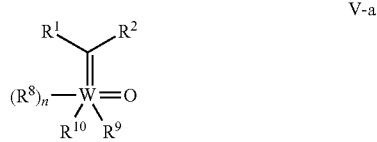

comprising the use of a compound of formula VI:

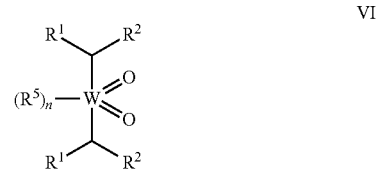

wherein each of $R^1$, $R^2$, $R^5$, $R^8$, $R^9$, $R^{10}$ and n is independently as defined above and described herein. In some embodiments, the two $R^1$ in formula VI are the same. In some embodiments, the two $R^2$ in formula VI are the same. In some embodiments, the two $R^1$ in formula VI are the same and the two $R^2$ in formula VI are the same.

In some embodiments, a compound of formula VI has the structure of formula VI-a:

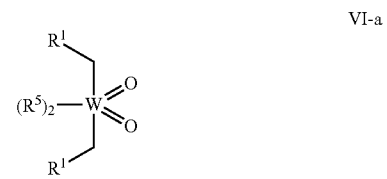

wherein each of $R^1$, n and $R^5$ is independently as defined above and described herein. In some embodiments, the two $R^1$ in formula VI-a are the same.

In some embodiments, each $R^1$ in formula VI or VI-a is R. In some embodiments, each $R^1$ in formula VI or VI-a is optionally substituted $C_{1-20}$ aliphatic. In some embodiments, each $R^1$ in formula VI or VI-a is optionally substituted tert-butyl.

In some embodiments, each $R^5$ in formula VI or VI-a is independently a monodentate ligand. In some embodiments, each $R^5$ in formula VI or VI-a is independently a monodentate nitrogen-containing ligand. In some embodiments, each $R^5$ in formula VI or VI-a is independently a monodentate phosphorus-containing ligand.

In some embodiments, two $R^5$ in formula VI-a are taken together with their intervening atoms to form an optionally substituted bidentate moiety. In certain embodiments, two $R^5$ are taken together to form optionally substituted bidentate bipyridyl.

In some embodiments, a compound of formula VI is $WO(CH_2t-Bu)(bipy)$ (bipy=2, 2'pyridine). In some embodiments, a compound of formula VI is $WO(CH_2CMe_2Ph)(bipy)$ (bipy=2, 2'pyridine).

In some embodiments, the above method of preparing a compound of formula V or V-a further comprises the use of a Lewis acid. In some embodiments, the above method of preparing a compound of formula V or V-a further comprises the use of a salt of zinc. In some embodiments, the above method of preparing a compound of formula V or V-a further comprises the use of $ZnCl_2$(dioxane).

In some embodiments, the above method of preparing a compound of formula V or V-a further comprises the use of $R_3SiR^9$, wherein each of R and $R^9$ is independently as defined above and described herein. In some embodiments, $R_3SiR^9$ is TMSCl.

In some embodiments, the above method of preparing a compound of formula V or V-a further comprises the use of $R^8$, wherein $R^8$ is as defined above and described herein. In some embodiments, $R^8$ is $PR_3$, wherein each R is independently as defined above and described herein. In some embodiments, $R^8$ is $PMe_2Ph$.

In some embodiments, a provided method involves formation of the alkylidene ligand on tungsten through α hydrogen atom abstraction in the corresponding dialkyl precursor. In some embodiments, the alkylidene ligand is =CH(t-Bu) and the two corresponding alkyl groups are —$CH_2t$-Bu.

In some embodiments, the present invention provides a method of preparing a compound of formula V-b:

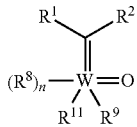

V-b comprising reacting a first compound of formula V-a:

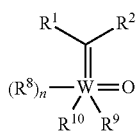

V-a with a second compound having the structure of $R^{11}H$ or its salt thereof, wherein:

$R^{11}$ is —OR; and each of $R^1$, $R^2$, $R^8$, $R^9$, $R^{10}$, R and n is independently as defined above and described herein.

In some embodiments, a second compound in the above method is $R^{11}H$. In some embodiments, a second compound in the above method is the alkoxide or aryloxide salt of $R^{11}H$. In some embodiments, a second compound is $R^{11}Li$. In some embodiments, a compound of formula V-b is W(O)(CH-t-Bu)(OHMT)(PMe$_2$Ph)Cl. In some embodiments, a compound of formula V-b is W(O)(CH-t-Bu)(OHIPT)(PMe$_2$Ph)Cl. In some embodiments, a compound of formula V-b is W(O)(CH-t-Bu)(DFTO)(PMe$_2$Ph)Cl.

In some embodiments, the present invention provides a method of preparing a compound having the structure of formula VI:

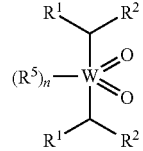

VI comprising the use of a compound having the formula VII:

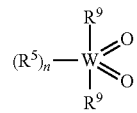

VII wherein each of $R^1$, $R^2$, $R^5$, $R^9$ and n is independently as defined above and described herein.

In some embodiments, a compound of formula VII is W(O)$_2$(Cl)$_2$(bipy). In some embodiments, a compound of formula VII is W(O)$_2$(Br)$_2$(bipy).

In some embodiments, the present invention provides a method of preparing a compound having the structure of formula VI

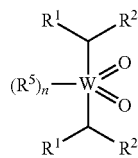

VI comprising reacting a first compound having the structure of formula VII:

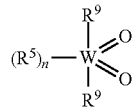

VII with a second compound comprising a

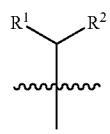

moiety directly bonded to a metal, wherein each of $R^1$, $R^2$, $R^5$, $R^9$ and n is independently as defined above and described herein, and the two

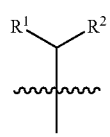

moieties in formula VI and the second compound are the same.

In some embodiments, the present invention provides a method of preparing a compound having the structure of formula VI-a:

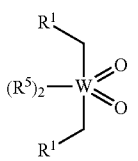

VI-a comprising reacting a first compound having the structure of formula VII:

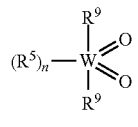

VII with a second compound comprising a

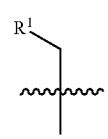

moiety directly bonded to a metal, wherein each of $R^1$, $R^2$, $R^5$, $R^9$ and n is independently as defined above and described herein, and the two $R^1$ in formula VI-a and the second compound are the same.

In some embodiments, a second compound in the provided methods is a Grignard reagent. In some embodiments, a second compound in the provided methods is a Grignard reagent having the formula of $R^1CH(R^2)MgR^{10}$. In some embodiments, a second compound in the provided methods is a Grignard reagent having the formula of $R^1CH(R^2)MgR^{10}$. In some embodiments, a second compound in the provided methods is a Grignard reagent having the formula of $R^1CH_2MgR^{10}$. In some embodiments, such a Grignard reagent is t-BuCH$_2$MgCl. In some embodiments, such a Grignard reagent is PhC(Me)$_2$CH$_2$MgCl.

In some embodiments, the present invention provides a method of preparing a compound having the structure of formula VII:

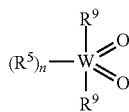

VII comprising the use of W(R$^9$)$_6$. In some embodiments, such a method further comprises the use of R$^5$. In some embodiments, a provided method further optionally comprises the use of dimethoxyethane (DME). In some embodiments, a provided method further comprises the use of TMS$_2$O. In some embodiments, W(R$^9$)$_6$ is WCl$_6$.

In some embodiments, the present invention provides methods to prepare multiple types of oxo alkylidene species from a compound of formula V-b, including but not limited to compounds having the structure of formula I. Exemplary compounds and methods are described below.

In some embodiments, the present invention provides a method of making a compound of formula I, wherein $R^3$ is —OR and $R^4$ is —N(R)$_2$, comprising reacting a first compound of formula V-b, wherein $R^{11}$ is —$R^3$, with a second compound of formula R$_2$NH or its anionic amide salt thereof;
wherein each variable is independently as defined above and described herein.

In some embodiments, $R^3$ and $R^{11}$ in the above method are —OR, wherein R is optionally substituted phenyl. Exemplary optionally substituted phenyl is extensive described in the specification including but not limited to the embodiments for $R^3$, $R^4$ and $R^{11}$. In some embodiments, —OR is —OHMT. In some embodiments, —OR is OHIPT. In some embodiments, —OR is DFTO.

In some embodiments, a second compound in the above method is the anionic amide salt of R$_2$NH. In some embodiments, a second compound in the above method is LiNR$_2$. Exemplary embodiments of R or —NR$_2$ are extensively and independently defined above and described herein, including but not limited to the embodiments for $R^3$ and $R^4$. In some embodiments, two R groups are taken together with the nitrogen to form an optionally substituted 5-membered heteroaryl ring having 0-3 additional nitrogen atoms not including the N atom from —N(R)$_2$. Such rings include optionally substituted pyrrol-1-yl, pyrazol-1-yl, imidazol-1-yl, and triazol-1-yl. In some embodiments, such rings are unsubstituted pyrrol-1-yl, pyrazol-1-yl, imidazol-1-yl, and triazol-1-yl. In some embodiments, a compound of formula V-b is W(O)(CH-t-Bu)(OHMT)(PMe$_2$Ph)Cl. In some embodiments, a compound of formula V-b is W(O)(CH-t-Bu)(OHIPT)(PMe$_2$Ph)Cl. In some embodiments, a compound of formula V-b is W(O)(CH-t-Bu)(DFTO)(PMe$_2$Ph)Cl. In some embodiments, a second compound is LiPh$_2$Pyr. In some embodiments, a second compound is LiMe$_2$Pyr. In some embodiments, a compound of formula I is W(O)(CH-t-Bu)(Ph$_2$Pyr)(OHMT). In some embodiments, a compound of formula I is W(O)(CH-t-Bu)(Ph$_2$Pyr)(OHIPT). In some embodiments, a compound of formula I is W(O)(CH-t-Bu)(Ph$_2$Pyr)(DFTO). In some embodiments, a compound of formula I is W(O)(CH-t-Bu)(Me$_2$Pyr)(OHMT)(PMe$_2$Ph). In some embodiments, a compound of formula I is W(O)(CH-t-Bu)(Me$_2$Pyr)(OHIPT). In some embodiments, a compound of formula I is W(O)(CH-t-Bu)(Me$_2$Pyr)(DFTO). As used herein, Ph$_2$Pyr is

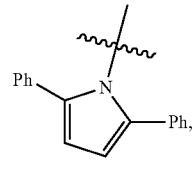

and Me$_2$Pyr is

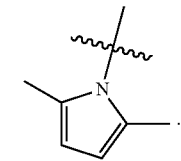

In some embodiments, a second compound is LiN(C$_6$F$_5$)$_2$, and a compound of formula I is W(O)(CH-t-Bu)[N(C$_6$F$_5$)$_2$](OHMT)(PPhMe$_2$).

In some embodiments, the present invention provides a method of making a compound of formula I, wherein each of $R^3$ and $R^4$ is independently —OR, comprising: reacting a first compound of formula V-b, wherein $R^{11}$ is $R^4$ in formula I, with a second compound of formula R$^3$H or its salt thereof, wherein $R^3$ is the same as $R^3$ of formula I, wherein each variable is independently as defined above and described herein.

In some embodiments, the present invention provides a method of making a compound of formula I, wherein $R^3$ and $R^4$ are the same and are —OR, comprising: reacting a first compound of formula V-a with a second compound of formula R$^3$H or its salt thereof; wherein each variable is independently as defined above and described herein.

In some embodiments, a second compound is the salt of R$^3$H. In some embodiments, a second compound is R$^3$Li. Exemplary —OR for $R^3$, $R^4$ and $R^{11}$ is extensively described above and herein. In some embodiments, R is optionally substituted phenyl. In some embodiments, $R^3$ and $R^4$ are the same. In some embodiments, $R^3$ and $R^4$ are different. In some embodiments, one of $R^3$ and $R^4$ is —OHMT. In some embodiments, one of $R^3$ and $R^4$ is —OHIPT. In some embodiments, one of $R^3$ and $R^4$ is -DFTO. In some embodiments, both of $R^3$ and $R^4$ are —OHMT. In some embodiments, both of $R^3$ and $R^4$ are —OHIPT. In some embodiments, both of $R^3$ and $R^4$ are -DFTO. In some embodiments, a compound of formula I is W(O)(CH-t-Bu)(OHMT)$_2$. In some embodiments, a compound of formula I is W(O)(CH-t-Bu)(OHIPT)$_2$. In some embodiments, a compound of formula I is W(O)(CH-t-Bu)(DFTO)$_2$. In some embodiments, at least one of R$^3$ and R$^4$ is not —O-2,6-Ph$_2$C6H$_3$.

In some embodiments, R$^3$Li is LiOHMT. In some embodiments, R$^3$Li is LiOHIPT. In some embodiments, R$^3$Li is LiODFT.

In some embodiments, the present invention provides a method of making a compound of formula VIII-a:

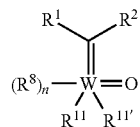

VIII-a comprising reacting a first compound of formula V-b:

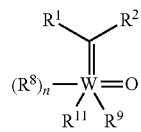

V-b with a second compound of formula R$^{11}$H or its salt thereof, wherein each variable is independently as defined above and described herein.

In some embodiments, a second compound is the salt of R$^{11'}$H. In some embodiments, a second compound is R$^{11'}$Li. Exemplary —OR for R$^{11'}$ and R$^{11}$ is extensively described above and herein. In some embodiments, R is optionally substituted phenyl. In some embodiments, R$^{11}$ and R$^{11'}$ are the same. In some embodiments, R$^{11}$ and R$^{11'}$ are different. In some embodiments, one of R$^{11}$ and R$^{11'}$ is —OHMT. In some embodiments, one of R$^{11}$ and R$^{11'}$ is —OHIPT. In some embodiments, one of R$^{11}$ and R$^{11'}$ is -DFTO. In some embodiments, both of R$^{11}$ and R$^{11'}$ are —OHMT. In some embodiments, both of R$^{11}$ and R$^{11'}$ are —OHIPT. In some embodiments, both of R$^{11}$ and R$^{11'}$ are -DFTO. In some embodiments, a compound of formula I is W(O)(CH-t-Bu)(OHMT)$_2$. In some embodiments, a compound of formula I is W(O)(CH-t-Bu)(OHIPT)$_2$. In some embodiments, a compound of formula I is W(O)(CH-t-Bu)(DFTO)$_2$. In some embodiments, at least one of R$^{11}$ and R$^{11'}$ is not —O-2,6-Ph$_2$C6H$_3$.

In some embodiments, R$^{11'}$Li is LiOHMT. In some embodiments, R$^{11'}$Li is LiOHIPT. In some embodiments, R$^{11}$Li is LiODFT.

In some embodiments, the present invention provides a method of making a compound of formula VIII-b,

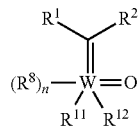

VIII-b comprising reacting a first compound of formula V-b:

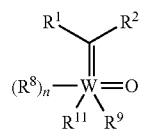

V-b with a second compound of formula R$^{12}$H or its salt thereof; wherein R$^{12}$ is —OSiR$_3$, and each of R$^1$, R$^2$, R$^8$, R$^{11}$, R and n is independently as defined above and described herein.

In some embodiments, a second compound is a salt of R$^{12}$H. In some embodiments, a second compound is R$^{12}$Na. In some embodiments, a second compound is NaOSi(t-Bu)$_3$.

As described above, in some embodiments, neutral ligands, such as neutral nitrogen-, oxygen-, and/or phosphorus-containing ligands for R$^5$ and R$^8$ (e.g., bipyr and phosphine ligands) can be partially associated with W. In some embodiments, such association can be detected by NMR. In some embodiments, while not wishing to be bound by any theory, dissociation is caused by the greater steric demand of ligands other than the neutral ligands. In some embodiments, a compound is detected or isolated without the neutral ligand, for example, without R$^5$ or R$^8$ (n=0). In some embodiments, such a compound comprises OHIPT. In other embodiments, a compound is detected or isolated with one or more neutral ligand, for example, with R$^5$ and/or R$^8$ (n=1 or n=2). In some embodiments, such a compound comprises OHMT. In some embodiments, such a compound comprises OHIPT. In some embodiments, such a compound comprises DFTO. The present invention recognizes that in the provided methods, the neutral ligands (e.g., R$^5$ or R$^8$) may dissociate due to the association of new ligands. A non-limiting example is when W(O)(CH-t-Bu)(OHMT)$_2$ is formed by reacting W(O)(CH-t-Bu)(OHMT)(PMe$_2$Ph)Cl with LiOHMT.

In some embodiments, the present invention provides a method of making a compound of formula IX:

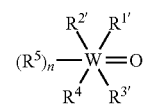

IX comprising reacting a first compound of formula I-c:

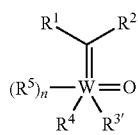

I with a second compound comprising a double bond, wherein each variable is independently as defined above and described herein.

In some embodiments, each of R$^{3'}$ and R$^4$ is independently —OR. In some embodiments, R$^{3'}$ is —OSiR$_3$ and R$^4$ is independently —OR.

In some embodiments, a second compound comprising a double bond in the above method is a terminal olefin. In some embodiments, a second compound comprising a double bond is ethylene.

In some embodiments, the provided methods would be beneficial to the preparation and application of oxo alkylidene compounds. For example, among other benefits, the provided methods for uses cheaper and widely available starting material (e.g., WCl$_6$), and/or simpler reaction and/or purification procedures. In some embodiments, the provided methods also produce compound with higher purity and/or activity.

In some embodiments, a ligand is provided in a molar ratio of about 10:1, 9:1, 8:1, 7:1, 6:1, 5:1, 4:1, 3:1, 2:1, or 1:1 relative to the metal complex. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal complex. In certain embodiments, a ligand is provided in a molar ratio of about 1:1 relative to the metal complex. One of skill in the art will appreciate that the optimal molar ratio of ligand to metal complex will depend on, inter alia, whether the ligand is mono- or polydentate.

In some embodiments, a ligand is provided in a molar ratio of about 10:1, 9:1, 8:1, 7:1, 6:1, 5:1, 4:1, 3:1, 2:1, or 1:1 relative to the metal complex of formula III. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal complex of formula III. In certain embodiments, a ligand is provided in a molar ratio of about 1:1 relative to the metal complex of formula III. One of skill in the art will appreciate that the optimal molar ratio of ligand to metal complex will depend on, inter alia, whether the ligand is mono- or polydentate.

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, tetrahydrofuran (THF), or dioxanes, or mixtures thereof. In certain embodiments, one or more solvents are deuterated.

In some embodiments, a single solvent is used. In certain embodiments, the solvent is benzene. In certain embodiments, the solvent is ether.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent:hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Suitable conditions for forming a provided precursor complex or a compound typically employ ambient reaction temperatures. In some embodiments, a suitable reaction temperature is about 15° C., about 20° C., about 25° C., or about 30° C. In some embodiments, a suitable reaction temperature is from about 15° C. to about 25° C. In certain embodiments, a suitable reaction temperature is about 20° C., 21° C., 22° C., 23° C., 24° C., or 25° C.

In certain embodiments, a provided method for preparing a provided precursor complex or a compound is performed at elevated temperature. In some embodiments, a suitable reaction temperature is from about 25° C. to about 110° C. In certain embodiments, a suitable reaction temperature is from about 40° C. to about 100° C., from about 50° C. to about 100° C., from about 60° C. to about 100° C., from about 70° C. to about 100° C., from about 80° C. to about 100° C., or from about 90° C. to about 100° C.

In certain embodiments, a provided method for preparing a provided precursor complex or a compound is performed at temperature lower than ambient temperatures. In some embodiments, a suitable reaction temperature is from about −100° C. to about 10° C. In certain embodiments, a suitable reaction temperature is from about −80° C. to about 0° C., from about −70° C. to about 0° C., from about −60° C. to about 0° C., from about −50° C. to about 0° C., from about −40° C. to about 0° C., or from about −30° C. to about 0° C.

In some embodiments, a provided method is performed at different temperatures. In some embodiments, the reaction temperature changes in a provided method. In some embodiments, a provided method involves temperature increase from a lower temperature to a higher temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C. In some embodiments, a provided method comprises temperature increase from about −30° C. to 22° C. In some embodiments, a provided method comprises temperature decrease from a higher temperature to a lower temperature. In some embodiments, a provided method comprises temperature increase from about 110° C., about 100° C., about 90° C., about 80° C., about 70° C., about 60° C., about 50° C., about 40° C., about 30° C., about 25° C., about 22° C., ambient temperature, about 20° C., about 10° C., and about 0° C. to about 0° C., about −10° C., about −20° C., about −30° C., about −40° C., about −50° C., about −60° C., about −70° C., about −80° C., about −90° C., and about −100° C.

Suitable conditions for forming a provided precursor complex or a compound typically involve reaction times of about 1 minute to about 1 day. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1 hour. In certain embodiments, the reaction time is about 2, 3, 4, 5, 6, 7, 8, 9, 10, 11, or 12 hours. In some embodiments, the reaction time is about 12 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 30 minutes.

Exemplary Uses of Provided Compounds

As described herein, provided compounds of formula I are particularly useful for metathesis reactions.

In some embodiments, methods using provided compounds involve reacting a first species and a second species to form a product comprising a double bond, wherein the double bond comprises an atom of the first species and an atom of the second species. In some embodiments, the first species and the second species are different. In some embodiments, the first species and the second species are the same. In some embodiments, the double bond may comprise a carbon atom from the first species and a carbon atom from the second species. The double bond produced may have a Z (e.g., cis) or E (e.g., trans) configuration. Those of ordinary skill in the art would understand the meaning of the terms "cis" or "Z" and "trans" or "E," as used within the context of the invention.

Some embodiments may provide the ability to selectively synthesize, via a metathesis reaction, products having a Z or E configuration about a double bond. In some embodiments, methods using compounds of formula I of the present invention may provide the ability to synthesize compounds comprising a Z-disubstituted olefin. In some embodiments, such methods are useful when applied to a wide range of olefin substrates, including those having sterically small or large groups adjacent the olefin. In some embodiments, the substrate olefins are terminal olefins. In some embodiments, complexes of the present invention are useful in methods for synthesizing Z-disubstituted enol ethers. In some embodiments, complexes of the present invention are useful in methods for synthesizing Z-disubstituted allylic amines. In some embodiments, complexes of the present invention are useful in methods for synthesizing Z-disubstituted allylic amides.

In some embodiments, a compound of formula I promotes Z-selective olefin metathesis reactions. In some embodiments, a compound of formula I promotes E-selective olefin metathesis reactions.

In some embodiments, a metathesis reaction using a compound of formula I produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some embodiments, a metathesis reaction using a compound of formula I produces a double bond in an E:Z ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC). In some cases, about 100% of the double bond produced in the metathesis reaction may have an E configuration. The E or trans selectivity may also be expressed as a percentage of product formed. In some cases, the product may be greater than about 50% E, greater than about 60% E, greater than about 70% E, greater than about 80% E, greater than about 90% E, greater than about 95% E, greater than about 96% E, greater than about 97% E, greater than about 98% E, greater than about 99% E, or, in some cases, greater than about 99.5% E.

Without wishing to be bound by any particular theory, it is believed that the Z-selectivity is due, at least in part, to the small size of the oxo ligand relative to $R^3$, wherein $R^3$ is as defined above and described herein.

In some embodiments, a compound of formula I isomerizes a product. In some embodiments, a compound of formula I isomerizes a Z product. In some embodiments, a compound of formula I isomerizes a Z product slower than the formation of the product. In some embodiments, a compound of formula I isomerizes a E product. In some embodiments, a compound of formula I isomerizes a E product slower than the formation of the product.

In some embodiments, a compound of formula I does not isomerizes a product. In some embodiments, a compound of formula I does not isomerizes a Z product. In some embodiments, a compound of formula I does not isomerizes a E product.

In some embodiments, a compound of formula I, or the active catalyst formed from a compound of formula I, is stable under metathesis condition. In some embodiments, a compound of formula I, or the active catalyst formed from a compound of formula I, decomposes under metathesis condition. In some embodiments, a compound of formula I, or the active catalyst formed from a compound of formula I, decomposes under metathesis condition within about 1 hour. In some embodiments, a compound of formula I, or the active catalyst formed from a compound of formula I, decomposes under metathesis condition within about 2 hours. In some embodiments, a compound of formula I, or the active catalyst formed from a compound of formula I, decomposes under metathesis condition within about 6 hours. In some embodiments, a compound of formula I, or the active catalyst formed from a compound of formula I, decomposes under metathesis condition within about 12 hours. In some embodiments, a compound of formula I, or the active catalyst formed from a compound of formula I, decomposes under metathesis condition within about 24 hours. In some embodiments, a compound of formula I, or the active catalyst formed from a compound of formula I, decomposes under metathesis condition within about 48 hours. In some embodiments, a compound of formula I, or the active catalyst formed from a compound of formula I, decomposes under metathesis condition within about 96 hours.

In some embodiments, a compound of formula I, or the active catalyst formed from a compound of formula I, decomposes prior to isomerization of a product. In some embodiments, a compound of formula I, or the active catalyst formed from a compound of formula I, partially decomposes prior to isomerization of a product. In some embodiments, a compound of formula I, or the active catalyst formed from a compound of formula I, decomposes prior to isomerization of a Z product. In some embodiments, a compound of formula I, or the active catalyst formed from a compound of formula I, partially decomposes prior to isomerization of a Z product. In some embodiments, a compound of formula I, or the active catalyst formed from a compound of formula I, decomposes prior to isomerization of a E product. In some embodiments, a compound of formula I, or the active catalyst formed from a compound of formula I, partially decomposes prior to isomerization of a E product.

In some embodiments, a metathesis reaction using a compound of the present invention produces a polymer wherein the polymer is >50% cis, >50% synditactic. In some embodiments, a metathesis reaction using a compound of the present invention produces a polymer wherein the polymer is >60% cis, >60% synditactic. In some embodiments, a metathesis reaction using a compound of the present invention produces a polymer wherein the polymer is >70% cis, >70% synditactic. In some embodiments, a metathesis reaction using a compound of the present invention produces a polymer wherein the polymer is 80% cis, >80% synditactic. In some embodiments, a metathesis reaction using a compound of the present invention produces a polymer wherein the polymer is >90% cis, 90% synditactic. In some embodiments, a metathesis reaction using a compound of the present invention produces a polymer wherein the polymer is >95% cis, 90% synditactic. In some embodiments, a metathesis reaction using a compound of the present invention produces a polymer wherein the polymer is >99% cis, 90% synditactic. In some embodiments, a metathesis reaction using a compound of the present invention produces a polymer wherein the polymer is >90% cis, >90% synditactic. In some embodiments, a metathesis reaction using a compound of the present invention produces a polymer wherein the polymer is >95% cis, >90% synditactic. In some embodiments, a metathesis reaction using a compound of the present invention produces a polymer wherein the polymer is >99% cis, >90% synditactic. In some embodiments, a metathesis reaction using a compound of the present invention produces a polymer wherein the polymer is >99% cis, >95% synditactic. In some embodiments, a metathesis reaction using a compound of the present invention produces a polymer wherein the polymer is >99% cis, >97% synditactic.

In some embodiments, a metathesis reaction using a compound of formula I is further accelerated by the addition of a Lewis acid. In some embodiments, such a Lewis acid is $B(C_6F_5)_3$.

As mentioned above, provided compounds are useful for metathesis reactions. Exemplary such methods and reactions are described below.

It will be appreciated that, in certain embodiments, each variable recited for the above method is as defined above and described in embodiments, herein, singly and in combination.

EXEMPLIFICATION

General Comments.

All manipulations were done either in a nitrogen-filled drybox or on an air free dual-manifold Schlenk line. The solvents were sparged with nitrogen, passed through activated alumina, and stored over activated 4 Å Linde-type molecular sieves. Methylene chloride-$d_2$, chloroform-$d_3$, and benzene-$d_6$ were distilled from calcium hydride ($CD_2Cl_2$, $CDCl_3$) or sodium ketyl ($C_6D_6$), and stored over activated 4 Å Linde-type molecular sieves. NMR spectra were recorded using Varian spectrometers at 500 ($^1H$), 125 ($^{13}C$), 121 ($^{31}P$), 471 ($^{19}F$), and 161 ($^{11}B$) MHz, reported in δ (parts per million) relative to tetramethylsilane ($^1H$, $^{13}C$), 85% phosphoric acid ($^{31}P$), $CFCl_3$ ($^{19}F$), or $BF_3 \cdot Et_2O$ ($^{11}B$), and referenced to the residual $^1H/^{13}C$ signals of the deuterated solvent ($^1H$ (δ): benzene 7.16; methylene chloride 5.32, chloroform 7.26; $^{13}C$ (δ): benzene 128.06; methylene chloride 53.84, chloroform 77.16), or external 85% phosphoric acid ($^{31}P$ (δ): 0.0), $C_6F_6$ ($^{19}F$ (δ): −169.4), and $BF_3 \cdot Et_2O$ ($^{11}B$ (δ): 0.0) standards. Midwest Microlab, Indianapolis, Ind. provided the elemental analysis results.

WO(CH-t-Bu)$Cl_2$(PMe$_2$Ph)$_2$ (Wengrovius, J. H.; Schrock, R. R. *Organometallics* 1982, 1, 148-155), Li(Me$_2$Pyr) (Jiang, A. J.; Simpson, J. H.; Müller, P.; Schrock, R. R. *J. Am. Chem. Soc.* 2009, 131, 7770-7780), HIPTOH (Stanciu, C.; Olmstead, M. M.; Phillips, A. D.; Stender, M.; Power, P. P. *Eur. J. Inorg. Chem.* 2003, 2003, 3495-3500), HIPTOLi (Stanciu, C.; Olmstead, M. M.; Phillips, A. D.; Stender, M.; Power, P. P. *Eur. J. Inorg. Chem.* 2003, 2003, 3495-3500), HMTOH (Dickie, D. A.; MacIntosh, I. S.; Ino, D. D.; He, Q.; Labeodan, O. A.; Jennings, M. C.; Schatte, G.; Walsby, C. J.; Clyburne, J. A. C. *Can. J. Chem.* 2008, 86, 20-31), HMTOLi (Dickie, D. A.; MacIntosh, I. S.; Ino, D. D.; He, Q.; Labeodan, O. A.; Jennings, M. C.; Schatte, G.; Walsby, C. J.; Clyburne, J. A. C. *Can. J. Chem.* 2008, 86, 20-31), DCMNBD (Tabor, D. C.; White, F.; Collier, L. W.; Evans, S. A. *J. Org. Chem.* 1983, 48, 1638-1643) were prepared according to reported procedures. The substrates for olefin homocoupling reactions were distilled from $CaH_2$ and stored in a glovebox over molecular sieves. All other reagents were used as received unless noted otherwise.

X-Ray Crystal Structure Determination Details.

Low-temperature diffraction data (φ- and ω-scans) were collected on a Bruker-AXS X8 Kappa Duo diffractometer coupled to a Smart APEX 2 CCD detector with Mo K$_α$ radiation (λ=0.71073 Å) from an IμS micro-source. Absorption and other corrections were applied using SADABS (Sheldrick, G. M. *SADABS, v.* 2.10 —*A program for area detector absorption corrections*; Bruker AXS: Madison, Wis., 2003). All structures were solved by direct methods using SHELXS (Sheldrick, G. M. *Acta Cryst.* 1990, A46, 467-473) and refined against $F^2$ on all data by full-matrix least squares with SHELXL-97 (Sheldrick, G. M. *Acta Cryst.* 2008, A64, 112-122) using established refinement approaches (Müller, P. *Crystallography Reviews* 2009, 15, 57-83). All non-hydrogen atoms were refined anisotropically. Hydrogen atoms were included in the models at geometrically calculated positions and refined using a riding model except for alkylidene protons. Coordinates for the alkylidene hydrogen atoms were taken from the difference Fourier synthesis and the hydrogen atoms were subsequently refined semi-freely with the help of a distance restraint, unless otherwise noted. The isotropic displacement parameters of all hydrogen atoms were fixed to 1.2 times the $U_{eq}$ value of the atoms they are linked to (1.5 times for methyl groups). All disordered atoms were refined with the help of similarity restraints on the 1,2- and 1,3- distances and displacement parameters as well as rigid bond restraints for anisotropic displacement parameters.

The compound W(O)(CH-t-Bu)(OHIPT)Cl(PMe$_2$Ph) (I-1) crystallizes in the monoclinic space group P2$_1$/c with one molecule in the asymmetric unit. The tungsten atom, chloride, oxo, and alkylidene ligands were modeled as a two component disorder and the ratio of the occupancies refined to 0.9130(18). One of the iPr groups was also found to be disordered over two positions, the ratio of occupancies refined to 0.694(17). The anisotropic displacement parameters for the chloride (Cl1, Cl1A), oxo (O2, O2A), and one carbon (C1, C1A) on the alkylidene were constrained to be equivalent, pairwise. Coordinates for the hydrogen atom bound to C1 was taken from the difference Fourier synthesis as noted above. However, the hydrogen atom bound to C1A, the minor component of the disorder, could not be found in the difference Fourier synthesis and was included in the model at a geometrically calculated position and refined using a riding model.

The compound W(O)(OHIPT)(Me$_2$Pyr) (I-2) crystallizes in the monoclinic space group P2$_1$/n with one molecule in the asymmetric unit. One of the aryl groups on the alkoxide ligand was modeled as a two component disorder and the ratio of the occupancies of the two components refined to 0.637(5). The anisotropic displacement parameters of all of atoms in this disorder were constrained to be equivalent, pairwise. The largest residual electron density was modeled as a second tungsten position and the relative occupancy of the two components refined to 0.9787(4). The anisotropic displacement parameters of the two components were constrained to be equivalent. The oxo, pyrrolide, and alkylidene were observed in the difference Fourier synthesis but refinement of these ligands as a disorder was unstable, therefore an alternative site was modeled only for the tungsten.

The compound W(O)(CH-t-Bu)(OHMT)(Me$_2$Pyr) (PMe$_2$Ph) (I-4) crystallizes in the triclinic space group P-1 with one molecule in the asymmetric unit along with one and a half molecules of pentane. One half of a pentane molecule is located near a crystallographic inversion center and disordered accordingly which leads to a non-integer value for carbon.

The compound W(O)(B(C$_6$F$_5$)$_3$(OHMT)(Me$_2$Pyr) (I-6) crystallizes in the monoclinic space group P2$_1$/n with one molecule in the asymmetric unit.

We prepared W(O)(CH-t-Bu)(OHIPT)(Me$_2$Pyr) (where Me$_2$Pyr=2,5-dimethylpyrrolide) from W(O)(CH-t-Bu)(PMe$_2$Ph)$_2$Cl$_2$ as the starting material. The reaction between WO(CH-t-Bu)Cl$_2$(PMe$_2$Ph)$_2$ and LiOHIPT in benzene at 22° C. for 14 h led to isolation of off-white WO(CH-t-Bu)Cl(OHIPT)(PMe$_2$Ph) (I-1) in 60% yield. Two isomers of I-1 are present in a 3:2 ratio according to $^1$H, $^{13}$C, and $^{31}$P NMR spectra. Both are syn alkylidenes on the basis of J$_{C\alpha H}$ values for the alkylidene of 123 Hz (major isomer) and 117 Hz (minor isomer). The phosphine remains bound to tungsten on the NMR time scale (J$_{PW}$=420 Hz and 379 Hz, respectively) at 22° C. An X-ray crystal structure (FIG. 1) revealed a distorted square-pyramidal geometry with the neopentylidene ligand in the apical position and the phosphine ligand trans to chloride. The alkylidene was found to be disordered over syn and anti orientations in 91:9 ratio. One possibility is that the other isomer has a similar structure in which the OHIPT and Cl ligands have switched positions.

TABLE 2

Crystal data and structure refinement details for W(O)(CH—t-Bu)(OHIPT)Cl(PMe$_2$Ph) (I-1).

| | |
|---|---|
| Identification code | x11139 |
| Empirical formula | C$_{49}$H$_{70}$ClO$_2$PW |
| Formula weight | 941.32 |
| Temperature | 100(2) K |
| Wavelength | 0.71073 Å |
| Crystal system | Monoclinic |
| Space group | P2$_1$/c |
| Unit cell dimensions | a = 22.6931(16) Å  α = 90°. |
| | b = 8.9674(6) Å  β = 104.2850(10)°. |
| | c = 23.7379(17) Å  γ = 90°. |
| Volume | 4681.3(6) Å$^3$ |
| Z | 4 |
| Density (calculated) | 1.336 Mg/m$^3$ |
| Absorption coefficient | 2.594 mm$^{-1}$ |
| F(000) | 1944 |
| Crystal size | 0.20 × 0.05 × 0.05 mm$^3$ |
| Theta range for data collection | 1.77 to 30.32°. |
| Index ranges | −32 <= h <= 32, −12 <= k <= 12, −33 <= l <= 33 |
| Reflections collected | 108649 |
| Independent reflections | 14056 [R(int) = 0.0492] |
| Completeness to theta = 30.32° | 100.0% |
| Absorption correction | Semi-empirical from equivalents |
| Max. and min. transmission | 0.8812 and 0.6250 |
| Refinement method | Full-matrix least-squares on F$^2$ |
| Data/restraints/parameters | 14056/267/576 |
| Goodness-of-fit on F$^2$ | 1.022 |
| Final R indices [I > 2sigma(I)] | R1 = 0.0197, wR2 = 0.0403 |
| R indices (all data) | R1 = 0.0264, wR2 = 0.0422 |
| Largest diff. peak and hole | 0.656 and −0.972 e · Å$^{-3}$ |

Reaction of I-1 with ethylene resulted in formation of methylidene complex WO(CH$_2$)(HIPTO)Cl(PMe$_2$Ph) (I-10) as confirmed by in situ $^1$H NMR (two doublets of doublets, δ=8.64 and 10.44 ppm, $^2$J$_{HH}$=10 Hz, $^3$J$_{Hp}$=4 Hz) data. The methylidene complex decomposes in solution in 24 h.

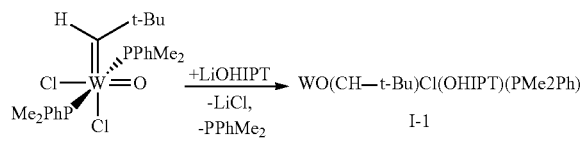

Synthesis of WO(CH-t-Bu)(OHIPT)Cl(PMe$_2$Ph) (I-1).

A solution of WO(CH-t-Bu)Cl$_2$(PMe$_2$Ph) (300.0 mg, 0.486 mmol) in 10 mL of benzene was mixed with a solution of HIPTOLi (247.1 mg, 0.489 mmol, 1.01 eq) in 5 mL of benzene. The cloudy, yellow reaction mixture was stirred at room temperature for 14 h. The solvent was removed in vacuo to give a yellow solid. The product was extracted to toluene (5 mL) and LiCl was removed by filtration through a bed of Celite. Toluene was removed in vacuo to yield a pale yellow crystalline solid. The product was triturated with pentane (5 mL) and the resulting suspension was filtered. Off-white solid was collected (280.2 mg, 60% yield). Two isomers in 61:39 ratio formed according to NMR spectra; only non-overlapping alkylidene signals are listed: Major isomer $^1$H NMR (C$_6$D$_6$) δ 9.36 (d, 1, WCH-t-Bu, $^3$J$_{HP}$=3 Hz, $^2$J$_{HW}$=11 Hz); $^{13}$C NMR (C$_6$D$_6$) δ 292.4 (d, WCH-t-Bu, $^1$J$_{CH}$=123 Hz, $^2$J$_{CP}$=12 Hz, $^1$J$_{CW}$=163 Hz); $^{31}$P NMR (C$_6$D$_6$): δ 12.89 (s, $^1$J$_{PW}$=420 Hz). Minor isomer: $^1$H NMR (C$_6$D$_6$): δ 8.89 (d, 1, WCH-t-Bu, $^3$J$_{HP}$=3 Hz, $^2$J$_{HW}$=13 Hz); $^{13}$C{$^1$H}NMR (C$_6$D$_6$): δ 278.7 (d, WCH-t-Bu, $^1$J$_{CH}$=117 Hz, $^2$J$_{CP}$=16 Hz, $^1$J$_{CW}$=188 Hz); $^{31}$P NMR (C$_6$D$_6$): δ 16.15 (s, $^1$J$_{PW}$=379 Hz). Anal. Calcd for C$_{49}$H$_{70}$ClO$_2$PW: C, 62.52; H, 7.50. Found: C, 62.31; H, 7.49.

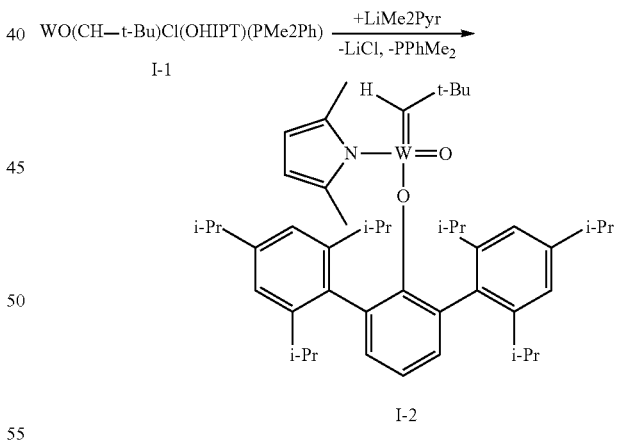

Figure 2:
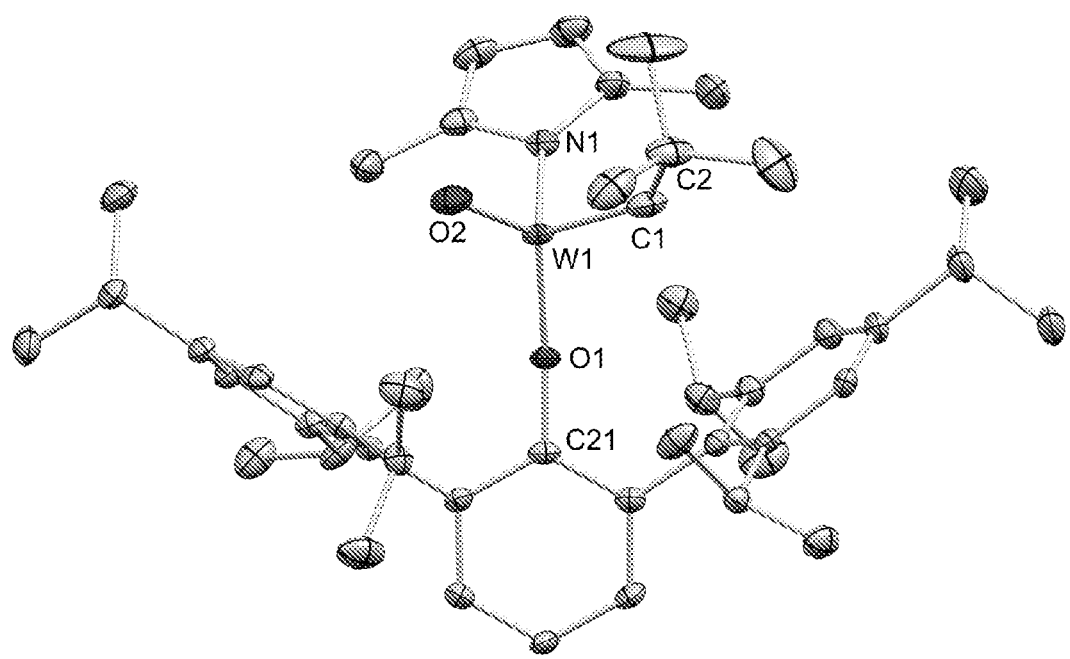
FIG. 2. Thermal ellipsoid drawing (50% probability) of syn-W(O)(CH-t-Bu)(OHIPT) (Me$_2$Pyr) (I-2). Hydrogen atoms have been omitted for clarity. Selected bond distances (Å) and angles (°): W1-C1=1.886(3), W1-O2=1.695(3), W1-O1=1.868(2), W1-N1=2.001(2), W1-O1-C21=166.9(2), W1-C1-C2=136.7(3).

Treatment of I-1 with Li(Me$_2$Pyr) in benzene at 60° C. for 16 h led to formation of yellow W(O)(CH-t-Bu)(OHIPT)(Me$_2$Pyr) (I-2) in 80% isolated yield. An X-ray structure (FIG. 2) showed I-2 to have a pseudotetrahedral geometry, a syn alkylidene, and an η$^1$-Me$_2$Pyr ligand.

Synthesis of WO(CH-t-Bu)(Me$_2$Pyr)(HIPTO) (I-2).

A portion of Li(Me$_2$Pyr) (56.4 mg, 0.558 mmol, 1.02 eq.) was added as a solid to a solution of WO(CH-t-Bu)(HIPTO)Cl(PMe$_2$Ph) (515.0 mg, 0.547 mmol) in 10 mL of benzene. The reaction mixture was transferred to a solvent Schlenk-type flask equipped with a Teflon valve, degassed, and heated at 60° C. for 16 h with rapid stirring. The color of the solution changed from pale- to bright-yellow. The volatiles were removed by heating at 60° C. in vacuo. Resulting yellow solid was triturated with 5 mL of benzene and LiCl was removed by filtration through a bed of Celite. Benzene was removed in vacuo leaving a bright-yellow solid. The product was triturated with 5 mL of pentane and filtered. The filtrate was left in a refrigerator at −30° C. for 1 day to give yellow crystalline solid. Two crops were combined (378.2 mg, 80% yield): $^1$H NMR (C$_6$D$_6$) δ 9.40 (s, 1, WCH-t-Bu, $^2J_{HW}$=10 Hz), 7.25 (m, 2, Ar—H), 7.20 (m, 2, Ar—H), 7.12 (d, 2, Ar—H), 6.91 (t, 1, Ar—H), 5.99 (s, 2, Pyr-H), 2.85 (overlapping sept, 6, CHMe$_2$), 1.94 (s, 6, Pyr-Me), 1.30 (d, 6, CHMe$_2$), 1.29 (d, 6, CHMe$_2$), 1.29 (d, 6, CHMe$_2$), 1.21 (s, 9, WCH-t-Bu), 1.17 (overlapping d, 12, CHMe$_2$), 1.10 (d, 6, CHMe$_2$); $^{13}$C{$^1$H}NMR (C$_6$D$_6$) δ 274.4 (WCH-t-Bu, $^1J_{CH}$=125 Hz, $^1J_{CW}$=155 Hz), 158.1, 149.1, 147.3, 146.9, 132.9, 131.9, 131.1, 123.2, 121.9, 121.7, 110.8, 43.1, 33.9, 31.4, 31.3, 25.7, 24.5, 24.5, 24.4, 24.3, 18.4. Anal. Calcd for C$_{47}$H$_{67}$NO$_2$W: C, 65.50; H, 7.84; N, 1.63. Found: C, 65.30; H, 7.78; N, 1.60.

TABLE 3

Crystal data and structure refinement data for WO(CH—t-Bu)(Me$_2$Pyr)(HIPTO) (I-2).

| | |
|---|---|
| Identification code | x11080 |
| Empirical formula | C$_{47}$H$_{67}$NO$_2$W |
| Formula weight | 861.87 |
| Temperature | 100(2) K |
| Wavelength | 0.71073 Å |
| Crystal system | Monoclinic |
| Space group | P2$_1$/n |
| Unit cell dimensions | a = 14.7275(18) Å   α = 90°. |
| | b = 15.986(2) Å   β = 110.046(2)°. |
| | c = 19.325(2) Å   γ = 90°. |
| Volume | 4274.1(9) Å$^3$ |
| Z | 4 |
| Density (calculated) | 1.339 Mg/m$^3$ |
| Absorption coefficient | 2.739 mm$^{-1}$ |
| F(000) | 1784 |
| Crystal size | 0.30 × 0.20 × 0.05 mm$^3$ |
| Theta range for data collection | 1.51 to 30.32°. |
| Index ranges | −20 <= h <= 20, −22 <= k <= 22, −26 <= l <= 27 |
| Reflections collected | 89374 |
| Independent reflections | 12819 [R(int) = 0.0624] |
| Completeness to theta = 30.32° | 100.0% |
| Absorption correction | Semi-empirical from equivalents |
| Max. and min. transmission | 0.8752 and 0.4938 |
| Refinement method | Full-matrix least-squares on F$^2$ |
| Data/restraints/parameters | 12819/739/524 |
| Goodness-of-fit on F$^2$ | 1.076 |
| Final R indices [I > 2sigma(I)] | R1 = 0.0333, wR2 = 0.0754 |
| R indices (all data) | R1 = 0.0413, wR2 = 0.0775 |
| Largest diff. peak and hole | 1.917 and −1.870 e · Å$^{-3}$ |

The analogous reaction between W(O)(CH-t-Bu)(PMe$_2$Ph)$_2$Cl$_2$ and LiOHMT (OHMT=O-2,6-dimesitylphenoxide) in benzene at 22° C. for 3 h led to isolation of off-white WO(CH-t-Bu)Cl(OHMT)(PMe$_2$Ph) (I-3) in 70% yield. As with I-1, the $^1$H NMR spectrum of the product contains two alkylidene doublet resonances that correspond to two isomers of I-3 in 87:13 ratio. The values of $^1J_{CH}$, 122 and 116 Hz, suggest that both isomers are syn alkylidenes.

Synthesis of WO(CH-t-Bu)(HMTO)Cl(PMe$_2$Ph) (I-3).

A solution of WO(CH-t-Bu)Cl$_2$(PMe$_2$Ph) (1000.0 mg, 1.620 mmol) in 15 mL of benzene was added to a portion of solid HMTOLi (572.3 mg, 1.701 mmol, 1.05 eq). The cloudy, yellow reaction mixture was stirred at room temperature for 3 h. The solvent was removed in vacuo to give a yellow solid. The product was extracted to toluene (10 mL) and LiCl was removed by filtration through a bed of Celite. Toluene was removed in vacuo to produce a yellow crystalline solid. The product was triturated with pentane (10 mL) and the resulting suspension was filtered. Yellow solid product was collected (872.0 mg, 1.128 mmol, 70% yield). Two isomers in a 87:13 ratio formed according to NMR spectra; only non-overlapping alkylidene signals are listed: Major isomer $^1$H NMR (C$_6$D$_6$) δ 9.34 (d, 1, WCH-t-Bu, $^3J_{HP}$=3 Hz, $^2J_{HW}$=8 Hz); $^{13}$C NMR (C$_6$D$_6$): δ 295.1 (d, WCH-t-Bu, $^1J_{CH}$=122 Hz, $^2J_{CP}$=11 Hz, $^1J_{CW}$=168 Hz); $^{31}$P NMR (C$_6$D$_6$): δ 13.40 (s, $^1J_{PW}$=416 Hz). Minor isomer $^1$H NMR (C$_6$D$_6$) δ 9.03 (d, 1, WCH-t-Bu, $^3J_{HP}$=3 Hz, $^2J_{HW}$=13 Hz); $^{13}$C{$^1$H}NMR (C$_6$D$_6$): δ 278.6 (d, WCH-t-Bu, $^1J_{CH}$=116 Hz, $^2J_{CP}$=15 Hz, $^1J_{CW}$=187 Hz); $^{31}$P NMR (C$_6$D$_6$): δ 15.64 (s, $^1J_{PW}$=386 Hz). Anal. Calcd for C$_{37}$H$_{46}$ClO$_2$PW: C, 57.49; H, 6.00. Found: C, 57.52; H, 5.99.

In some embodiments, synthesis of WO(CH-t-Bu)(HMTO)Cl(PMe$_2$Ph) (I-3) can also be performed by reacting compound WO(CH-t-Bu)Cl$_2$(PMe$_2$Ph) with one equivalent of HMTOLi (HMTO=hexamethylterphenoxide) in toluene at room temperature to yield WO(CH-t-Bu)(HMTO)Cl (PMe$_2$Ph). The $^1$H NMR spectrum of the product contains two alkylidene proton doublets that correspond to two isomers of I-3 in 87:13 ratio. The values of $^1J_{CH}$, 122 and 166 Hz, suggest that both species are syn alkylidenes.

Figure 3:
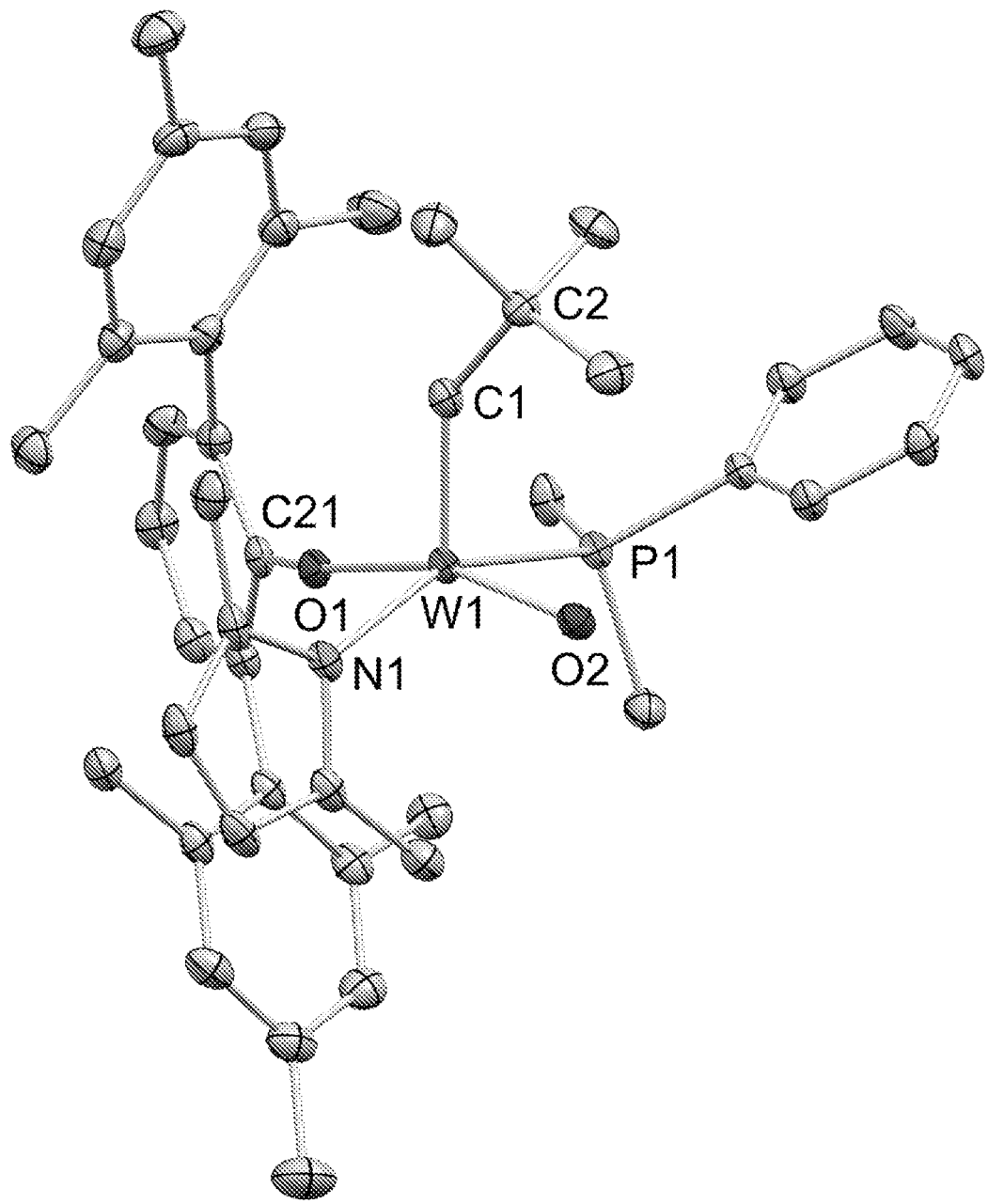
FIG. 3. Thermal ellipsoid drawing (50% probability) of syn-W(O)(CH-t-Bu)(OHMT) (Me$_2$Pyr)(PMe$_2$Ph) (I-4). Hydrogen atoms have been omitted for clarity. Solvent molecules are not shown. Selected bond distances (Å) and angles (°): W1-C1=1.900(3), W1-O2=1.717(2), W1-O1=1.964(2), W1-N1=2.074(2), W1-P1=2.580(1), W1-O1-C21=159.8(2), W1-C1-C2=141.0(2).
Figure 4:
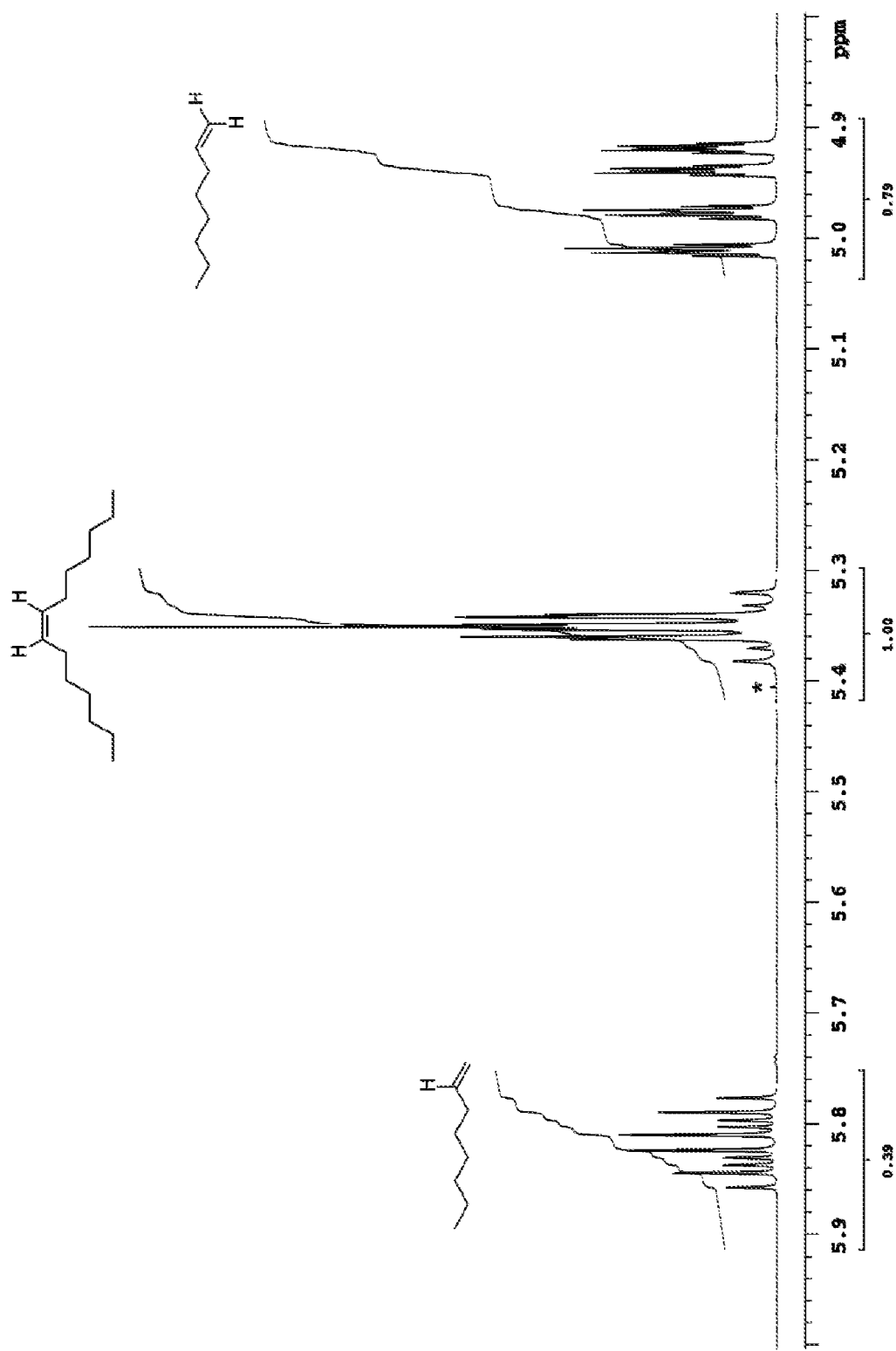
FIG. 4. Typical $^1$H NMR spectrum of the product of 1-octene homocoupling mixture. Olefinic region of $^1$H NMR (in CDCl$_3$) spectrum of a crude product of 1-octene homocoupling promoted by I-4. No trans-product (at ~5.38 ppm) can be observed. The asterisk denotes residual ethylene.

Addition of Li(Me$_2$Pyr) to I-3 in toluene at −30° C. with subsequent stirring at 22° C. for 10 h led to yellow W(O)(CH-t-Bu)(OHMT)(Me$_2$Pyr)(PMe$_2$Ph) (I-4) in 70% isolated yield. An X-ray structure of I-4 (FIG. 3) showed it to be a square pyramid with the syn neopentylidene in the apical position and the phosphine bound trans to the pyrrolide.

Synthesis of WO(CH-t-Bu)(Me$_2$Pyr)(HMTO)(PMe$_2$Ph) (I-4).

A portion of Li(Me$_2$Pyr) (86.3 mg, 0.854 mmol, 1.1 eq.) was added as a solid to a cold (−30° C.) solution of WO(CH-t-Bu)(HMTO)Cl(PMe$_2$Ph) (600.0 mg, 0.776 mmol) in 15 mL of toluene. The reaction mixture was stirred at room temperature for 10 h. Toluene was removed in vacuo. Resulting brown oil was triturated with 5 mL of toluene and LiCl was removed by filtration through a bed of Celite. Toluene was removed in vacuo leaving brown oil. The product was triturated with 5 mL of pentane causing precipitation of pale yellow solid. The product was filtered and washed with 5 mL of cold pentane. The filtrate was reduced in volume to ca. 3 mL and left in a refrigerator at −30° C. for 1 day giving yellow crystals. Two crops were combined (452 mg, 70% yield): $^1$H NMR (48 mM in C$_6$D$_6$) δ 9.14 (broad s, 1, WCH-t-Bu), 7.30 (m, 2, PMe$_2$Ph), 7.05 (m, 3, PMe$_2$Ph), 7.00 (m, 2, Ar—H), 6.88 (m, 5, Ar—H), 6.10 (s, 2, Pyr-H), 2.20 (s, 6, Pyr-Me), 2.08 (overlapping singlets, 18, Ar-Me), 1.11 (s, 6, PMe$_2$Ph), 1.02 (s, 9, WCH-t-Bu); $^{13}$C{$^1$H}NMR (48 mM C$_6$D$_6$): δ 278.9 (broad, WCH-t-Bu), 158.5, 140.1, 137.6, 137.1, 136.7, 134.6, 131.9, 131.0, 130.9, 130.6, 129.3, 129.0, 128.6, 128.5, 128.4, 125.4, 125.2, 125.0, 122.5, 109.9, 43.6, 32.6, 21.4, 21.2, 20.7, 17.5. $^{31}$P NMR (48 mM C$_6$D$_6$): δ −25.5 (broad s); $^1$H NMR (20 mM in CD$_2$Cl$_2$, −30° C.) δ 9.92 (broadened s, 1, WCH-t-Bu), 7.48 (m, 2, PMe$_2$Ph), 7.41 (m, 3, PMe$_2$Ph), 6.94 (m, 7, Ar—H), 5.70 (s, 1, Pyr-H), 5.66 (s, 1 Pyr-H), 2.37 (s, 3, Ar-Me), 2.34 (s, 3, Ar-Me), 2.29 (s, 3, Ar-Me), 2.23 (s, 3, Ar-Me), 1.93 (s, 3, Ar-Me), 1.88 (s, 3, Ar-Me), 1.62 (s, 3, Pyr-Me), 1.54 (m, 6, PMe$_2$Ph), 1.30 (s, 3, Pyr-Me), 0.52 (s, 9, WCH-t-Bu); $^{13}$C{$^1$H}NMR (20 mM in CD$_2$Cl$_2$, −30° C.): δ 293.16 (WCH-t-Bu, $^1J_{CH}$=125 Hz), 160.0, 139.3, 138.6, 136.7 (d), 135.0, 134.8, 134.3, 134.0, 133.5, 131.8, 131.6, 131.2, 130.6, 130.5 (d), 130.4, 130.1, 129.4, 129.2, 128.6 (d), 128.2, 120.0, 107.3, 105.8, 44.0, 30.8, 21.9, 21.6, 21.4, 21.0, 20.6, 18.7, 18.8, 13.9 (d), 11.0 (d). $^{31}$P NMR (20 mM in CD$_2$Cl$_2$, −30° C.): δ −1.80 (s, $^1J_{PW}$=289 Hz). Anal. Calcd for C$_{43}$H$_{54}$NO$_2$PW: C, 62.10; H, 6.54; N, 1.68. Found: C, 61.95; H, 6.73; N, 1.43.

TABLE 4

Crystal data and structure refinement details for W(O)(OHMT)(CH—t-Bu)(Me$_2$Pyr)(PMe$_2$Ph) (I-4).

| | |
|---|---|
| Identification code | x11146 |
| Empirical formula | C$_{50.50}$H$_{72}$NO$_2$PW |
| Formula weight | 939.91 |
| Temperature | 100(2) K |
| Wavelength | 0.71073 Å |
| Crystal system | Triclinic |
| Space group | P-1 |
| Unit cell dimensions | a = 13.4162(7) Å    α = 71.8330(10)°. |
| | b = 13.5775(7) Å    β = 65.5150(10)°. |
| | c = 14.7782(8) Å    γ = 83.6550(10)°. |
| Volume | 2327.2(2) Å3 |
| Z | 2 |
| Density (calculated) | 1.341 Mg/m$^3$ |
| Absorption coefficient | 2.554 mm$^{-1}$ |
| F(000) | 974 |
| Crystal size | 0.07 × 0.02 × 0.02 mm$^3$ |
| Theta range for data collection | 1.58 to 30.32°. |
| Index ranges | $-19 <= h <= 19, -19 <= k <= 19,$ |
| | $-20 <= l <= 20$ |
| Reflections collected | 105170 |
| Independent reflections | 13947 [R(int) = 0.0684] |
| Completeness to theta = 30.32° | 99.9% |
| Absorption correction | Semi-empirical from equivalents |
| Max. and min. transmission | 0.9507 and 0.8415 |
| Refinement method | Full-matrix least-squares on F$^2$ |
| Data/restraints/parameters | 13947/75/541 |
| Goodness-of-fit on F$^2$ | 1.032 |
| Final R indices [I > 2sigma(I)] | R1 = 0.0287, wR2 = 0.0576 |
| R indices (all data) | R1 = 0.0380, wR2 = 0.0609 |
| Largest diff. peak and hole | 2.589 and −1.184 e · Å$^{-3}$ |

The PMe$_2$Ph ligand in I-4 is partially dissociated at room temperature and rapidly exchanging on and off the metal. The alkylidene resonance is broad and its chemical shift is concentration dependent (8.57-9.14 ppm for 4 mM-48 mM solutions in C$_6$D$_6$). Variable temperature $^1$H and $^{31}$P NMR studies of a 20 mM solution of I-4 in CD$_2$Cl$_2$ showed that the phosphine is "bound" below −30° C. as indicated by a sharp $^{31}$P signal corresponding to the coordinated ligand (1.80 ppm, $^1$J$_{PW}$=289 Hz). On the basis of the chemical shift for free and coordinated phosphine the value of the equilibrium constant for phosphine dissociation can be estimated as 0.015 M at room temperature. This value corresponds to 57% dissociation of phosphine in a 20 mM solution of I-4 in C$_6$D$_6$.

Both I-2 and I-4 react with ethylene to give an unsubstituted metallacyclobutane complex (and t-butylethylene) that has a square pyramidal structure (presumably with the oxo ligand in the apical position) on the basis of chemical shifts of metallacycle protons in the range 0.7-4.5 ppm (Feldman J.; Schrock, R. R. Prog. Inorg. Chem. 1991, 39, 1). With I-2 the reaction with ethylene is relatively slow and what we propose is an intermediate square pyramidal β-t-butylmetallacyclobutane complex can be observed before t-butylethylene is formed. In the case of compound I-4, a mixture of an unsubstituted square pyramidal metallacycle and a methylidene are readily formed upon addition of ethylene. In both systems the metallacycles slowly decompose over a period of 24 h to unidentified products. A square pyramidal metallacyclobutane made from imido alkylidenes has been proposed to be further away from the transition state for olefin loss than is the alternative TBP metallacycle (Feldman, J.; Davis, W. M.; Thomas, J. K.; Schrock, R. R. Organometallics 1990, 9, 2535).

Figure 6:
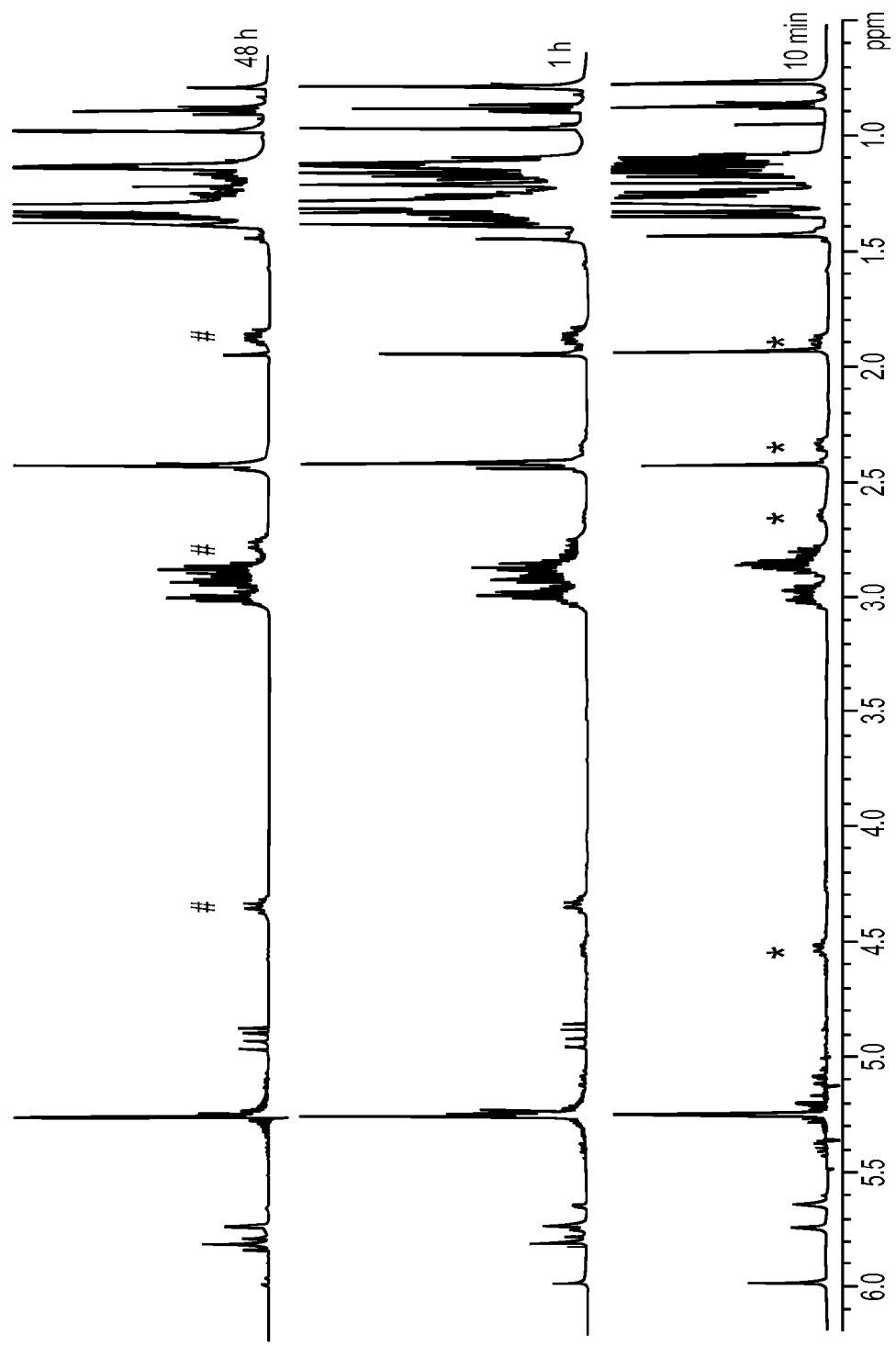
FIG. 6. $^1$H NMR spectra of WO(CH-t-Bu)(Me$_2$Pyr)(HIPTO) solution in C$_6$D$_6$ after addition of 1 atm of ethylene. Signals attributed to proposed substituted and unsubstituted metallacycles are labeled * and #, respectively.

Compound I-2 (0.01 M solution in C$_6$D$_6$) reacts with 1 atm of ethylene with a quick color change of the solution from yellow to red. In 10 min. approximately 50% of I-2 is converted to a square pyramidal metallacycle as evidenced by the appearance of multiplets in 4.6-1.8 ppm region (FIG. 6, bottom) (Feldman, J.; Davis, W. M.; Thomas, J. K.; Schrock, R. R. Organometallics 1990, 9, 2535). At the same time, no signal from 3,3-dimethyl-1-butene was observed. Therefore, it can be proposed that the substituted metallacycle is formed in the early stage of the reaction. The $^1$H NMR spectrum recorded after 1 h (FIG. 6, middle) showed almost complete disappearance of the metallacycle multiplets that were observed in the 10 min. spectrum and formation of 3,3-dimethyl-1-butene and the unsubstituted square pyramidal metallacyclobutane.

ROMP of DCMNBD.

In a nitrogen-filled glovebox, a solution of monomer (50.0 mg, 50 equiv) in 1.0 mL of toluene was added to a solution of a catalyst in 0.2 mL of toluene. The mixture was stirred for 4 h. Aliquots were taken and diluted with CDCl$_3$ to monitor reaction progress. After reaction completion, 0.5 mL of benzaldehyde was added on air and stirred for 30 min. The mixture was added dropwise to 50 mL of methanol with rapid stirring. A fine white solid formed immediately, and the mixture was stirred for 10 h. The polymer was filtered off on a glass frit and dried under vacuum.

Both I-2 and I-4 serve as initiators for the polymerization of 5,6-dicarbomethoxynorbornadiene (DCMNBD). The polymerization of 50 equiv of DCMNBD is relatively slow with I-2 and propagation is faster than initiation. The resulting polymer is >99% cis, 90% syndiotactic. The polymerization of 50 equiv of DCMNBD with I-4 is relatively fast and all initiator is consumed. The resulting polymer is >99% cis, 98% syndiotactic (Schrock, R. R.; Müller, P.; Hoveyda, A. H. J. Am. Chem. Soc. 2009, 131, 7962).

Compound I-2 reacts with DCMNBD in toluene slowly to yield >99% cis, 90% syndiotactic poly-DCMNBD. The polymerization of 50 equivalents of the monomer was complete in 90 min. Monitoring the reaction progress of in situ in CD$_2$Cl$_2$ by $^1$H NMR revealed that only 20% of the starting neopentylidene was consumed in 40 min.

Compound I-4 readily reacts with ethylene in benzene to form a metallacycle along with a methylidene complex in 1:1 ratio after 10 min. The metallacycle resonances are in 0.-4.5 ppm range, which suggests a square-pyramidal geometry. In case of I-4, however, 3.3-dimethylbutene formed rapidly, indicating that only the unsubstituted tungstacyclobutane was present. Both the metallacycle and the methylidene decomposed within 1 h in benzene.

Terminal Olefin Homocoupling.

In a nitrogen-filled glovebox, neat substrate (200 mg) was added to a solid catalyst in 1 dram vial. The vial was placed in 20 mL scintillation vial and sealed. The reaction mixture was stirred at 22° C. and aliquots were sampled. The aliquots were quenched outside a box by exposure to air and addition of CDCl$_3$. The conversion and selectivity of the reactions were monitored by $^1$H NMR.

Homocoupling of neat terminal olefins with I-2 takes place slowly (hours) at room temperature. In contrast, I-4 was found to be a highly active and highly Z-selective (Table 5). A catalyst loading as low as 0.2 mol % yielded up to 88% conversion in 6 h for several of the six chosen substrates. No trans product could be observed in $^1$H NMR spectra of the Z products.

TABLE 5

Conversions to Z-selective Metathesis Homocoupling Products of Neat Terminal Olefins Promoted by I-4.[a]

| | substrate/cat loading (mol %); >99% Z product in each case. | | | | | |
|---|---|---|---|---|---|---|
| time | S1/ 0.2% | S2/ 0.2% | S3/ 0.2% | S4/ 0.2% | S5/ 0.2% | S6/ 1% |
| 10 min | 28% | 44% | 65% | — | 28% | — |
| 30 min | 39% | 67% | 75% | — | 39% | — |

TABLE 5-continued

Conversions to Z-selective Metathesis Homocoupling Products of Neat Terminal Olefins Promoted by I-4.[a]

| time | S1/ 0.2% | S2/ 0.2% | S3/ 0.2% | S4/ 0.2% | S5/ 0.2% | S6/ 1% |
|---|---|---|---|---|---|---|
| | | | substrate/cat loading (mol %); >99% Z product in each case. | | | |
| 1 h | 47% | 79% | 75% | 2% | 47% | 10% |
| 6 h | 66% | 86% | — | — | 73%[b] | — |
| 24 h | 72% | 88% | — | 11% | — | 59% |

[a] S1 = 1-octene, S2 = allylbenzene, S3 = allylboronic acid pinacolate ester, S4 = allylSiMe$_3$, S5 = 1-decene, S6 = Methyl-10-undecenoate.
[b] The aliquot was taken after 7 h.

Clearly formation of the Z product is highly selective. Only a small increase in conversion was found for longer (>6 h) reaction times, which suggests that the majority of the catalyst has decomposed at this stage. Decomposition of a catalyst prior to isomerization of the Z product to E can be a desirable feature of the coupling reaction. The reactions were run on a 200 mg scale in a closed vessel with a volume of ~20 mL. Homocoupling of 1-decene under 0.5 Torr vacuum did not show a significant increase in turnover compared to the reaction carried out under 1 atm of nitrogen. Without wishing to be bound by any particular theory, we ascribe the relatively low turnover in the case of allylTMS (S4) to steric issues, and in the case of methyl-10-undecenoate (S6, at 1% catalyst loading) to ester binding to W.

Results of homocoupling (HC) of 1-octene to 5-decene catalyzed by I-2 are shown in Table 6. The rate of the reaction is higher in comparison to the recently reported analogous W(NAr)(C$_3$H$_6$)(3,5-Me$_2$Pyr)(HIPTO) catalyst (32% conversion in 16 h, 4 mol % catalyst loading) (Marinescu, S. C; Schrock, R. R.; Müller, P.; Takase, M. K.; Hoveyda, A. H. *Organometallics*, 2011, 30, 1780). Z-selectivity was found to be only 70-72% and declined as the reaction progressed.

TABLE 6

Homocoupling of 1-octene in the presence of I-2.

| time, h | solution in benzene, 4 mol % cat. | neat, 2 mol % cat. | neat, 0.2 mol % cat. |
|---|---|---|---|
| 0.67 | — | 2% conv., 75% cis | <1% conv., 75% cis |
| 2 | 15% conv., 70% cis | — | — |
| 4 | 26% conv., 72% cis | 24% conv., 57% cis | 4% conv., 70% cis |
| 8 | 34% conv., 70% cis | — | — |
| 48 | 68% conv., 52% cis | — | — |

Compound I-4 was found to be an excellent catalyst for ROMP and HC of terminal olefins reactions. For instance, polymerization of 50 equivalents of DCMNBD was complete in less than 10 min and the isolated polymer for found to be all-cis and 98% syndiotactic. The results of homocoupling of terminal olefins at room temperature with 4 mol % catalyst loading are listed in Table 7. The reactions are rapid with high conversion being achieved within 3 h. The products are >98% cis, i.e., no trans product could be observed in $^1$H NMR spectra. Little change in conversion was found after longer (>10 h) reaction times, which suggests that the catalyst decomposes with time. Without wishing to be bound by any particular theory, since isomerization of a Z-product is believed to be the main reason for a decay of Z-selectivity with reaction time for tungsten imido alkylidenes (Jiang, A. J.; Zhao, Y.; Schrock, R. R.; Hoveyda, A. H. *J. Am. Chem. Soc.*

2009 131 16630), decomposition of a catalyst prior to the point when such side reaction is likely to occur can be, in fact, desirable.

TABLE 7

Homocoupling of terminal olefins in benzene in presence of 4 mol % of I-4.

| substrate | catalyst | time | % cis | % conv. |
|---|---|---|---|---|
| 1-octene | I-4 | 1 min | >98 | 32 |
| | | 10 min | >98 | 41 |
| | | 1 h | >98 | 66 |
| | | 4 h | >98 | 81 |
| | | 10 h | >98 | 88 |
| | I-4 + 2 B(C$_6$F$_5$)$_3$ | 1 min | 33 | 82 |
| | | 10 min | 21 | 93 |
| Allylboronic acid pinacol ester | I-4 | 10 min | >98 | 19 |
| | | 1 h | >98 | 41 |
| | | 3 h | >98 | 49 |
| | I-4 + 2 B(C$_6$F$_5$)$_3$ | 10 min | 71 | 80 |
| | | 1 h | 53 | 93 |
| Allyltrimethylsilane | I-4 | 14 h | >98 | 32 |
| Allylbenzene | I-4 | 1 h | >98 | 85 |
| | | 3 h | >98 | 91 |
| Methyl-10-undecenoate | I-4 | 1 h | >98 | 79 |
| | | 3 h | >98 | 91 |
| Allylcyclohexane | I-4 | 1 h | 94 | 24 |
| | | 3 h | 87 | 42 |

The homocoupling of neat 1-octene catalyzed by I-4 led to analogously high conversion and Z-selectivity for lower catalyst loadings (as low as 0.2 mol %, see Table 8). For example, 72% conversion was achieved in 24 h.

TABLE 8

Homocoupling of neat 1-octene in presence of I-4.

| time, h | neat, 1 mol % cat. | neat, 0.2 mol % cat. |
|---|---|---|
| 0.17 | 62% conv., >98% cis | 28% conv., >98% cis |
| 0.5 | 63% conv., >98% cis | 39% conv., >98% cis |
| 1 | 69% conv., >98% cis | 47% conv., >98% cis |
| 6 | — | 66% conv., >98% cis |
| 24 | — | 72% conv., >98% cis |

The reactivity of I-2 in both HC and ROMP reactions in presence of Lewis acids was studied. It was found that the presence of either B(C$_6$H$_5$)$_3$ or B(C$_6$F$_5$)$_3$ greatly improve the reaction rates. The results of the homocoupling of 1-octene in benzene solution as well as in the neat substrate are summarized in Tables 9 and 10. Addition of one equivalent of strong Lewis acid B(C$_6$F$_5$)$_3$ dramatically increases the reactivity of tungsten oxo alkylidene complex (78% conversion in 15 min with 4 mol % catalyst loading: compare to 15% conversion for I-2 in 2 h in similar conditions). The Z-selectivity declined. At the same time, addition of one equivalent of milder Lewis acid B(C$_6$H$_5$)$_3$ led to increased reactivity while Z-selectivity of the catalyst was preserved.

TABLE 9

Homocoupling of 1-octene solution in benzene in the presence of I-2 with a Lewis acid added.

| time, h | I-2 + B(C$_6$H$_5$)$_3$, 4 mol % | I-2 + B(C$_6$F$_5$)$_3$, 4 mol % |
|---|---|---|
| 0.25 | — | 78% conv., 48% cis |
| 0.67 | 23% conv., 72% cis | — |
| 2 | 29% conv., 70% cis | — |
| 4 | 38% conv., 57% cis | — |

TABLE 10

Homocoupling of neat l-octene in the presence of I-2 with one
equivalent of a Lewis acid added.

| time, h | I-2 + B(C$_6$F$_5$)$_3$, 2 mol % | I-2 + B(C$_6$H$_5$)$_3$, 0.2 mol % | I-2 + B(C$_6$F$_5$)$_3$, 0.2 mol % |
|---|---|---|---|
| 0.67 | 82% conv., 35% cis | 18% conv., 68% cis | 56% conv., 59% cis |
| 4 | 90% conv., 20% cis | 38% conv., 60% cis | 88% conv., 44% cis |

ROMP of DCMNBD catalyzed by I-2 is significantly accelerated in presence of Lewis acids. Polymerization of 50 equivalents of the monomer was found to be complete in less than 25 min with 40 equivalents of DCMNBD consumed in 10 min when one equivalent of B(C$_6$F$_5$)$_3$ was added to I-2. In the same conditions, only six equivalents of the monomer reacted with I-2 without presence of LA. The initiation reaction remains slow in the presence of B(C$_6$F$_5$)$_3$ (it was found that only 8-10% of starting neopentylidene reacted with the monomer); however, the rate of propagation increases dramatically. It is possible that a stronger Lewis acid adduct is formed with the insertion product than with the sterically crowded neopentylidene initiator, thus increasing the rate of propagation. Interestingly, high activity of I-2+B(C$_6$F$_5$)$_3$ was observed even in the presence of a large excess of monomer bearing Lewis base sites, probably due to higher basicity of tungsten oxo alkylidene.

Similar results were obtained when B(C$_6$H$_5$)$_3$ was used as an additive. In the first 10 min of the reaction, 10 equivalents of the monomer were consumed. It was found that 20-25% of I-2 reacted in 60 min.

Figure 7:
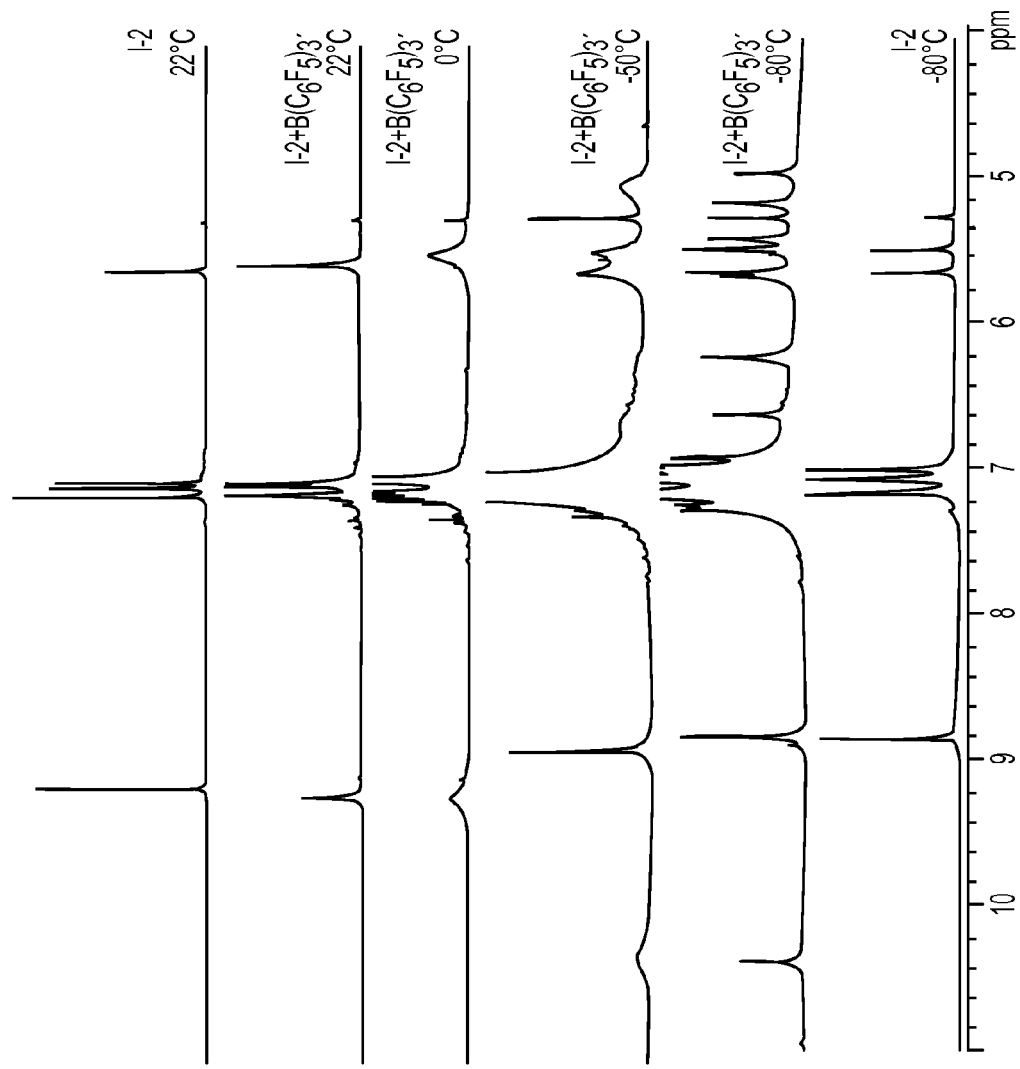
FIG. 7. Variable temperature 1H NMR spectra of I-2 and the mixture of I-2 and B(C$_6$F$_5$)$_3$.

Variable temperature (VT) $^1$H NMR study of the mixture of I-2 and 0.5 equivalents of B(C$_6$F$_5$)$_3$ in CD$_2$Cl$_2$ showed that the LA adduct formation can be observed at low temperatures (FIG. 7). The alkylidene peak broadens and shifts downfield with cooling from 22° C. to –30° C. At –50° C., two peaks, one broad at 10.38 ppm and one sharper at 8.86 ppm, are observed in alkylidene region. The two alkylidene peaks become sharper at –80° C. This change is accompanied by the appearance of eight peaks in the aromatic pyrrolide region. The $^1$H NMR of I-2 in CD$_2$Cl$_2$ at –80° C. showed that the alkylidene signal at 8.86 ppm as well as two pyrrolide proton signals belong to the LA-free MAP (FIG. 7 bottom). It is possible that formation of the LA adduct can lead to the stabilization of η$^5$ coordination mode of pyrrolide at low temperatures to compensate for electron density deficiency on the metal center.

Addition of Lewis acids to I-4 significantly speeds up metathesis reactions. For example, addition of B(C$_6$F$_5$)$_3$ to I-4 resulted in a 90% conversion in 1 h for 1-octene homo-coupling with 0.2 mol % catalyst loading. The homocoupling metathesis reaction yields the thermodynamic mixture (20% Z). Table 7 presented more data.

Figure 5:
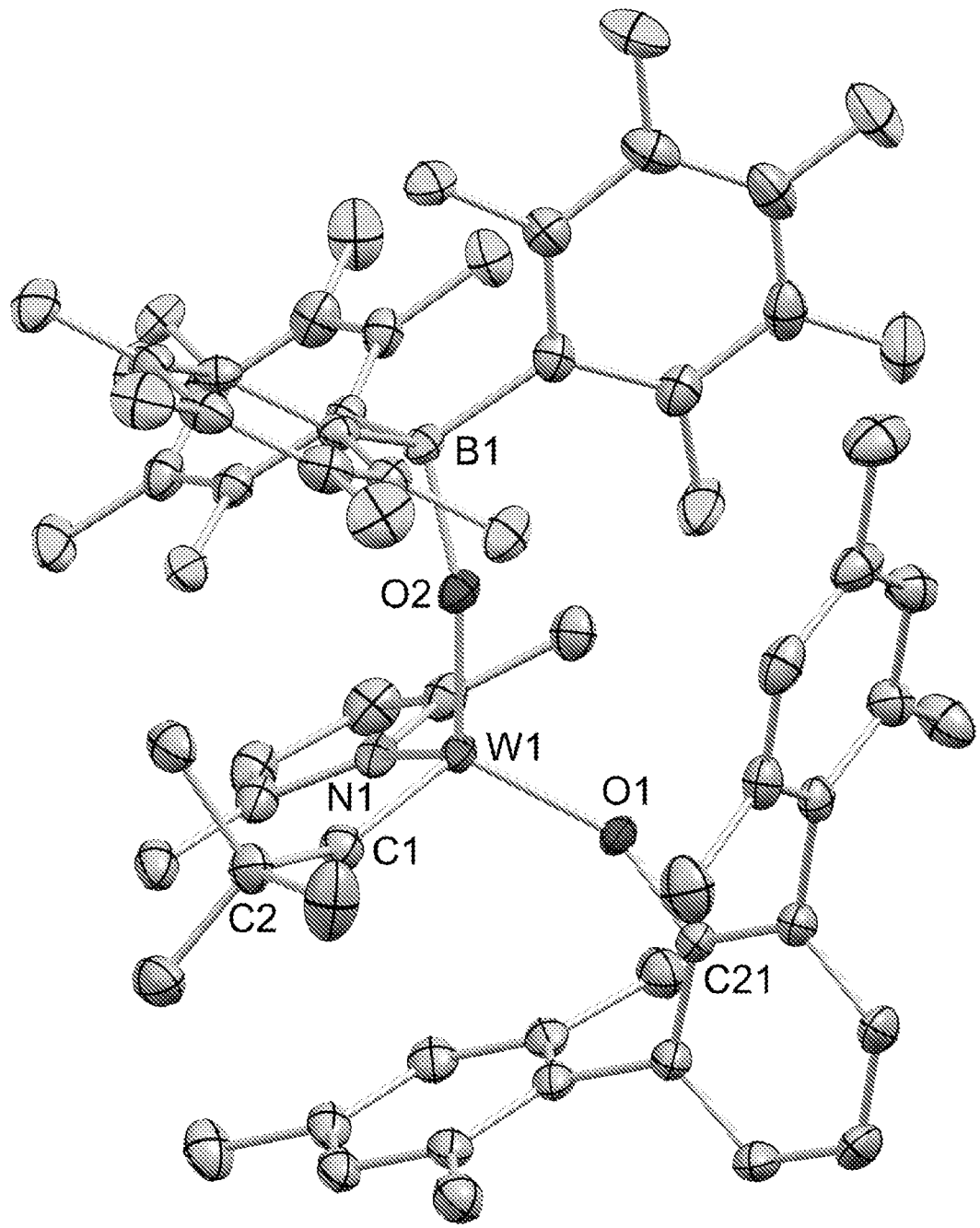
FIG. 5. Thermal ellipsoid drawing (50% probability) of W(O)(B(C$_6$F$_5$)$_3$)(CH-t-Bu)(OHMT)(Me$_2$Pyr) (I-6). Hydrogen atoms have been omitted for clarity. Selected bond distances (Å) and angles (°): W1-C1=1.868(2), W1-O2=1.759(2), W1-O1=1.860(2), W1-N1=1.968(2), B1-O2=1.571(3), W1-O1-C21=150.9(1), W1-C1-C2=155.4(2)

Addition of two equivalents of B(C$_6$F$_5$)$_3$ to I-4 led to formation of (Me$_2$PhP)(B(C$_6$F$_5$)$_3$) and I-6. The Lewis acid in I-6 is labile at room temperature as demonstrated by a broadened alkylidene signal in the 1H NMR spectrum at 7.30 ppm. The $^1$H NMR spectrum of 45 mM adduct solution at –60° C. shows a sharp alkylidene resonance at 7.06 ppm. An X-ray structure of I-6 showed that B(C$_6$F$_5$)$_3$ is coordinated to the oxo ligand (FIG. 5). The W1-O2-B1 unit is bent (W1-O2-B1 angle is 159.9(1)°). The W1-O2 distance is elongated (1.759 (2) Å) relative to that in I-4 (1.717(2) Å) or in I-2 (1.695(3) Å) and is slightly shorter than in reported B(C$_6$F$_5$)$_3$ adducts of tungsten oxo complexes (Barrado, G.; Doerrer, L.; Green, M. L. H.; Leech, M. A. *J. Chem. Soc., Dalton Trans.* 1999, 1061; Galsworthy, J. R.; Green, J. C.; Green, M. L. H.; Müller, M. *J. Chem. Soc., Dalton Trans.* 1998, 15; Wolff, F.; Choukroun, R.; Lorber, C.; Donnadieu, B. *Eur. J. Inorg. Chem.* 2003, 628; Sinchez Nieves, J.; Royo, P.; Mosquera, M. E. G. *Eur. J. Inorg. Chem.* 2006, 127). A relatively weak coordination of B(C$_6$F$_5$)$_3$ to the oxo is also indicated by the B1-O2 bond length (1.571(3) Å), which is longer than in any B(C$_6$F$_5$)$_3$ adducts of transition metal oxo complexes (1.484(3)-1.558 (2) Å) in the literature. The average values of the C-B-C and O-B-C angles (112.6° and 106.1°, respectively) also suggest that B(C$_6$F$_5$)$_3$ is relatively weakly coordinated to the oxo.

Synthesis of W(O)(B(C$_6$F$_5$)$_3$)(CH-t-Bu)(OHMT)(Me$_2$Pyr) (I-6).

A cold (–30° C.) suspension of B(C$_6$F$_5$)$_3$ (37.3 mg, 0.073 mmol, 2.02 eq.) in 2 mL pentane was added to a cold (–30° C.) suspension of WO(CH-t-Bu)(Me$_2$Pyr)(HMTO)(PMe$_2$Ph) (30.0 mg, 0.036 mmol) in 5 mL of pentane with rapid stirring. The color of the mixture changed from yellow to orange and white precipitate gradually formed. The solvent volume was reduced to ca. 3 mL and the mixture was filtered. The volume of orange filtrate was reduced to ca. 1 mL and the solution was placed in the freezer at –30° C. In three days, orange crystals formed. NMR signals are listed for 45 mM solution of I-4.B (C$_6$F$_5$)$_3$ in CD$_2$Cl$_2$ at –60° C., generated in situ from WO(CH-t-Bu)(Me$_2$Pyr)(HMTO)(PMe$_2$Ph) and 2.02 equiv B(C$_6$F$_5$)$_3$): $^1$H NMR δ 7.06 (s, 1, WCH-t-Bu, $^3$J$_{WH}$=17 Hz), 7.26 (t, 1, Ar—H), 7.12 (d, 2, Ar—H), 6.93 (s, 2, Ar—H), 6.57 (s, 2, Ar—H), 5.76 (broadened s, 1, Pyr-H), 5.44 (broadened s, 1, Pyr-H), 2,11 (s, 6, Ar-Me), 2.05 (s, 6, Ar-Me), 1.89 (s, 6, Ar-Me), 1.86 (s, 3, Pyr-Me), 1.54 (s, 3, Pyr-Me), 0.89 (s, 9, WCH-t-Bu); $^{13}$C{$^1$H}NMR: δ 274.2 (WCH-t-Bu, $^1$J$_{CH}$=115 Hz), 157.8, 147.8, 145.9, 137.3, 135.5, 135.3, 131.4, 130.9, 128.3, 128.2, 125.8, 115.0, 112.3, 110.7, 49.7, 31.7, 21.2, 20.7, 20.6, 17.4, 12.8. $^{19}$F NMR: –135.2 (broad, 1), –136.3 (broad, 1), –161.1 (broad, 1), –165.6 (broad, 1), –166.7 (broad, 1). $^{11}$B NMR: –3 (very broad).

TABLE 11

Crystal data and structure refinement details for W(O)(CH—t-Bu)(B(C$_6$F$_5$)$_3$(OHMT)(Me$_2$Pyr) (I-6).

| | |
|---|---|
| Identification code | x11151 |
| Empirical formula | C$_{53}$H$_{43}$BF$_{15}$NO$_2$W |
| Formula weight | 1205.54 |
| Temperature | 100(2) K |
| Wavelength | 0.71073 Å |
| Crystal system | Monoclinic |
| Space group | P2$_1$/n |
| Unit cell dimensions | a = 13.2954(11) Å   α = 90°. |
| | b = 21.6218(18) Å   β = 93.976(2)°. |
| | c = 16.9582(15) Å   γ = 90°. |
| Volume | 4863.2(7) Å$^3$ |
| Z | 4 |
| Density (calculated) | 1.647 Mg/m$^3$ |
| Absorption coefficient | 2.476 mm$^{-1}$ |
| F(000) | 2392 |
| Crystal size | 0.21 × 0.05 × 0.04 mm$^3$ |
| Theta range for data collection | 1.80 to 30.32° |
| Index ranges | –18 <= h <= 18, –30 <= k <= 30, –24 <= l <= 24 |
| Reflections collected | 116266 |
| Independent reflections | 14569 [R(int) = 0.0508] |
| Completeness to theta = 30.32$_i$ | 99.9% |
| Absorption correction | Semi-empirical from equivalents |
| Max. and min. transmission | 0.9184 and 0.6244 |
| Refinement method | Full-matrix least-squares on F$^2$ |
| Data/restraints/parameters | 14569/1/672 |
| Goodness-of-fit on F$^2$ | 1.027 |
| Final R indices [I > 2sigma(I)] | R1 = 0.0262, wR2 = 0.0529 |
| R indices (all data) | R1 = 0.0391, wR2 = 0.0574 |
| Largest diff. peak and hole | 0.800 and –1.005 e · Å$^{-3}$ |

In some embodiments, compounds I-7, I-8, and I-9 are prepared from reacting WO(CH-t-Bu)Cl$_2$(PMe$_2$Ph)$_2$ with lithium pyrrolides:

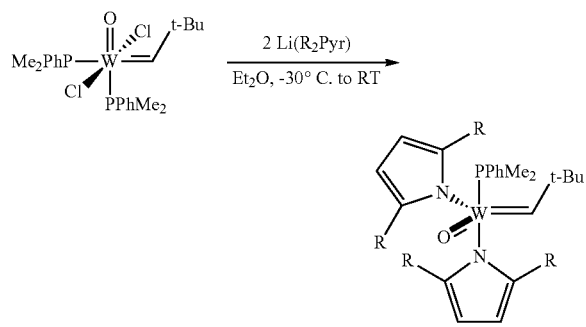

For I-7, R = Me;
For I-8, R = i-Pr;
For I-9, R = Ph.

We conclude that tungsten oxo alkylidene complexes are viable catalysts for the Z-selective metathesis coupling of terminal olefins. Without wishing to be bound by any particular theory, it is believed that the resulting selectivity is due to the small size of the oxo ligand relative to OHMT, the low rate of isomerization of the initial Z product relative to coupling of terminal olefins, and decomposition of the active catalyst under the conditions employed.

New Synthesis of Oxo Alkylidene Complexes of Tungsten

The original synthesis of W(O)(CH-t-Bu)Cl$_2$(PMe$_2$Ph)$_2$ and related bis-phosphine complexes was based on synthesis of a tantalum neopentylidene complex and transfer of the neopentylidene ligand from tantalum to tungsten, as shown below (L is PMe$_2$Ph):

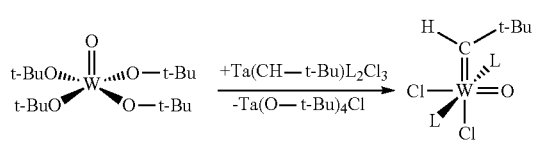

Ta(CH-t-Bu)Cl$_2$(PMe$_2$Ph)$_2$ is prepared form Ta(CH$_2$-t-Bu)$_3$Cl$_2$, which is synthesized from TaCl$_5$ and Zn(CH$_2$t-Bu)$_2$ in pentane. For this synthesis, Zn(CH$_2$t-Bu)$_2$ must be prepared and purified extensively before use. W(O)(O-t-Bu)$_4$ can be synthesized in modest yield in a reaction between W(O)Cl$_4$ and LiO-t-Bu and isolated through sublimation, but again the process is lengthy and indirect: i.e., the alkylidene is not prepared on tungsten. Other methods have been tried, including through alkylation of W(O)Cl$_4$. However, direct alkylation of W(O)Cl$_4$ with lithium, magnesium, aluminum, or zinc alkyls has been found to lead to complex mixtures that contain complexes in which the oxo group has been removed from the metal and/or the metal has been reduced. The several tungsten d$^0$ oxo alkyl complexes that are known generally cannot be synthesized in pure form and good yield through direct alkylation of tungsten oxo complexes.

The present invention provides new and better methods of making tungsten oxo alkylidene complexes from readily available starting material. Non-limiting examples are described herein.

In some embodiments, W(O)$_2$Cl$_2$ is prepared on a large scale in a reaction between tungsten hexachloride and hexamethyldisiloxane in dichloromethane. Pale yellow W(O)$_2$Cl$_2$(bipy) can be prepared on a large scale in essentially one step from WCl$_6$ through addition of bipyridine to a dichloromethane solution of W(O)$_2$Cl$_2$(DME) (DME=demethoxyethane). Addition of 3.7 equiv of neopentylmagnesium chloride to a solution of 2 in THF results in the formation of dark red solutions. After aqueous aerobic workup analogous to that reported by Schrauzer (Zhang, C.; Schlemper, E. O.; Schrauzer, G. N. Organometallics 1990, 9, 1016), yellow W(O)2(CH2-t-Bu)2(bipy) (3a) can be isolated in 70% yield. Similar reactions employing PhMe$_2$CH$_2$MgCl led to W(O)$_2$(CH$_2$CMe$_2$Ph)$_2$(bipy) (3b) in 67% yield. Proton NMR spectra are consistent with 3a,b having C$_{2v}$ symmetry with the two oxo ligands cis to each other and trans to bipy. Treatment of 3a with a mixture containing one equivalent of ZnCl$_2$(dioxane), slightly less than two equivalents of PMe$_2$Ph, and two equivalents of trimethylsilyl chloride (TMSCl) in toluene at 100° C. for two hours led to the formation of the tungsten oxo alkylidene complex, W(O)(CH-t-Bu)Cl$_2$(PMe$_2$Ph)$_2$, hexamethyldisiloxane (TMS$_2$O), neopentane, and ZnCl$_2$(bipy). Double recrystallization of the crude product from a mixture of ether and tetrahydrofuran gave 1a in 45% isolated yield. The neophylidene analog, W(O)(CHCMe$_2$Ph)Cl$_2$(PMe$_2$Ph)$_2$ (1b), was prepared in a similar manner and isolated in 39% yield as a yellow solid. Like 1a, 1b is a syn alkylidene on the basis of the J$_{CH\alpha}$ value for the alkylidene (126 Hz). The two phosphine ligands are equivalent and remain bound to tungsten on the NMR time scale at 22° C. with J$_{PW}$=333 Hz. The new synthesis of W(O)(CHR)Cl$_2$(PMe2Ph)$_2$ complexes 1a and 1b consists of three relatively simple steps starting from tungsten hexachloride, which is a significant improvement over the existing method.

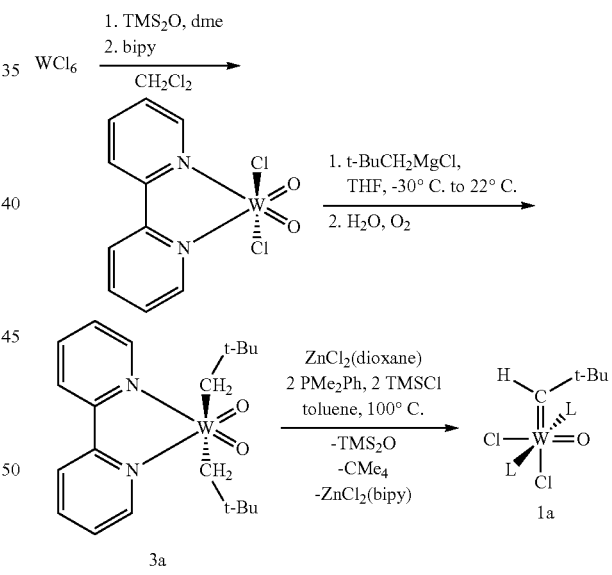

Without the intention to be limited by any theory, a mechanism is proposed for the above transformation. The mechanism of formation of the alkylidene in 1a,b is proposed to involve attack on one of the oxo ligands in W(O)$_2$(CH$_2$R)$_2$(bipy) (R=t-Bu, CMe2Ph) successively by 2 equiv of TMSCl to give TMS$_2$O and a W(O)Cl$_2$(CH$_2$R)$_2$(bipy) intermediate, from which CH$_3$R is lost to give W(O)(CHR)Cl2(bipy). Intramolecular abstraction of an α proton in the alkyl group becomes possible after one oxo ligand is replaced by two chlorides, especially in the presence of a ligand that could promote a abstraction in an 18-electron, seven-coordinate intermediate. There is a possibility that a abstraction takes place in an intermediate W(O)Cl(OSiMe3)(CH2R)2(bipy) species followed by replacement of the trimethylsiloxide with chloride upon further reaction with TMSCl. Treatment of W(O)2(CH2-t-Bu)2(bipy) with only 2 equiv of TMSCl leads to a product mixture whose NMR spectra are consistent with the major product being W(O)(CH-t-Bu)Cl2(bipy).

Synthesis of Oxo Alkylidene Derivatives

The reaction between 1a and LiOR (LiOR=LiOHIPT, LiOHMT) in benzene at 22° C. led to formation of the off-white W(O)(CHt-Bu)Cl(OR)(PMe2Ph) complexes 4a (OR=OHMT) and 4b (OR=OHIPT), each as a mixture of two syn alkylidene isomers. The phosphine remains bound to tungsten on the NMR time scale at 22° C. in both 4a and 4b. Addition of LiMe2Pyr to 4a,b led to isolation of W(O)(CH-t-Bu)($\eta^1$-Me2Pyr)(OHMT)(PMe2Ph) (5a) and W(O)(CH-t-Bu)($\eta^1$-Me2Pyr)(OHIPT) (5b), both of which were characterized through X-ray studies.11 Phosphine-free 5b is formed as a consequence of the greater steric demand of the OHIPT versus that of the OHMT ligand. The structure of 5a is a square pyramid with a syn neopentylidene in the apical position and the phosphine bound trans to the pyrrolide. The equilibrium constant for phosphine dissociation in 5a was estimated to be 0.015 M at room temperature through NMR studies, a value that corresponds to 57% dissociation of phosphine-free W(O)(CH-t-Bu)($\eta^1$-Me2Pyr)(OHMT) being present in a 20 mM solution of 5a in C6D6.

In some embodiments, the present invention provides methods to prepare tungsten oxo alkylidene species from a compound having the structure of formula V-b. In some embodiments, the compounds are obtained as 14 e species. In some embodiments, the compounds are obtained as 14 e species without $R^8$. In some embodiments, a compound of formula V-b is 4a. Exemplary methods and compounds prepared are described herein.

4a can be used to prepare other oxo alkylidene species, in addition to 5a, as shown in Scheme 1. Some of the prepared compounds are obtained as 14e without phosphine ligand.

resonances for the two protons on the pyrrolide ring are broad at room temperature, which, without the intention to be limited by any theory, suggests either hindered rotation of the diphenylpyrrolide ligand or an equilibrium between $\eta^1$ and $\eta^5$ coordination modes.

Figure 8:
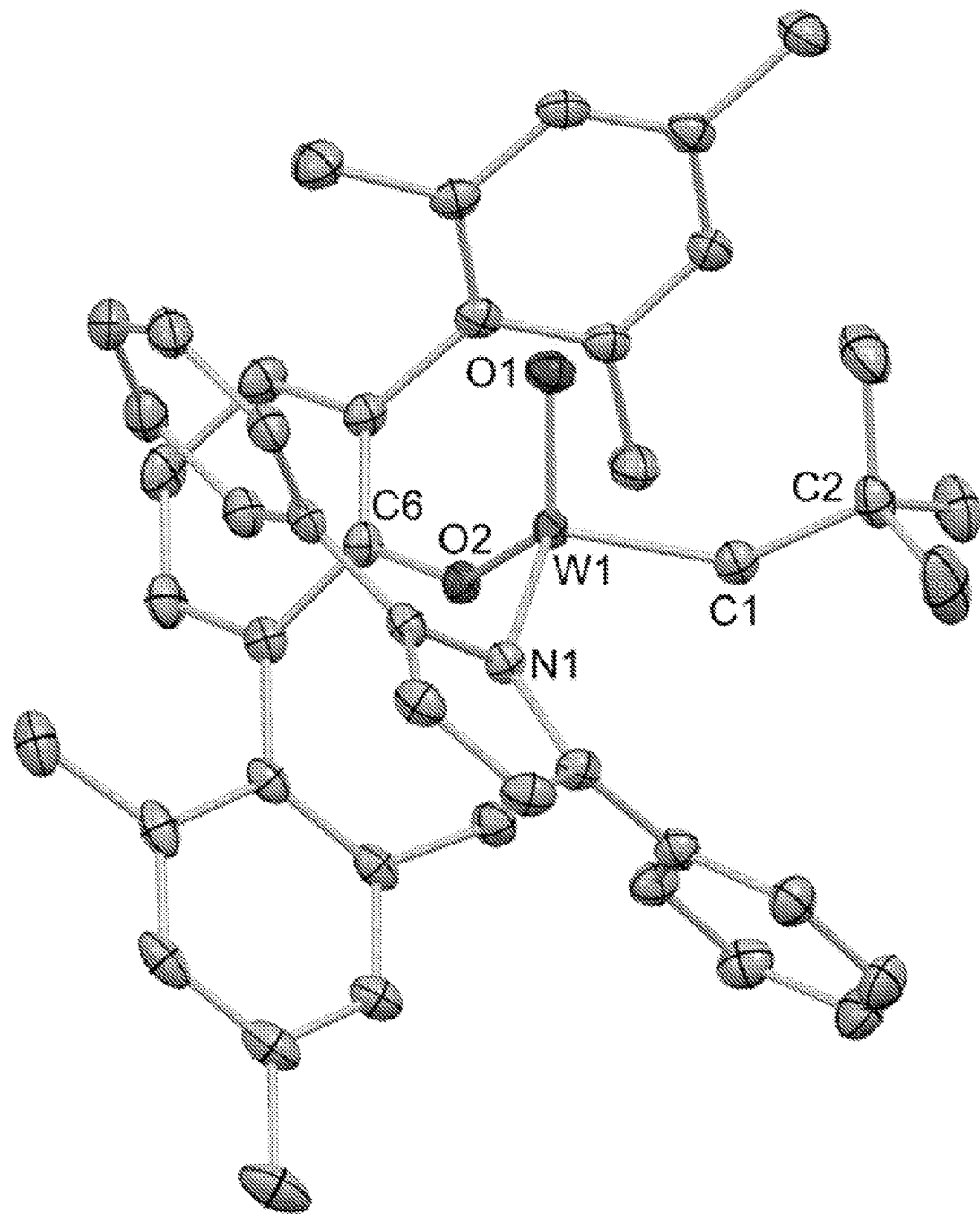
FIG. 8. Thermal ellipsoid plot (50% probability) of W(O)(CH-t-Bu)(Ph$_2$Pyr)(OHMT). Hydrogen atoms have been omitted for clarity. Selected bond distances (Å) and angles (deg): W1-C1=1.895(2), W1-O1=1.690(1), W1-O2=1.894(1), W1-N1=2.037(2); W1-C1-C2=141.1(1), W1-O2-C6=143.1(1).

Single crystals of 6 were grown from toluene/pentane solution at −30° C. A thermal ellipsoid drawing of the structure is shown in FIG. 8. The W=O distance (1.690(1) Å) is comparable to the W=O bond length in 5b (1.695(3) Å). The pyrrolide ligand is coordinated in ill fashion with an W—$N_{pyr}$ distance of 2.037(2) Å, versus the W—Npyr bond length in 5b (2.001(2) Å). In Mo(NAr)(CH-t-Bu)($\eta^1$-2,5-Ph2Pyr)($\eta^5$-2,5-Ph2Pyr), the Mo—$N_{pyr}$ bond length for the ill pyrrolide is slightly longer (2.1145(10) Å) than in 5b. The W—$N_{pyr}$ vector in 6 does not lie in the plane of the pyrrolide ligand: i.e., the pyrrolide is tipped so that the angle between the W—$N_{pyr}$ vector and the plane is 161.7°.

Figure 9:
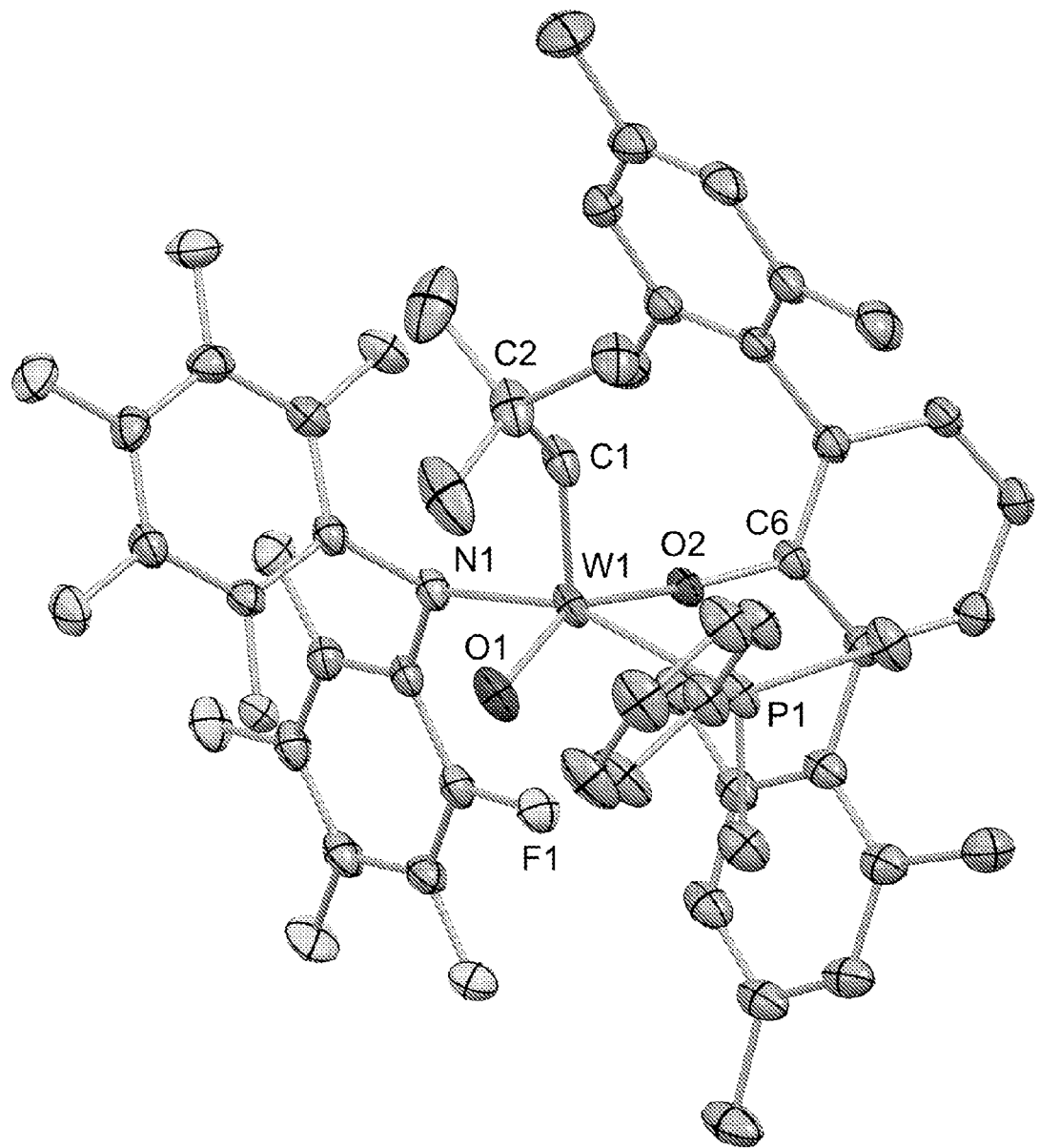
FIG. 9. Thermal ellipsoid plot (50% probability) of W(O)(CH-t-Bu)[N(C$_6$F$_5$)$_2$](OHMT)(PMe$_2$Ph). Hydrogen atoms have been omitted for clarity. Selected bond distances (Å) and angles (deg): W1-C1=1.898(2), W1-O1=1.710(2), W1-O2=1.965(1), W1-N1=2.127(2), W1-P1=2.564(1), W1-C1-C2=141(2), W1-O2-C6=154.0(1).

Treatment of 4a with LiN(C6F5)2 in CH2Cl2 led to formation of W(O)(CH-t-Bu)[N(C6F5)2](OHMT)(PMe2Ph) (7) in 60% isolated yield. The X-ray structure 7 showed it to be essentially a square pyramid with the syn alkylidene ligand in the apical position and the phosphine ligand trans to the amide (FIG. 9). The amido nitrogen atom is not planar (the three angles sum to 349.7(2)°) and one of the ortho fluorides could be interacting weakly with the metal trans to the alkylidene (W1-F1=2.758(1) Å), which is not unusual in complexes that contain the perfluorodiphenylamido ligand. The amido ligand could also be said to be "tipped" out of planarity, as found for the diphenylpyrrolide in 6. The broad alkylidene resonance in 7 results from the phosphine dissociating in solution at room temperature. A variable temperature $^1$H and $^{31}$P NMR study of a 74 mM solution of 7 in toluene-ds showed that the phosphine is bound on the NMR time scale below −20° C. (a sharp resonance is found at 2.69 ppm with $J_{PW}$=347 Hz), but in toluene at 22° C. $K_{eq}$ is ~0.002 M, i.e., ~50% of 7 is converted into W(O)(CH-t-Bu)[N—(C6F5)2](OHMT) at 74 mM concentration. At −20° C., 10 broadened $^{19}$F resonances are observed for 7, which suggests that the N(C6F5)2 ligand is not rotating freely at −20° C.

Addition of one equivalent of NaOSi(t-Bu)3 to 4a at room temperature resulted in formation of phosphine-free W(O)(CH-t-Bu)(OHMT)(Silox) (8) as the only product, according to $^1$H and $^{31}$P NMR data. 8 was very soluble in pentane. 8 was prepared from 250 mg of 4 and a solution of it in pentane was exposed to one atmosphere of ethylene; the metallacyclobu-

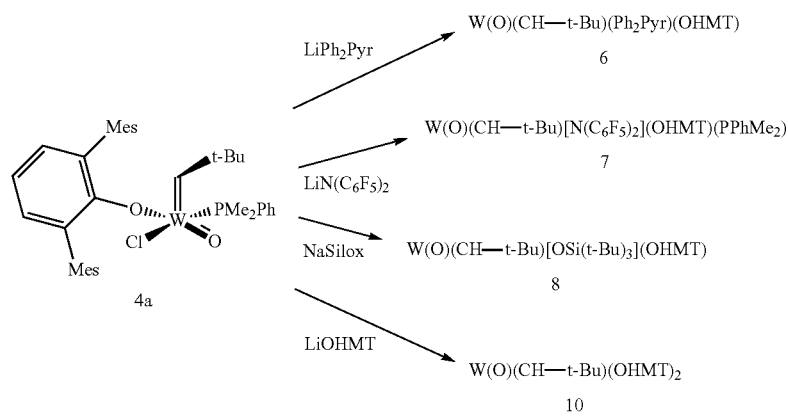

Scheme 1

Addition of 1 equiv of lithium 2,5-diphenylpyrrolide to a toluene solution of W(O)(CH-t-Bu)(OHMT)Cl(PMe2Ph) at room temperature led to the formation of yellow W(O)(CH-t-Bu)(Ph2Pyr)(OHMT) (6) in 57% isolated yield. The α proton resonance for the alkylidene resonance in the $^1$H NMR spectrum of 6 is found at 9.99 ppm (cf. 9.14 ppm in 5a) with $J_{CH}$=124 Hz, which is characteristic of a syn orientation of the alkylidene. Although the alkylidene resonance is broadened slightly, the $^{183}$W satellites are discernible ($J_{HW}$=10 Hz). The tane complex, W(O)(CH$_2$CH$_2$CH$_2$)(OHMT)(Silox) (9), crystallized out as light yellow crystals in 25% isolated yield. A 0.018 M solution of 9 in C$_6$D$_6$ under dinitrogen was found to consist of 98% 9 and 2% of what is proposed to be the methylidene complex, W(O)(CH$_2$)(OHMT)(Silox) (δCH$_2$ at 7.77 and 8.93 ppm), formed through loss of ethylene from 9. Heating a solution of 9 in C$_6$D$_6$ to 70° C. led to broadening of the metallacycle proton signals and the appearance of free ethylene and broadened methylidene signals, consistent with facile exchange of ethylene in the WC$_3$ ring on the NMR time scale. Only three metallacycle resonances are observed for W(O)(C$_3$H$_6$)(OHMT)(Silox) in C$_6$D$_6$ (4.10, 2.54, and 1.93 ppm, 1:1:1 ratio); presumably three other resonances are obscured. Three $^{13}$C resonances can be attributed to the metallacycle at 43.8, 41.5, and 22.3 ppm. The range of chemical shifts of metallacycle protons and carbons is indicative of squarepyramidal (SP) coordination of the metal center found for W(NAr)[CH$_2$CH(t-Bu)CH$_2$](O-t-Bu)$_2$.

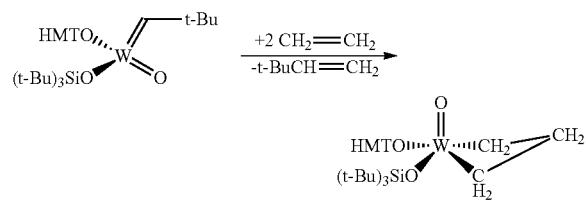

Figure 10:
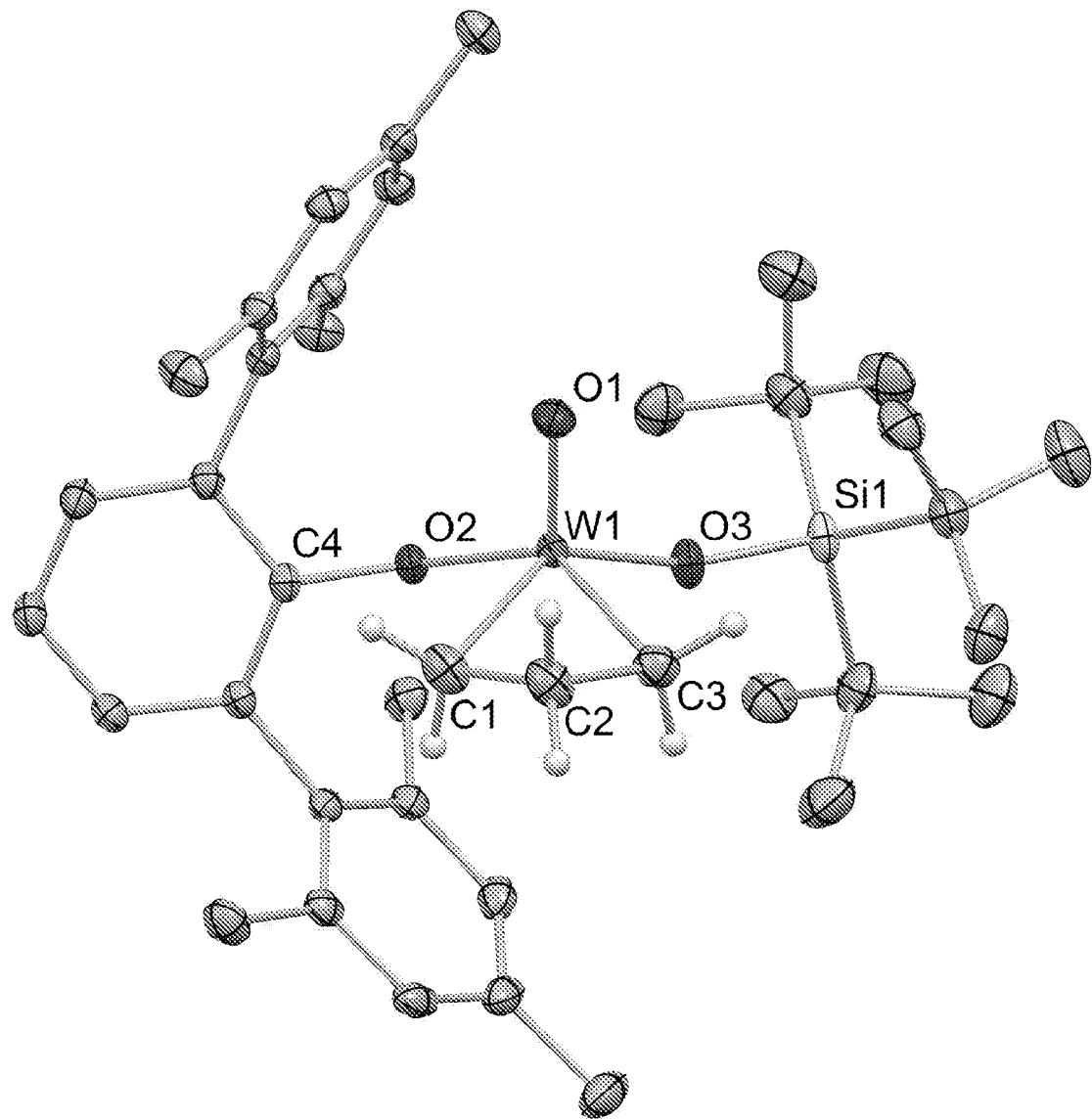
FIG. 10. Thermal ellipsoid plot (50% probability) of squarepyramidal W(O)(C$_3$H$_6$)(OHMT)(Silox). Hydrogen atoms, except for those on the metallacycle, have been omitted for clarity. Only the major component of disorder is shown. Selected bond distances (Å) and angles (deg): W1-C1=2.172(3), W1-C3=2.168(3), W1-O1=1.690(2), W1-O2=1.896(2), W1-O3=1.875(3), C1-C2=1.527(4), C2-C3=1.522(4); W1-C1-C2=95.0(2), W1-C3-C2=95.4(2), C1-C2-C3=95.6(2), C1-W1-C3=62.7(1), O2-W1-O3=103.3(1), O1-W1-O2=113.6(1), O1-W1-O3=113.4(1), W1-O2-C4=148.0(1), W1-O3-Si1=161.9(4).

Single crystals of 9 were grown from a mixture of toluene and pentane at −30° C. An X-ray structural study confirmed the proposed SP configuration of 9 in which the oxo ligand is in the apical position (FIG. 10). To our knowledge, 9 is the first structurally characterized metallacyclobutane derived from an oxo alkylidene and the first unsubstituted high oxidation state molybdacyclobutane or tungstacyclobutane that has a square pyramidal geometry. (All unsubstituted Mo or W imido metallacyclobutane complexes have TBP geometries.) The bond lengths and bond angles in the WC$_3$ ring in 9 are identical to those in W(NAr)[CH$_2$CH(t-Bu)CH$_2$][OCMe$_2$(CF$_3$)]$_2$ (within 3σ), as shown below. The WC$_3$ ring in 9 is bent with a 33.8° dihedral angle between the C1-W-C3 and C1-C2-C3 planes compared to a 33.4° angle in W(NAr)[CH$_2$CH(t-Bu)CH$_2$][OCMe$_2$(CF$_3$)]$_2$. Relatively long W—C$_β$ distances in SP metallacyclobutane complexes of W (W . . . C2=2.762(3) Å in 9) have led to the proposal that SP metallacyclobutane complexes are further from the transition state for loss of olefin to give an alkylidene than are TBP metallacycles.

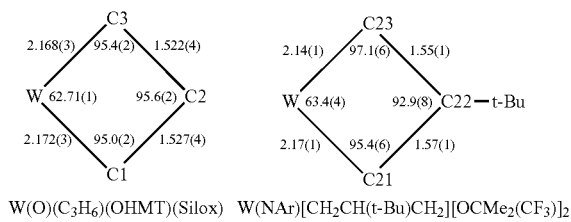

W(O)(C$_3$H$_6$)(OHMT)(Silox)   W(NAr)[CH$_2$CH(t-Bu)CH$_2$][OCMe$_2$(CF$_3$)]$_2$ Addition of one equivalent of LiOHMT to W(O)(CH-t-Bu)(OHMT)Cl(PMe$_2$Ph) (100° C., toluene) leads to formation of W(O)(CH-t-Bu)(OHMT)$_2$ (10) in good yield. 10 is also prepared in 41% isolated yield by treating W(O)(CH-t-Bu)Cl$_2$(PMe$_2$Ph)$_2$ with two equivalents of LiOHMT at 100° C. in toluene for 48 h. The resonance for the alkylidene proton in the proton NMR spectrum of 10 is found at 7.34 ppm with $^1J_{HW}$=14 Hz. Three mesityl methyl resonances were observed for the OHMT ligands in the proton NMR spectrum at 22° C., consistent with the OHMT ligands being equivalent, free rotation about the W—O bonds, and no rotation about the C—C bonds to the central phenyl ring. The two sets of ortho mesityl methyl groups arise from the fact that no symmetry plane bisects the C=W=O angle in 10.

When a pentane solution of 10 was placed under 1 atm of ethylene, a yellow precipitate can be isolated whose proton NMR spectrum in C$_6$D$_6$ shows that a mixture of W(O)(C$_3$H$_6$)(OHMT)$_2$ (11) and W(O)(CH$_2$)(OHMT)$_2$ (12) in a 3:1 ratio is present. We propose that the precipitate is pure 11, but upon dissolution in benzene some ethylene is lost from 11 to give the mixture of 11 and 12 in solution. Only 11 is sufficiently insoluble to precipitate in the manner described. Compound 12 can be isolated in pure form through repeated dissolution of mixtures of 11 and 12 in toluene followed by slow removal of the solvent in vacuo:

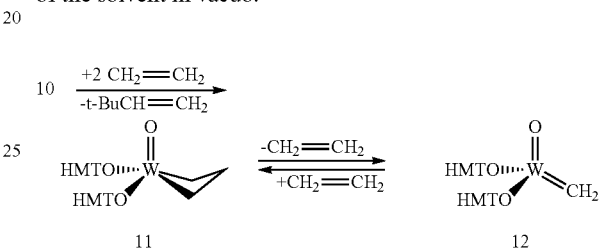

Two methylidene doublet resonances are observed in $^1$H NMR spectra of 12 in C$_6$D$_6$ at 8.90 ppm (H$_{syn}$, $^1J_{CH}$=160 Hz, $^2J_{HH}$=10 Hz) and 7.85 ppm (H$_{anti}$, $^1J_{CH}$=140 Hz). The lower J$_{CH}$ value for H$_{anti}$ is consistent with a C—H$_{anti}$ agostic interaction with the metal center. Three mesityl methyl resonances are found in the proton NMR spectrum at 22° C., as noted above for 10. Compound 12 was found to be stable in solution for at least 24 h at room temperature at a concentration of ~20 mM.

Figure 11:
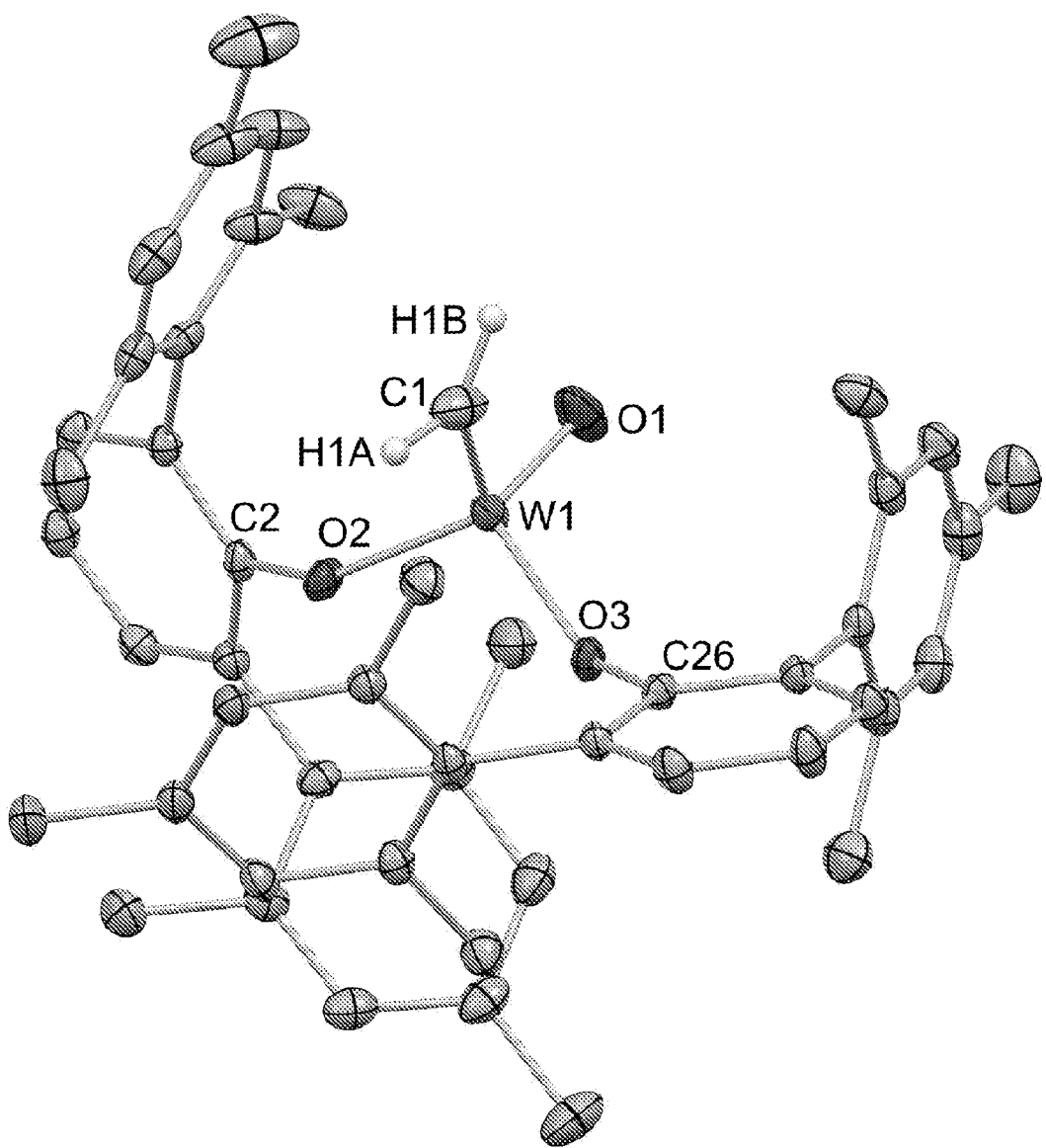
FIG. 11. Thermal ellipsoid plot (50% probability) of tetrahedral W(O)(CH$_2$)(OHMT)$_2$. Hydrogen atoms, except for those on the methylidene, have been omitted for clarity. Only the major component of disorder is shown. Selected bond distances (Å) and angles (deg): W1-C1=1.895(8), W1-O1=1.694(5), W1-O2=1.881(2), W1-O3=1.917(2); W1-C1-H1A=109(3), W1-C1-H1B=127(3), H1A-C1-H1B=123(4), O1-W1-C1=103.1(3), W1-O2-C2=136.3(2), W1-O3-C26=138.6(2).

An X-ray structural determination of 12 confirms that it is a monomeric tetrahedral 14-electron species in the solid state (FIG. 11). To our knowledge, this is the first X-ray structural study of an oxo methylidene complex. The oxo and methylidene ligands were found to be mutually disordered in a ratio of 71:29. The disorder could be resolved and the methylidene protons located in the major component; they were refined semifreely with appropriate bond length restraints (see Supporting Information). The W=C bond length (1.895 (8) Å) is similar to the M=C distances in two structurally-characterized 14e imido methylidene complexes of Mo (1.892(5) Å) and W (1.908(4) Å) (Schrock, R. R., King, A. J.; Marinescu, S. C.; Simpson, J. H.; Müller, P. *Organometallics* 2010, 29, 5241). The CH$_2$ plane is tilted ~9° relative to O=W=C plane, as is also found in the two Mo and W imido methylidene complexes (by 8°). The W=C1-H1a (H$_{anti}$) angle (109(3)°) is smaller than the W=C1-H1b (H$_{syn}$) angle (127(3)°), consistent with an agostic interaction between the CH$_{anti}$ bond and the metal center, and with the lower $^2J_{CHanti}$ values relative to $^2J_{CHsyn}$ values. The W=O bond length (1.694(5) Å) is comparable to that in W(O)(CH-t-Bu)(Me$_2$Pyr)(HIPTO) (1.695(3) Å, Peryshkov, D. V.; Schrock, R. R.; Takase, M. K.; Müller, P.; Hoveyda, A. H. *J. Am. Chem. Soc.* 2011, 133, 20754). The planes of two phenolate rings of the terphenoxides intersect at an angle of 81.5° with respect to each other. The nearly "perpendicular" relationship of the two OHMT ligands resembles a baseball cover and, without the intention to be limited by any theory, must hinder formation of the bis-μ-methylidene intermediate required for bimolecular decomposition yet must not block access of ethylene to the metal and formation of square pyramidal metallacyclobutane complex 11. Without the intention to be limited by theory, the 2,6-terphenoxide ligand contributes to discourage bimolecular decomposition.

EXPERIMENTAL

General Comments.

All manipulations were done either in a nitrogen-filled drybox or on an air-free dual-manifold Schlenk line. The solvents were sparged with nitrogen, passed through activated alumina, and stored over activated 4 Å Linde-type molecular sieves. Methylene chloride-$d_2$, benzene-$d_6$, and toluene-$d_8$ were distilled from calcium hydride ($CD_2Cl_2$) or sodium ketyl ($C_6D_6$, $C_7D8$), and stored over activated 4 Å Linde-type molecular sieves. NMR spectra were recorded using Varian spectrometers at 500 ($^1H$), 125 ($^{13}C$) and 121 ($^{31}P$) MHz, reported in δ (parts per million) relative to tetramethylsilane ($^1H$, $^{13}C$) or 85% phosphoric acid ($^{31}P$), and referenced to the residual $^1H/^{13}C$ signals of the deuterated solvent ($^1H$ (δ): benzene 7.16; methylene chloride 5.32, chloroform 7.26, toluene 7.09, 7.01, 6.97, 2.08; $^{13}C$ (δ): benzene 128.06; methylene chloride 53.84, chloroform 77.16, toluene 20.43) or external 85% phosphoric acid standard ($^{31}P$ (δ): 0) and hexafluorobenzene ($^{19}F$ (δ): −164.9). Midwest Microlab, Indianapolis, Ind. provided the elemental analysis results.

W(O)(CHCMe$_3$)Cl(HMTO)(PMe$_2$Ph), H(2,5-Ph$_2$Pyr), NH(C$_6$F$_5$)$_2$ were prepared according to reported procedures. H(Silox) was received as a generous gift from Professor Pete Wolczanski. NaSilox was prepared in the reaction of H(Silox) and NaH in THF. All other reagents were used as received unless noted otherwise.

Synthesis of W(O)$_2$Cl$_2$(Bipy).

The compound was prepared by a modification of the published procedure. A solution of hexamethyldisiloxane (21.482 g, 132 mmol, 2.1 eq) was added dropwise to the solution of tungsten hexachloride (25.000 g, 63.0 mmol) in 250 mL of dichloromethane. A solution of dimethoxyethane (13.058 g, 144.9 mmol, 2.3 eq) was added. The mixture was stirred for 2 h at room temperature during which time it became dark blue and contained a suspended precipitate. A pale blue solution was obtained after filtration of the mixture through Celite. A solution of 2,2'-bipyridine (10.330 g, 66.1 mmol, 1.05 eq) in 30 ml of dichloromethane was added and the mixture was stirred for 30 min. The precipitate was isolated by filtration, washed twice with 50 mL of dichloromethane, and dried under vacuum. The pale yellow powder was collected (25.824 g, 58.3 mmol, 92% yield). Anal. Calcd for $C_{10}H_8Cl_2N_2O_2W$: C, 27.10; H, 1.82; N, 6.32. Found: C, 26.27; H, 1.86; N, 5.97.

Synthesis of W(O)$_2$(CH$_2$CMe$_3$)$_2$(Bipy) (3a).

Compound 3a was prepared in a manner similar to the published procedure using W(O)$_2$Cl$_2$(bipy) instead of W(O)$_2$Br$_2$(bipy) as a starting material. A cold (−30° C.) solution of (CH$_3$)$_3$CCH$_2$MgCl in ether (40 mL, 1.66M, 3.7 eq.) was added to a cold (−30° C.) suspension of W(O)$_2$Cl$_2$(bipy) (8.000 g, 18.06 mmol) in 150 mL of THF. The reaction mixture was stirred at room temperature for 1 h. Volatiles were removed under vacuum leaving dark red residue. After addition of water (300 mL) the mixture was periodically shaken with CH$_2$Cl$_2$ (200 mL) in air. The organic fraction gradually changed color from green to yellow to orange. The mixture was filtered through Celite. The aqueous layer was separated and discarded. The organic layer was washed five times with portions of water (150 mL), dried with anhydrous MgSO$_4$, and concentrated to 20 mL volume, causing formation of a yellow solid. A portion of hexane (200 mL) was added and the mixture was filtered. The precipitate was recrystallized from dichloromethane/hexane. The solid product was isolated by filtration and dried under vacuum (6.464 g, 12.57 mmol, 70% yield): $^1H$ NMR (CD$_2$Cl$_2$) δ 9.55 (m, 2, bipy H), 8.39 (m, 2, bipy H), 8.15 (m, 2, bipy H), 7.58 (m, 2, bipy H), 0.94 (s, 18, CH$_2$CMe$_3$), 0.81 (s, 4, CH$_2$CMe$_3$, J$_{WH}$=8 Hz); $^{13}C$ NMR (CD$_2$Cl$_2$) δ 196.3, 152.0, 150.4, 139.2, 125.8, 123.6, 68.1, 34.9, 33.5. Anal. Calcd for $C_{20}H_{30}N_2O_2W$: C, 46.71; H, 5.88; N, 5.45. Found: C, 46.79; H, 5.91; N, 5.47.

Synthesis of W(O)$_2$(CH$_2$CMe$_2$Ph)$_2$(Bipy) (3b).

The compound was prepared in a manner analogous to that employed to prepare 3a. A cold (−30° C.) solution of (CH$_3$)$_2$PhCCH$_2$MgCl in ether (100 mL, 0.5 M, 3.7 equiv) was added to a cold (−30° C.) suspension of W(O)$_2$Cl$_2$(bipy) (6.000 g, 13.55 mmol) in 80 mL of THF. The reaction mixture was stirred at room temperature for 1 h. Volatiles were removed under vacuum, leaving a dark red residue. After addition of water (300 mL) the mixture was periodically shaken with CH$_2$Cl$_2$ (200 mL) in air. The organic fraction gradually changed color from green to yellow. The mixture was filtered through Celite. The aqueous layer was separated and discarded. The organic layer was washed five times with portions of water (150 mL), dried with anhydrous MgSO$_4$, and concentrated to 20 mL volume, causing formation of a pale yellow solid. A portion of hexane (150 mL) was added, and the mixture was filtered. The precipitate was recrystallized from chloroform/hexane. The solid product was isolated by filtration and dried under vacuum (5.85 g, 9.16 mmol, 67% yield): $^1H$ NMR (CD$_2$Cl$_2$) δ 8.95 (m, 2, bipy H), 8.24 (m, 2, bipy H), 8.03 (m, 2, bipy H), 7.35 (m, 2, bipy H), 7.05 (m, 10, CH$_2$CMe$_2$Ph), 1.38 (s, 12, CH$_2$CMe2Ph), 1.06 (s, 4, CH$_2$CMe$_2$Ph, J$_{WH}$=8 Hz); $^{13}C$ NMR (CD$_2$Cl$_2$) δ 154.1, 152.0, 149.9, 138.9, 127.7, 126.0, 125.8, 124.8, 123.6, 68.2, 41.3, 32.2. Anal. Calcd for $C_{30}H_{34}N_2O_2W$: C, 56.44; H, 5.37; N, 4.39. Found: C, 56.42; H, 5.44; N, 4.35.

Synthesis of W(O)(CHCMe$_3$)Cl$_2$(PMe$_2$Ph)$_2$ (La).

Compound 3a (3.80 g, 7.39 mmol) was mixed with ZnCl$_2$ (dioxane) (1.74 g, 7.76 mmol, 1.05 equiv) and PMe$_2$Ph (1.94 g, 14.04 mmol, 1.9 equiv) in 40 mL of toluene. The mixture was cooled to −30° C., and TMSCl (1.77 g, 16.26 mmol, 2.2 equiv) was added. The mixture was stirred at room temperature for 30 min and then heated to 100° C. for 2 h, during which time the color darkened and a precipitate formed. All the volatiles were removed under vacuum at 50° C. Benzene (40 mL) was added to the dark residue, and the mixture was filtered through Celite. Solvent was evaporated from the filtrate in vacuo, leaving a yellow solid and a brown oil. The residue was stirred with 40 mL of ether for 3 h, during which time the oil disappeared and a yellow solid remained. The solid was recrystallized twice from a mixture of ether and tetrahydrofuran at −30° C. to produce a yellow crystalline solid (2.03 g, 45% yield). The $^1H$ NMR spectrum of the product is identical with that reported: $^1H$ NMR (C$_6$D$_6$) δ 12.10 (t, 1, WCHCMe3, $^1J_{CH}$=125 Hz, $^3J_{PH}$=4 Hz), 7.65 (m, 4), 6.97 (m, 6), 1.92 (m, 12, PMe$_2$Ph), 0.82 (s, 9, WCHCMe$_3$). Anal. Calcd for $C_{21}H_{32}Cl_2OP_2W$: C, 40.87; H, 5.23. Found: C, 40.90; H, 5.12.

Synthesis of W(O)(CHCMe$_2$Ph)Cl$_2$(PMe$_2$Ph)$_2$ (1b).

The compound was prepared in a manner analogous to that described for 1a. Compound 3b (2.99 g, 4.68 mmol) was mixed with ZnCl$_2$(dioxane) (1.10 g, 4.91 mmol, 1.05 equiv) and PMe2Ph (1.22 g, 8.85 mmol, 1.8 equiv) in 40 mL of toluene. The mixture was cooled to −30° C., and TMSCl (1.17 g, 10.76 mmol, 2.3 equiv) was added. The mixture was stirred at room temperature for 30 min and was heated at 100° C. for 2 h, during which time the color darkened and a precipitate formed. The solvent volume was reduced to approximately 30 mL in vacuo, and 10 mL of pentane was added. The solution was filtered through Celite, and the volatiles were removed in vacuo, leaving a brown oil. The residue was recrystallized twice from a mixture of ether and tetrahydrofuran at −30° C. to give a yellow crystalline solid (1.24 g, 39% yield): $^1$H NMR ($C_6D_6$) δ 12.01 (t, 1, WCHCMe2Ph, $^1J_{CH}$=126 Hz, $^3J_{PH}$=4 Hz), 7.68 (m, 4), 7.03 (m, 8), 6.96 (m, 3), 1.94 (t, 6, $PMe_2Ph$), 1.58 (t, 6, $PMe_2Ph$), 1.27 (s, 6, WCHCMe$_2$Ph); $^{13}$C NMR ($C_6D_6$) δ 315.8 (t, WCHCMe$_2$Ph, $J_{PC}$=11 Hz), 150.6, 135.1 (t), 131.4 (t), 130.6, 128.75, 128.70, 128.65, 126.8, 126.1, 51.9, 30.9, 14.7 (td); $^{31}$P NMR ($C_6D_6$) δ 4.02 ($J_{PW}$=333 Hz). Anal. Calcd for $C_{26}H_{34}Cl_2OP_2W$: C, 45.97; H, 5.05. Found: C, 46.23; H, 4.99.

Synthesis of W(O)(CHCMe$_3$)(Ph$_2$Pyr)(OHMT). Synthesis of W(O)(CHCMe$_3$)(Ph$_2$Pyr)(OHMT) (6).

A solution of W(O)(CHCMe$_3$)Cl(OHMT)(PMe$_2$Ph) (300.0 mg, 0.388 mmol) in 10 mL of benzene was added to a portion of solid Li(Ph$_2$Pyr) (105.0 mg, 0.466 mmol, 1.2 equiv). The cloudy reaction mixture was stirred at room temperature for 24 h. The solvent was removed in vacuo to give brown oil. The product was extracted to toluene (5 mL) and the mixture was filtered through a bed of Celite. Toluene was removed in vacuo to produce brown oil. Yellow solid precipitated upon addition of pentane (4 mL) and the resulting suspension was filtered and washed with 5 mL of pentane. Yellow solid was recrystallized from toluene/pentane at −30° C.: yield 182.0 mg, 57%; $^1$H NMR ($C_6D_6$) δ 9.99 (s, 1, WCH-t-Bu, $^1J_{CH}$=124 Hz, $^2J_{WH}$=11 Hz), 7.24-6.94 (m, 12), 6.89 (s, 2), 6.65 (s, 2), 6.61 (d, 1), 6.46-6.14 (br., 2), 2.22 (s, 6, Ar Me), 2.18 (s, 6, Ar Me), 2.04 (s, 6, Ar Me), 0.71 (s, 9, WCH-t-Bu); $^{13}$C NMR ($C_6D_6$) δ 279.7 (WCH-t-Bu, $^1J_{CW}$=201 Hz), 157.4, 137.8, 137.5, 137.3, 136.2, 133.8, 133.5, 133.1, 131.5, 130.7, 129.4, 129.2, 129.1, 127.1, 126.4, 124.3, 123.1, 113.1, 111.4, 108.6, 42.9, 32.1, 21.4, 21.2, 21.1. Anal. Calcd for $C_{45}H_{77}NO_2W$: C, 66.10; H, 5.79; N, 1.71. Found: C, 65.93; H, 5.90; N, 1.76.

Synthesis of W(O)(CHCMe$_3$)[N($C_6F_5$)$_2$](OHMT)(PMe$_2$Ph) (7)

A solution of W(O)(CH-t-Bu)Cl(OHMT)(PMe$_2$Ph) (252 mg, 0.326 mmol) in 10 mL of dichloromethane was added to a portion of solid LiN($C_6F_5$)$_2$ (127 mg, 0.358 mmol, 1.1 equiv). The reaction mixture was stirred at room temperature for 8 h, during which time a white precipitate formed. The solvent was removed in vacuo to give a brown oil. The product was extracted into toluene (5 mL), and the solvent was filtered through a bed of Celite. Toluene was removed in vacuo to produce a yellow oil. The oil was dissolved in a ¼ mixture of ether and pentane and cooled to −30° C. The product was collected as an off-white solid: yield 230 mg, 65%; $^1$H NMR (74 mM in $C_6D5CD_3$, 22° C.) δ 10.21 (br, 1, WCH-t-Bu), 7.25 (m, 2), 7.00 (m, 3), 6.82 (m, 6), 6.64 (br, 2), 2.23 (br, 6, Ar Me), 2.10 (br, 6, Ar Me), 2.04 (br, 6, Ar Me), 1.20 (br, 6, PMe$_2$Ph) 0.60 (br, 9, WCH-t-Bu); $^{31}$P NMR (74 mM in $C_6D5CD_3$, 22° C.) δ 2.44 (br); $^1$H NMR (74 mM in PMe$_2$Ph, −20° C.) δ 10.37 (br, 1, WCH-t-Bu), 7.20 (m, 2), 6.95 (m, 3), 6.81 (m, 6), 6.72 (br, 1), 6.54 (br, 1), 2.35 (br, 3, Ar Me), 2.22 (br, 3, Ar Me), 2.17 (br, 6, Ar Me) 2.03 (br, 3, Ar Me), 2.00 (br, 3, Ar Me), 1.17 (d, 6, PMe$_2$Ph) 0.52 (br, 9, WCH-t-Bu); $^{13}$C NMR (74 mM in $C_6D5CD_3$, −20° C., C—F are expected to be weak) δ 297.3 (WCH-t-Bu), 160.1, 139.1, 138.5, 138.0, 137.6, 137.1, 136.8, 136.5, 135.0, 134.7, 133.8, 133.4, 133.0, 132.7, 131.9, 130.9, 130.8, 130.6, 129.7, 128.5, 128.4, 128.2, 109.9, 44.3, 29.8, 22.1, 21.8, 21.4, 21.1, 21.0, 20.9, 14.3 (d), 11.4 (d); $^{31}$P NMR (74 mM in $C_6D5CD_3$, −20° C.) δ 2.69 (s, $J_{PW}$=347 Hz); $^{19}$F NMR (74 mM in $C_6D5CD_3$, −20° C.) δ −146.18 (br, 1), −146.62 (br, 1), −152.04 (br, 1), −160.78 (br, 1), −165.66 (br, 1), −167.58 (br, 2), −168.91 (br, 1), −169.09 (br, 1), −174.82 (br, 1). Anal. Calcd for $C_{49}H_{46}F_{10}NO_2PW$: C, 54.21; H, 4.27; N, 1.29. Found: C, 54.50; H, 4.32; N, 1.59.

Synthesis of W(O)($C_3H_6$)(OHMT)(Silox) (9).

A cold (−30° C.) solution of W(O)(CH-t-Bu)(OHMT)Cl(PMe$_2$Ph) (250.0 mg, 0.323 mmol) in 10 mL of toluene was added to a portion of solid NaSilox (85.2 mg, 0.357 mmol, 1.1 equiv). The brown reaction mixture was stirred at room temperature for 3 h. The solvent was removed in vacuo to give brown oil. The product was extracted to toluene (5 mL), and the mixture was filtered through a bed of Celite. Toluene was removed in vacuo to produce a brown oil. Pentane (3 mL) was added to the oil. The solution was degassed by three successive freeze-pump-thaw cycles, and 1 atm of ethylene was added. The mixture was stirred at 0° C. for 1 h, during which time a yellow crystalline precipitate formed. The precipitate was filtered off, washed with 0.5 mL of cold pentane, and collected: yield 64 mg, 25%. A 0.018 M solution in $C_6D_6$ contained 98% of 4 and 2% of the corresponding methylidene along with the equivalent amount of ethylene: 1H NMR ($C_6D_6$) δ 7.02-6.90 (m, 7, Ar H), 4.10 (m, 1, W$C_3H_6$), 2.54 (m, 1, W$C_3H_6$), 2.26 (br s, 12, Ar Me), 2.20 (s, 6, Ar Me), 1.93 (m, 1, W$C_3H_6$), 1.05 (s, 27, SiCMe$_3$); $^{13}$C NMR ($C_6D_6$) δ 156.6, 136.8 (br), 136.4 (br), 135.0 (br), 134.4 (br), 130.6, 129.2, 128.7, 124.0, 43.8 (W$C_3H_6$), 41.4 (W$C_3H_6$), 30.0 (SiCMe$_3$), 23.9 (SiCMe$_3$), 22.3 (W$C_3H_6$), 21.4 (br, Ar Me), 21.2 (Ar Me). Anal. Calcd for $C_{39}H_{58}O_3SiW$: C, 59.42; H, 7.43. Found: C, 59.20; H, 7.11.

Synthesis of W(O)(CHCMe$_3$)(OHMT)$_2$ (10).

A solution of W(O)(CHCMe$_3$)Cl$_2$(PMe$_2$Ph) (200.0 mg, 0.324 mmol) in 10 mL of toluene was added to a solution of LiOHMT (261.6 mg, 0.778 mmol, 2.4 equiv). The reaction mixture was stirred at 100° C. for 48 h, and the volatiles were removed in vacuo to give a brown oil. The product was extracted into toluene (5 mL), and the mixture was filtered through a bed of Celite. The toluene was removed in vacuo to give a brown oil. Addition of 4 mL of pentane caused a yellow solid to precipitate. The solid was filtered off and washed with 3 mL of cold pentane: yield 124 mg, 41%; $^1$H NMR ($C_6D_6$) δ 7.34 (s, 1, WCH-t-Bu, $^1J_{CH}$=122 Hz, $^2J_{WH}$=14 Hz), 6.90 (br s, 4, Ar H), 6.87-6.85 (m, 8, Ar H), 6.83-6.80 (m, 2, Ar H), 2.26 (s, 12, Ar Me), 2.08 (s, 12, Ar Me), 2.03 (s, 12, Ar Me), 0.92 (s, 9, WCH-t-Bu); $^{13}$C NMR ($C_6D_6$) δ 253.6 (WCH-t-Bu), 158.5, 137.0, 136.7, 136.5, 134.9, 131.7, 130.7, 128.9, 128.8, 123.0, 41.1, 33.2, 21.6, 21.3, 20.8. Anal. Calcd for $C_{53}H_{60}O_3W$: C, 68.53; H, 6.51. Found: C, 68.22; H, 6.53.

Synthesis of W(O)(CH$_2$)(OHMT)$_2$ (12).

A sample of 11 (60 mg, 0.067 mmol) was dissolved in 1 mL of toluene, and the solvent was removed in vacuo at room temperature. After two additional dissolution/evacuation cycles, a brown oil was obtained. Toluene (0.1-0.2 mL) and pentane (0.3-0.5 mL) were added, and the sample was placed in a freezer at −30° C. for 2 days. Yellow crystals formed and were separated from the brown mother liquor by decantation: yield 32 mg, 55%; $^1$H NMR ($C_6D_6$) δ 8.90 (d, 1, WCH$_{syn}$, $^2J_{HH}$=10 Hz, $^1J_{CH}$=160 Hz), 7.85 (d, 1, WCH$_{anti}$, $^2J_{HH}$=10 Hz, $^1J_{CH}$=140 Hz), 6.90 (br s, 4, Ar H), 6.89-6.85 (m, 8, Ar H), 6.84-6.80 (m, 2, Ar H), 2.22 (s, 12, Ar Me), 2.00 (s, 12, Ar Me), 1.96 (s, 12, Ar Me); $^{13}$C NMR ($C_6D_6$) δ 225.8 (WCH2), 158.1, 137.2, 136.9, 136.7, 134.4, 131.5, 130.0, 128.3, 123.4, 123.0, 21.3, 20.9, 20.8. Anal. Calcd for $C_{49}H_{52}O_3W$: C, 67.43; H, 6.01. Found: C, 67.74; H, 6.12.

Synthesis of 1-MeO-2,6-($C_6F_5$)$_2$—$C_6H_3$.

1-MeO-2,6-[B(OH)$_2$]2-$C_6H_3$ (700 mg, 3.58 mmol), Pd(PPh$_3$)$_4$ (165 mg, 0.143 mmol) and $K_2CO_3$ (2.47 g, 17.9 mmol) were suspended in a mixture of toluene (12 mL) and ethanol (8 mL). C$_6$F$_5$Br (1.33 mL, 10.73 mmol) was added at room temperature. After refluxing for 1 day, the mixture was cooled to room temperature and filtered through silica plug and washed with CH$_2$Cl$_2$. Removal of the solvent gave a light yellow oil that was dissolved in a mixture of CH$_2$Cl$_2$ and hexane; colorless crystals formed at −35° C.; yield 1.021 g (65%): $^1$H NMR (300 MHz, acetone-d$_6$, 20° C.) δ 7.63 (d, $^3$J$_{HH}$=5 Hz, 2H), 7.48 (t, $^3$J$_{HH}$=5 Hz, 1H), 3.38 (s, 3H, Me); $^{19}$F NMR (282 MHz, acetone-d$_6$, 20° C.) δ −141.9 (m, 4F, o-F), −157.6 (t, $^3$J$_{FF}$=21 Hz, 2F, p-F), −165.0 (m, 4F, m-F); $^{13}$C{$^1$H}NMR (125 MHz, acetone-d$_6$, 20° C.) δ 158.3 (s, 1C), 145.8 (d, $^1$J$_{CF}$=298 Hz, 4C), 142.1 (d, $^1$J$_{CF}$=252 Hz, 2C), 138.8 (d, $^1$J$_{CF}$=250 Hz, 4C), 128.6 (s, 2C), 125.4 (s, 1C), 121.6 (s, 2C), 113.5 (t, $^2$J$_{CF}$=19 Hz, 2C). HRMS (ESI/[M+ Na]$^+$) Calcd for C$_{19}$H$_6$F$_{10}$NaO: 643.0151. Found: 643.0149.

Synthesis of HO-2,6-(C$_6$F$_5$)$_2$—C$_6$H$_3$.

1-MeO-2,6-(C$_6$F$_5$)$_2$C6H$_3$ (552 mg, 1.25 mmol) was dissolved in CH$_2$Cl$_2$ (20 mL). BBr$_3$ (0.238 mL, 2.51 mmol) was added at 0° C. The mixture was warmed up to room temperature. After 16 hours, water (10 mL) was added to quench the reaction. The organic layer was separated from the aqueous layer and the aqueous layer was extracted with diethyl ether. The organic parts were combined and dried with MgSO$_4$. Removal of the solvent in vacuo gave a white solid that was recrystallized from hexanes to give colorless crystals; yield 482 mg (90%): $^1$H NMR (300 MHz, CDCl$_3$, 20° C.) δ 7.42 (d, $^3$J$_{HH}$=8 Hz, 2H), 7.28 (t, $^3$J$_{HH}$=7 Hz, 1H), 4.92 (br, 1H, OH); $^{19}$F NMR (282 MHz, CDCl$_3$, 20° C.) δ −139.9 (m, 4F, o-F), −154.3 (t, $^3$J$_{FF}$=21 Hz, 2F, p-F), −165.0 (m, 4F, m-F); $^{13}$C{$^1$H}NMR (125 MHz, CDCl$_3$, 20° C.) δ 151.3 (s, 1C), 145.0 (d, $^1$J$_{CF}$=250 Hz, 4C), 141.4 (d, $^1$J$_{CF}$=242 Hz, 2C), 138.2 (d, $^1$J$_{CF}$=253 Hz, 4C), 133.6 (s, 2C), 121.7 (s, 1C), 115.0 (s, 2C), 111.2 (t, $^2$J$_{CF}$=19 Hz, 2C). Anal. Calcd for C$_{14}$H$_4$F$_{10}$O: C, 50.72; H, 0.95. Found: C, 50.96; H, 1.06.

X-Ray Crystal Structure Determination Details.

Low-temperature diffraction data (φ- and ω-scans) were collected on a Bruker-AXS X8 Kappa Duo diffractometer coupled to a Smart APEX 2 CCD detector with Mo K$_α$ radiation (λ=0.71073 Å) from an IμS micro-source. Absorption and other corrections were applied using SADABS. All structures were solved by direct methods using SHELXS and refined against F2 on all data by full-matrix least squares with SHELXL-97 using established refinement approaches. All non-hydrogen atoms were refined anisotropically. Hydrogen atoms were included in the models at geometrically calculated positions and refined using a riding model, except for alkylidene, metallacycle, and methylidene protons. Coordinates for these hydrogen atoms were taken from the difference Fourier synthesis, and the hydrogen atoms were subsequently refined semi-freely with the help of distance restraints. The isotropic displacement parameters of all hydrogen atoms were fixed to 1.2 times the Ueq value of the atoms they are linked to (1.5 times for methyl groups). All disordered atoms were refined with the help of similarity restraints on the 1,2- and 1,3-distances and displacement parameters as well as rigid bond restraints for anisotropic displacement parameters.

W(O)(CH-t-Bu)(Ph$_2$Pyr)(OHMT) (6) crystallizes in the triclinic space group with P$\bar{1}$ one molecule in the asymmetric unit. Coordinates for the hydrogen atom bound to C1 were taken from the difference Fourier synthesis as noted above.

W(O)(CH-t-Bu)(N(C$_6$F$_5$)$_2$)(OHMT)(PMe$_2$Ph) (7) crystallizes in monoclinic space group P2$_1$/c with one molecule in the asymmetric unit. Coordinates for the hydrogen atom bound to C1 were taken from the difference Fourier synthesis as noted above.

W(O)(C$_3$H$_6$)(OHMT)(Silox) (9) crystallizes in the triclinic space group P$\bar{1}$ with one molecule in the asymmetric unit. The tungsten atom and oxo ligand were modeled as a two-component disorder, and the ratio of the occupancies was refined to 0.9687(6):0.0313(6). The Silox ligand was also found to be disordered over two positions, and the ratio of occupancies was refined to 0.521(8):0.479(8). The anisotropic displacement parameters for silicon and carbon atoms of the Silox group were constrained to be equivalent, pairwise.

W(O)(CH$_2$)(OHMT)$_2$ (12) crystallizes in the monoclinic space group P2$_1$/n with one molecule in the asymmetric unit. The tungsten atom, oxo, and methylidene ligand were modeled as a two-component disorder, and the ratio of the occupancies was refined to 0.711(1):0.289(1). The anisotropic displacement parameters for the tungsten (W1, W1 Å), oxo, and chloride ligands (C1, O1A and C1A, O1) were constrained to be equivalent, pairwise. Coordinates of the hydrogen atoms bound to C1 were taken from the difference Fourier synthesis as noted above. The hydrogen atoms bound to C1A, the minor component of the disorder, could not be found in the difference Fourier synthesis and were not included in the model.

Crystal data were presented below.

TABLE 12

Crystal data and structure refinement for W(O)(CHCMe$_3$)(Ph$_2$Pyr) (OHMT).

| | |
|---|---|
| Identification code | X8_12012 |
| Empirical formula | C45 H47 N O2 W |
| Formula weight | 817.69 |
| Temperature | 100(2) K |
| Wavelength | 0.71073 Å |
| Crystal system | Triclinic |
| Space group | P$\bar{1}$ |
| Unit cell dimensions | a = 9.6557(8) Å    α = 83.319(2)° |
| | b = 10.7803(9) Å    β = 79.010(2)° |
| | c = 19.4906(17) Å    γ = 73.730(2)° |
| Volume | 1907.6(3) Å$^3$ |
| Z | 2 |
| Density (calculated) | 1.424 Mg/m$^3$ |
| Absorption coefficient | 3.065 mm$^{-1}$ |
| F(000) | 828 |
| Crystal size | 0.10 × 0.09 × 0.05 mm$^3$ |
| Theta range for data collection | 1.07 to 31.00°. |
| Index ranges | −13 <= h <= 13, −15 <= k <= 15, −28 <= l <= 27 |
| Reflections collected | 82590 |
| Independent reflections | 12148 [R(int) = 0.0414] |
| Completeness to theta = 31.00° | 99.9% |
| Absorption correction | Semi-empirical from equivalents |
| Max. and min. transmission | 0.8668 and 0.7492 |
| Refinement method | Full-matrix least-squares on F$^2$ |
| Data/restraints/parameters | 12148/1/454 |
| Goodness-of-fit on F$^2$ | 1.028 |
| Final R indices [I > 2sigma(I)] | R1 = 0.0209, wR2 = 0.0463 |
| R indices (all data) | R1 = 0.0254, wR2 = 0.0479 |
| Largest diff. peak and hole | 1.277 and −0.764 e.Å$^{-3}$ |

TABLE 13

Crystal data and structure refinement for W(O)(CHCMe$_3$)[N(C$_6$F$_5$)$_2$](OHMT)(PMe$_2$Ph).

| | |
|---|---|
| Identification code | X8_12046 |
| Empirical formula | C49 H46 F10 N O2 P W |
| Formula weight | 1085.69 |
| Temperature | 100(2) K |
| Wavelength | 0.71073 ≈ |
| Crystal system | Monoclinic |
| Space group | P2(1)/c |
| Unit cell dimensions | a = 12.0498(5) Å    a = 90° |
| | b = 21.0063(10) Å    b = 95.3650(10)° |
| | c = 17.9963(8) Å    g = 90° |

TABLE 13-continued

Crystal data and structure refinement for W(O)(CHCMe₃)[N(C₆F₅)₂](OHMT)(PMe₂Ph).

| | |
|---|---|
| Volume | 4535.3(4) Å³ |
| Z | 4 |
| Density (calculated) | 1.590 Mg/m³ |
| Absorption coefficient | 2.664 mm⁻¹ |
| F(000) | 2168 |
| Crystal size | 0.168 × 0.095 × 0.068 mm³ |
| Theta range for data collection | 1.49 to 30.62°. |
| Index ranges | −17 <= h <= 17, −12 <= k <= 30, −25 <= l <= 25 |
| Reflections collected | 120239 |
| Independent reflections | 13947 [R(int) = 0.0367] |
| Completeness to theta = 30.62° | 99.8% |
| Absorption correction | Semi-empirical from equivalents |
| Max. and min. transmission | 0.878 and 0.722 |
| Refinement method | Full-matrix least-squares on F² |
| Data/restraints/parameters | 13947/1/591 |
| Goodness-of-fit on F² | 1.066 |
| Final R indices [I > 2sigma(I)] | R1 = 0.0259, wR2 = 0.0559 |
| R indices (all data) | R1 = 0.0297, wR2 = 0.0573 |
| Largest diff. peak and hole | 1.809 and −0.862 e.Å⁻³ |

TABLE 14

Crystal data and structure refinement for W(O)(C₃H₆)(OHMT)(Silox).

| | |
|---|---|
| Identification code | X8_12002 |
| Empirical formula | C39 H58 O3 Si W |
| Formula weight | 786.79 |
| Temperature | 100(2) K |
| Wavelength | 0.71073 Å |
| Crystal system | Triclinic |
| Space group | P$\bar{1}$ |
| Unit cell dimensions | a = 9.3385(10) Å  α = 91.207(2)° |
| | b = 12.9036(14) Å  β = 92.359(2)° |
| | c = 15.7140(18) Å  γ = 99.810(2)° |
| Volume | 1863.5(4) Å³ |
| Z | 2 |
| Density (calculated) | 1.402 Mg/m³ |
| Absorption coefficient | 3.165 mm⁻¹ |
| F(000) | 808 |
| Crystal size | 0.12 × 0.12 × 0.05 mm³ |
| Theta range for data collection | 1.30 to 30.52°. |
| Index ranges | −13 <= h <= 13, −18 <= k <= 18, −22 <= l <= 22 |
| Reflections collected | 82344 |
| Independent reflections | 11320 [R(int) = 0.0611] |
| Completeness to theta = 30.52° | 99.2% |
| Absorption correction | Semi-empirical from equivalents |
| Max. and min. transmission | 0.8578 and 0.7026 |
| Refinement method | Full-matrix least-squares on F² |
| Data/restraints/parameters | 11320/288/489 |
| Goodness-of-fit on F² | 1.028 |
| Final R indices [I > 2sigma(I)] | R1 = 0.0255, wR2 = 0.0506 |
| R indices (all data) | R1 = 0.0338, wR2 = 0.0531 |
| Largest diff. peak and hole | 0.775 and −0.795 e.Å⁻³ |

TABLE 15

Crystal data and structure refinement for W(O)(CH₂)(OHMT)₂.

| | |
|---|---|
| Identification code | X8_12011 |
| Empirical formula | C49 H53 O3 W |
| Formula weight | 873.76 |
| Temperature | 100(2) K |
| Wavelength | 0.71073 Å |
| Crystal system | Monoclinic |
| Space group | P2(1)/n |
| Unit cell dimensions | a = 15.1114(7) Å  α = 90° |
| | b = 15.4585(7) Å  β = 96.5350(10)° |
| | c = 17.5246(8) Å  γ = 90° |
| Volume | 4067.1(3) Å³ |
| Z | 4 |
| Density (calculated) | 1.427 Mg/m³ |
| Absorption coefficient | 2.881 mm⁻¹ |
| F(000) | 1780 |
| Crystal size | 0.04 × 0.01 × 0.01 mm³ |
| Theta range for data collection | 1.69 to 29.57°. |
| Index ranges | −20 <= h <= 20, −21 <= k <= 21, −24 <= l <= 24 |
| Reflections collected | 91677 |
| Independent reflections | 11396 [R(int) = 0.0458] |
| Completeness to theta = 29.57° | 100.0% |
| Absorption correction | Semi-empirical from equivalents |
| Max. and min. transmission | 0.9718 and 0.9059 |
| Refinement method | Full-matrix least-squares on F² |
| Data/restraints/parameters | 11396/10/506 |
| Goodness-of-fit on F² | 1.210 |
| Final R indices [I > 2sigma(I)] | R1 = 0.0409, wR2 = 0.0803 |
| R indices (all data) | R1 = 0.0481, wR2 = 0.0824 |
| Largest diff. peak and hole | 2.698 and −1.329 e.Å⁻³ |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

What is claimed is:

1. A method for performing an olefin metathesis reaction, comprising providing a compound of formula I-c:

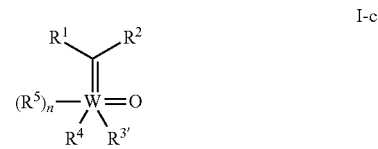

I-c wherein:
each of R¹ and R² is independently R, —OR, —SR, —N(R)₂, —OC(O)R, —SOR, —SO₂R, —SO₂N(R)₂, —C(O)N(R)₂, —NRC(O)R, or —NRSO₂R;
R³' is R³ or —OSi(R)₃;
R³ is R, —N(R)₂, —NRC(O)R, —NRC(O)OR, —NRC(O)N(R)₂, —NRSO₂R, —NRSO₂N(R)₂, —NROR, NR$_3$, —OR, O(R)$_2$, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

R$^4$ is halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from C$_{1-20}$ aliphatic, C$_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

n is 0, 1, or 2;

each R$^5$ is independently a monodentate ligand, or two R$^5$ are taken together with their intervening atoms to form an optionally substituted bidentate group; and two or more of R$^1$, R$^2$, R$^3$, R$^4$ and R$^5$ may be taken together with their intervening atoms to form an optionally substituted polydentate ligand;

wherein the compound is other than WO(CH-t-Bu)(O-2,6-Ph$_2$C$_6$H$_3$)$_2$(R$^5$)$_n$, WO(CH-t-Bu)(O-t-Bu)$_2$(R$^5$)$_n$, W(O)(CHCMe$_3$)(Me$_2$Pyr)$_2$(PMe$_2$Ph)$_n$, and WO(CH—CH═C(Ph)$_2$)(OC(CH$_3$)(CF$_3$)$_2$)$_2$(R$^5$), wherein Me$_2$Pyr is 2,5-dimethylpyrrolyl.

2. The method of claim 1, wherein:

R$^{3'}$ is —OR or —OSi(R)$_3$;

R$^4$ is —N(R)$_2$, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur.

3. The method of claim 1, wherein the compound of formula I-c promotes Z-selective olefin metathesis.

4. The method of claim 1, wherein R$^{3'}$ is —OR, wherein R is optionally substituted phenyl.

5. The method of claim 4, wherein R$^{3'}$ is

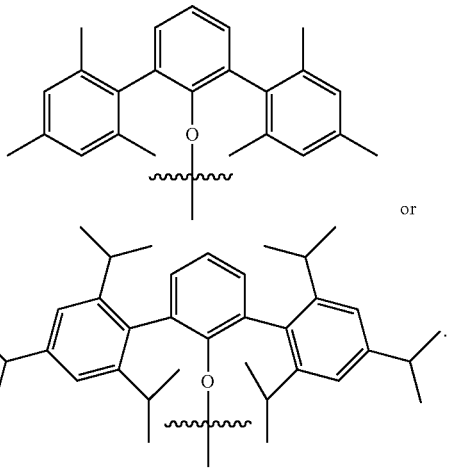

6. The method of claim 2, wherein R$^4$ is —N(R)$_2$, wherein the two R groups are taken together with the nitrogen to form an optionally substituted 3-8 membered saturated, partially unsaturated, or aryl ring having 0-3 additional heteroatoms not including the N atom from —N(R)$_2$ independently selected from nitrogen, oxygen, or sulfur.

7. The method of claim 6, wherein R$^4$ is

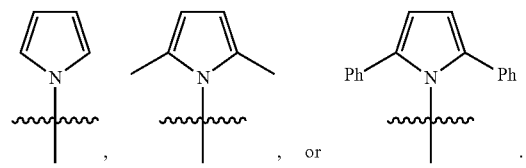

8. The method of claim 2, wherein the compound of formula I-c is selected from:

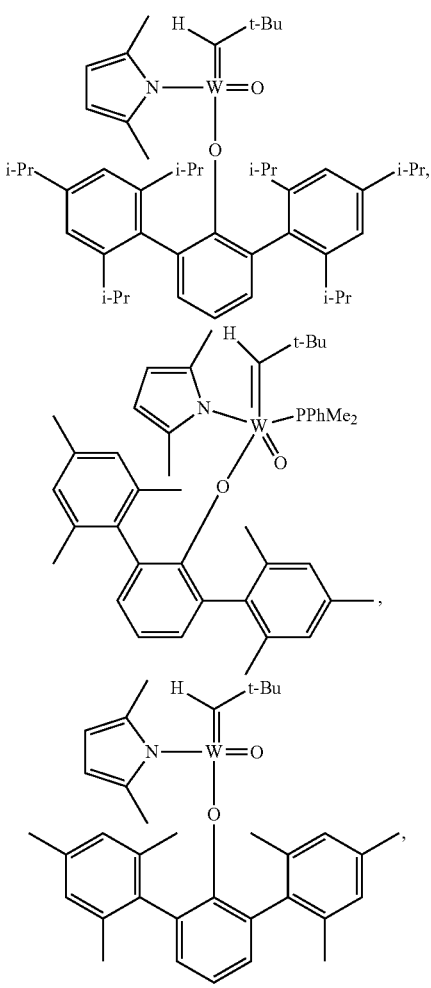

W(O)(CH-t-Bu)(Ph₂Pyr)(OHMT), W(O)(CH-t-Bu)(Ph₂Pyr)(OHIPT), W(O)(CH-t-Bu)[N(C₆F₅)₂](OHMT)(PPhMe₂), W(O)(CH-t-Bu)[N—(C₆F₅)₂](OHMT), W(O)(CH-t-Bu)(Me₂Pyr)(DFTO)(PPhMe₂), W(O)(CH-t-Bu)(Me₂Pyr)(DFTO), W(O)(CHCMe₂Ph)(Me₂Pyr)(DFTO)(PPhMe₂), W(O)(CHCMe₂Ph)(Me₂Pyr)(DFTO), and W(O)(CH-t-Bu)[N—(C₆F₅)₂](DFTO).

9. The method of claim 1, wherein:

$R^{3'}$ is —OR; and $R^4$ is —OR.

10. The method of claim 1, wherein:

$R^{3'}$ is —OSi(R)₃; and $R^4$ is —OR.

11. The method of claim 1, wherein the compound of formula I-c is W(O)(CH-t-Bu)(OHMT)₂, W(O)(CH-t-Bu)(OHIPT)₂, W(O)(CH-t-Bu)(DFTO)₂, or WO(CH-t-Bu)[OSi(t-Bu)₃](OHMT).

12. The method of claim 1, wherein n is 0.

13. The method of claim 1, further comprising providing Lewis acid.

14. The method of claim 1, wherein:

$R^{3'}$ is $R^3$;

$R^3$ is —OR; and $R^4$ is —N(R)₂.

15. The method of claim 1, wherein:

$R^3$ is an optionally substituted group selected from:

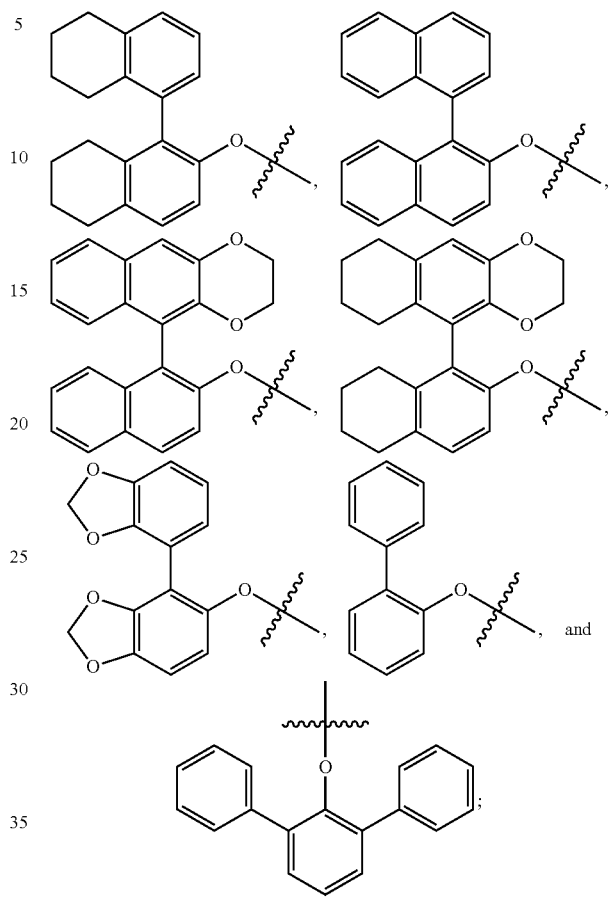

and $R^4$ is —N(R)₂, wherein the two R groups are taken together with the nitrogen to form an optionally substituted 3-8 membered saturated, partially unsaturated, or aryl ring having 0-3 additional heteroatoms not including the N atom from —N(R)₂ independently selected from nitrogen, oxygen, or sulfur.

16. The method of claim 1, wherein $R^4$ is optionally substituted pyrrolyl.

17. A method for performing an olefin metathesis reaction, comprising providing a compound of formula IX:

wherein $R^{1'}$ and $R^{2'}$ are taken together with W to form an optionally substituted 3-8 membered saturated or partially unsaturated ring having, in addition to the intervening metal atom, 0-4 heteroatoms independently selected from nitrogen, oxygen, or sulfur, wherein both $R^{1'}$ and $R^{2'}$ are directly bonded to W through carbon atoms;

$R^{3'}$ is $R^3$ or —OSi(R)₃;

each of $R^3$ and $R^4$ is independently halogen, R, —N(R)₂, —NRC(O)R, —NRC(O)OR, —NRC(O)N(R)₂, —NRSO$_2$R, —NRSO$_2$N(R)$_2$, —NROR, NR$_3$, —OR, O(R)$_2$, a phosphorus-containing ligand, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from C$_{1-20}$ aliphatic, C$_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

n is 0, 1, or 2;

each R$^5$ is independently a monodentate ligand, or two R$^5$ are taken together with their intervening atoms to form an optionally substituted bidentate group; and two or more of R$^{1'}$, R$^{2'}$, R$^3$, R$^4$ and R$^5$ may be taken together with their intervening atoms to form an optionally substituted polydentate ligand; and wherein the compound is other than

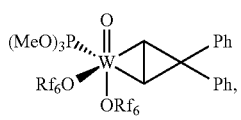

wherein —ORf$_6$ is —OC(CH$_3$)(CF$_3$)$_2$.

18. The method of claim 17, wherein R$^{1'}$ and R$^{2'}$ are taken together with W to form an optionally substituted 4-membered metallacyclobutane.

19. A method of preparing a compound of formula V-a:

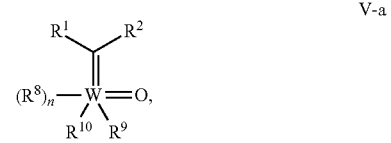

comprising providing a compound of formula VI:

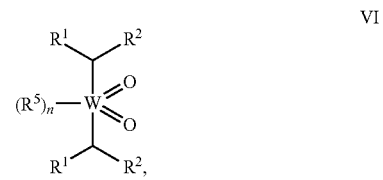

wherein:

n is 0, 1, or 2;

each of R$^1$ and R$^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;

each of R$^5$ and R$^8$ is independently a monodentate ligand, or two R$^5$ or two R$^8$ are taken together with their intervening atoms to form an optionally substituted bidentate group;

each of R$^9$ and R$^{10}$ is independently halogen; and each R is independently hydrogen or an optionally substituted group selected from C$_{1-20}$ aliphatic, C$_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur.

20. The method of claim 19, wherein n is 2.

* * * * *